US012648685B2

(12) United States Patent
Laakso et al.

(10) Patent No.: US 12,648,685 B2
(45) Date of Patent: Jun. 9, 2026

(54) ROBOTIC SURGICAL SYSTEMS WITH DEXTEROUS ENDOSCOPE

(71) Applicant: Covidien LP, Mansfield, MA (US)

(72) Inventors: Aki Hannu Einari Laakso, Raleigh, NC (US); Hans Christian Pflaumer, Apex, NC (US); Rupert Anthony Barton, Cambridge (GB); Adam Richard Turner, Cambridge (GB); Paul Smitheman, Cambridge (GB); Antony R. Burness, Cambridge (GB); Robert Ian Noakes, Cambridgeshire (GB); Marcus Joseph Wolf, Teignmouth (GB)

(73) Assignee: Covidien LP, Mansfield, MA (US)

( * ) Notice: Subject to any disclaimer, the term of this patent is extended or adjusted under 35 U.S.C. 154(b) by 293 days.

(21) Appl. No.: 18/277,291

(22) PCT Filed: Mar. 15, 2022

(86) PCT No.: PCT/CA2022/050392

§ 371 (c)(1),
(2) Date: Aug. 15, 2023

(87) PCT Pub. No.: WO2022/193009

PCT Pub. Date: Sep. 22, 2022

(65) Prior Publication Data

US 2024/0298883 A1 Sep. 12, 2024

Related U.S. Application Data

(60) Provisional application No. 63/161,170, filed on Mar. 15, 2021.

(51) Int. Cl.
A61B 1/00 (2006.01)
A61B 1/008 (2006.01)
A61B 1/05 (2006.01)

(52) U.S. Cl.
CPC ........ A61B 1/0016 (2013.01); A61B 1/00135 (2013.01); A61B 1/008 (2013.01); A61B 1/051 (2013.01)

(58) Field of Classification Search
CPC . A61B 1/0052; A61B 1/0055; A61B 1/00193; A61B 1/0057; A61B 1/0016;
(Continued)

(56) References Cited

U.S. PATENT DOCUMENTS 4,677,471 A * 6/1987 Takamura ................ A61B 1/05
600/110
6,132,368 A 10/2000 Cooper
(Continued)

FOREIGN PATENT DOCUMENTS

EP 2996613 A1 3/2016

OTHER PUBLICATIONS

Extended European Search Report issued in corresponding European Application No. 22770130.7 dated Jan. 8, 2025, 9 pages.

*Primary Examiner* — Timothy J Neal
(74) *Attorney, Agent, or Firm* — Carter, DeLuca & Farrell, LLP

(57) ABSTRACT

A surgical system includes a drive assembly and a dexterous endoscope. The endoscope defines a longitudinal axis and is actuatable by the drive assembly. The endoscope includes a camera assembly and an articulation assembly. The articulation assembly supports the camera assembly and is actuatable to move the camera assembly relative to the longitudinal axis. The distal wrist assembly includes links that are movable relative to one another, and the proximal wrist assembly includes links that are movable relative to one another.

20 Claims, 61 Drawing Sheets

(58) Field of Classification Search
CPC ..... A61B 1/00135; A61B 1/008; A61B 1/051; A61B 2034/301; A61B 2034/306
See application file for complete search history.

(56) References Cited

U.S. PATENT DOCUMENTS

| | | | |
|---|---|---|---|
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |

(56)          References Cited

U.S. PATENT DOCUMENTS

| | | | |
|---|---|---|---|
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,165 B2 | 10/2018 | Power |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |

(56)         References Cited

U.S. PATENT DOCUMENTS

| | | | |
|---|---|---|---|
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 2002/0062063 | A1* | 5/2002 | Ogura .................. A61B 1/0051 |
| | | | 600/141 |
| 2004/0138529 | A1* | 7/2004 | Wiltshire ............. A61B 1/0055 |
| | | | 600/144 |
| 2008/0065097 | A1* | 3/2008 | Duval ...................... A61B 1/06 |
| | | | 606/130 |
| 2009/0248041 | A1 | 10/2009 | Williams et al. |
| 2020/0113645 | A1 | 4/2020 | Genova et al. |

* cited by examiner

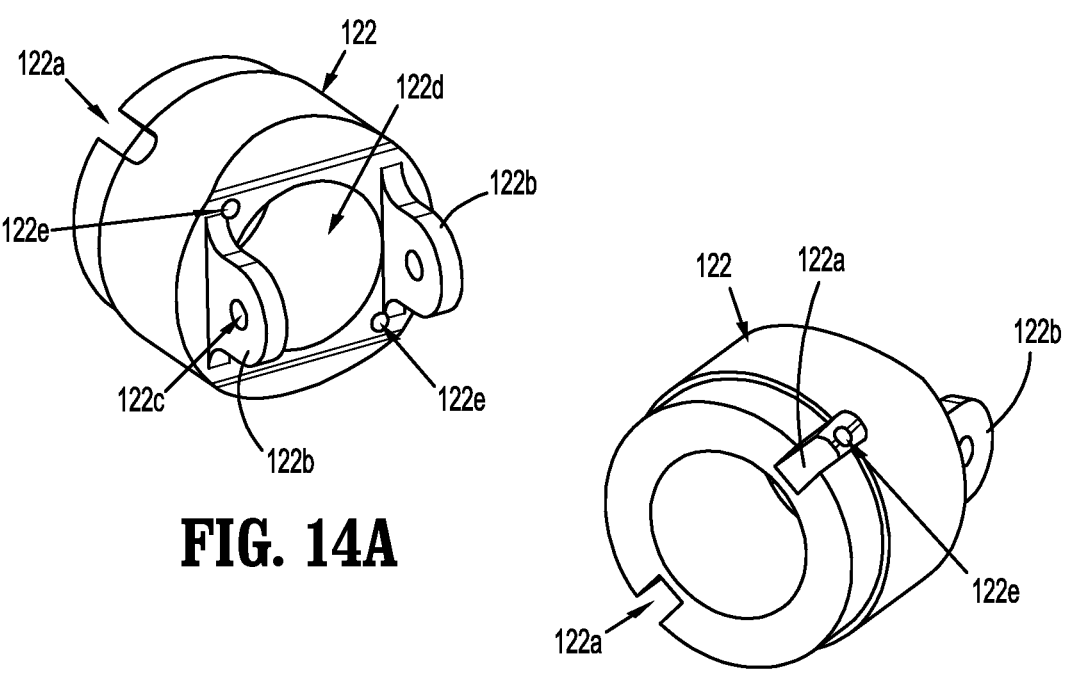
FIG. 14A
FIG. 14B
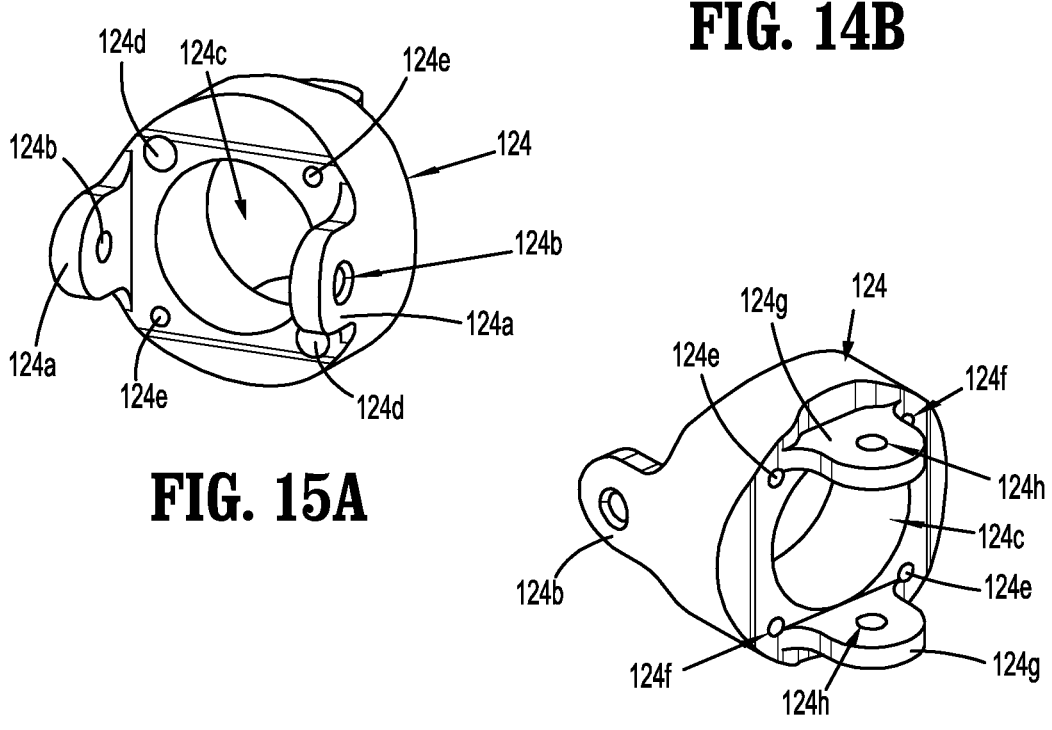
FIG. 15A
FIG. 15B

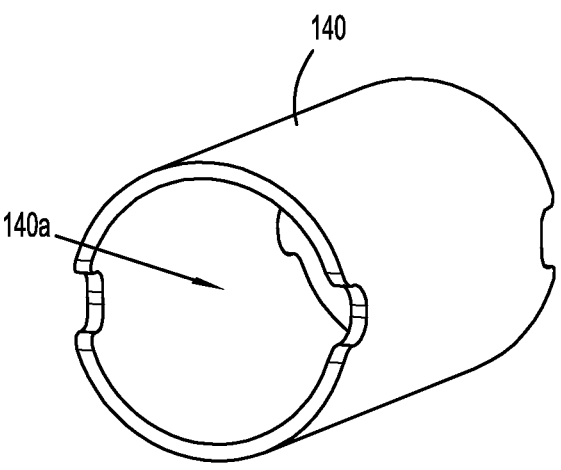
FIG. 18
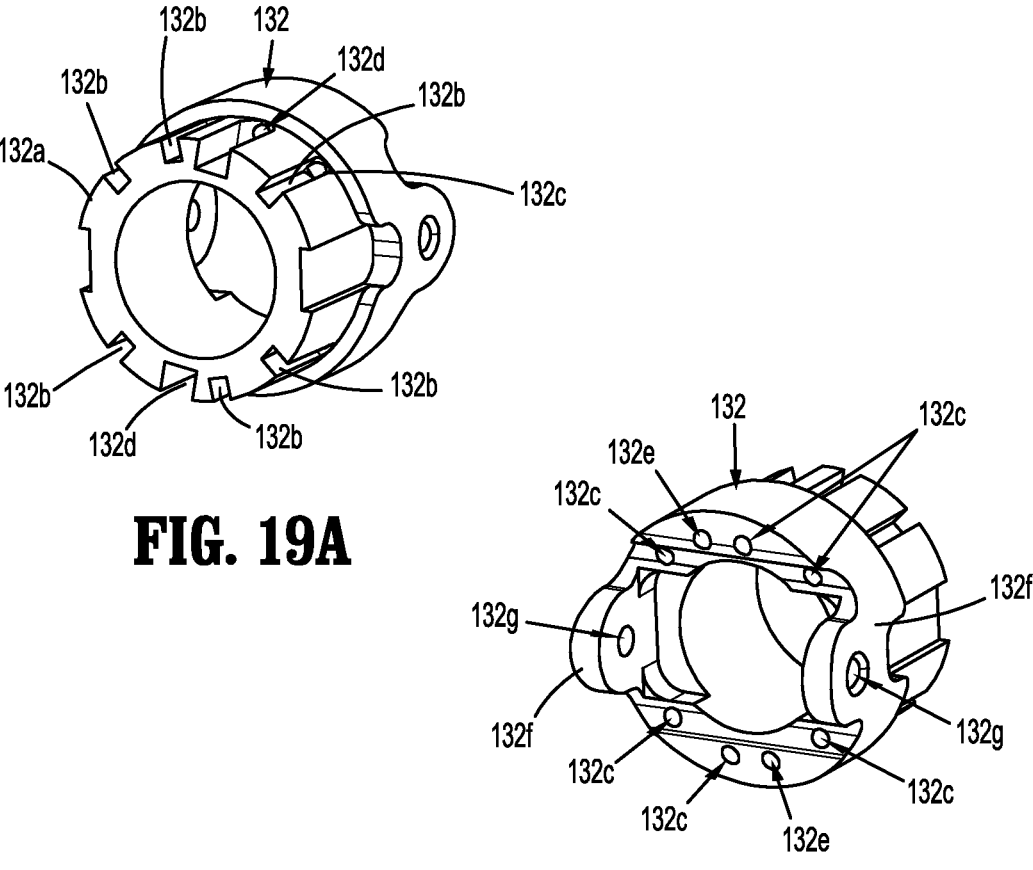
FIG. 19A
FIG. 19B

"P2"

"P3"

"C"

"L2"

299

299

202

200 →

204

206

"L2"

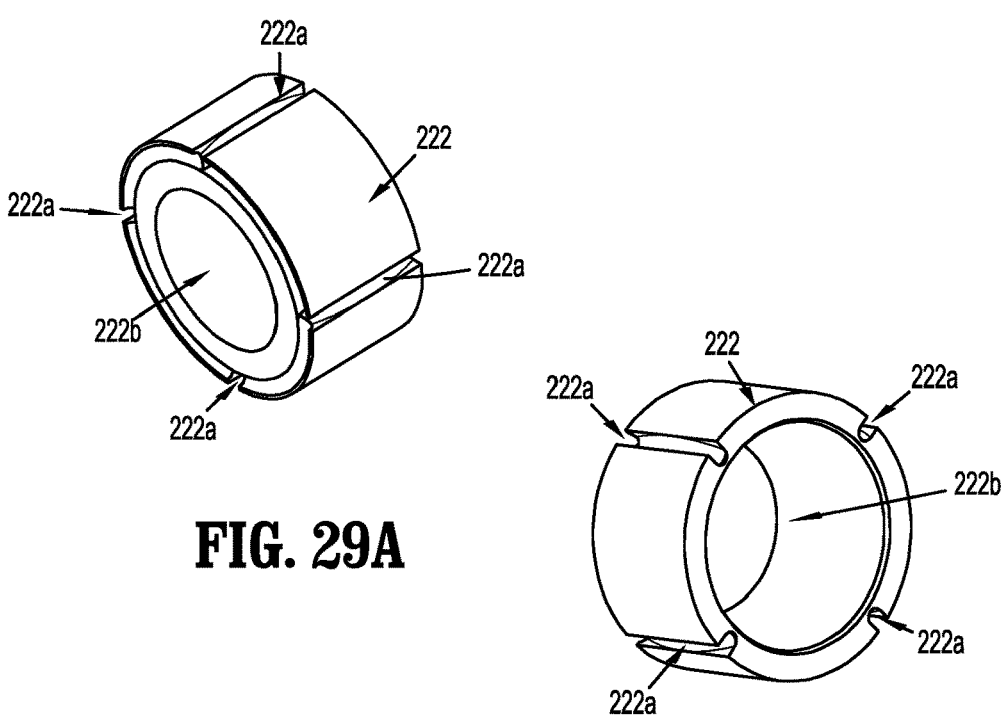
FIG. 29A
FIG. 29B
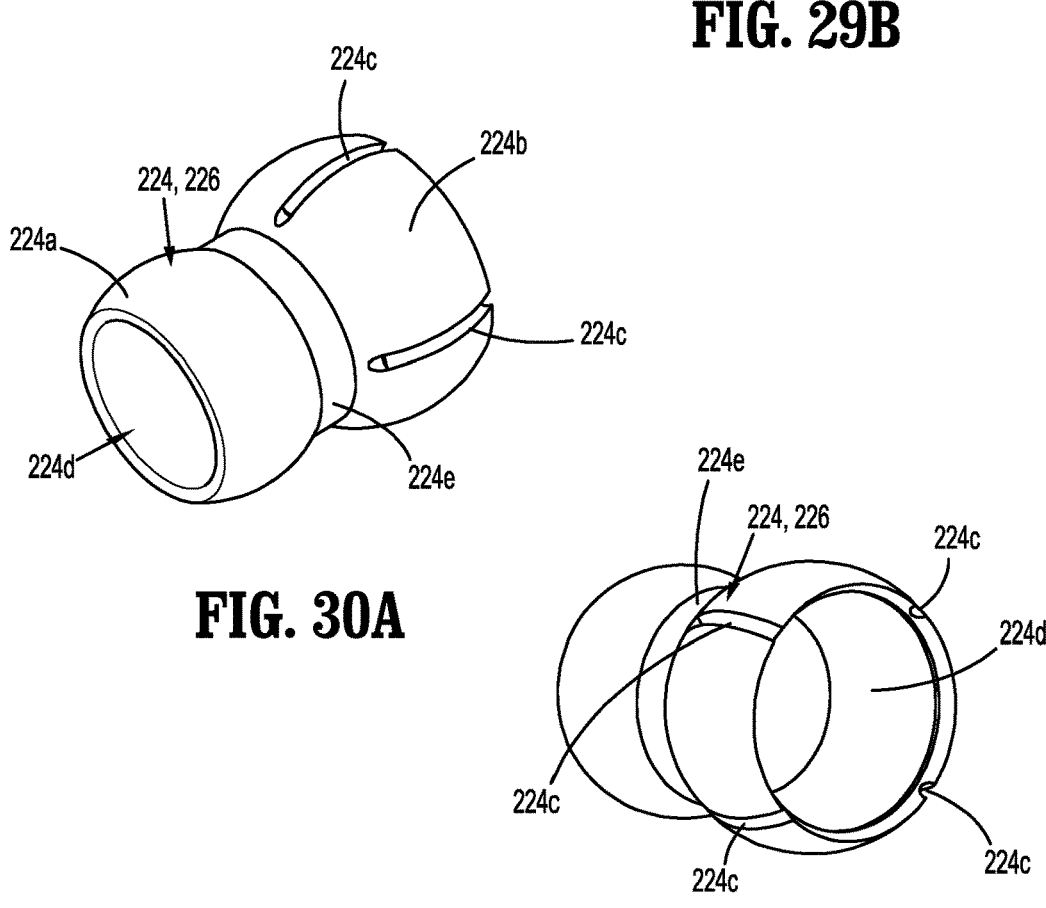
FIG. 30A
FIG. 30B

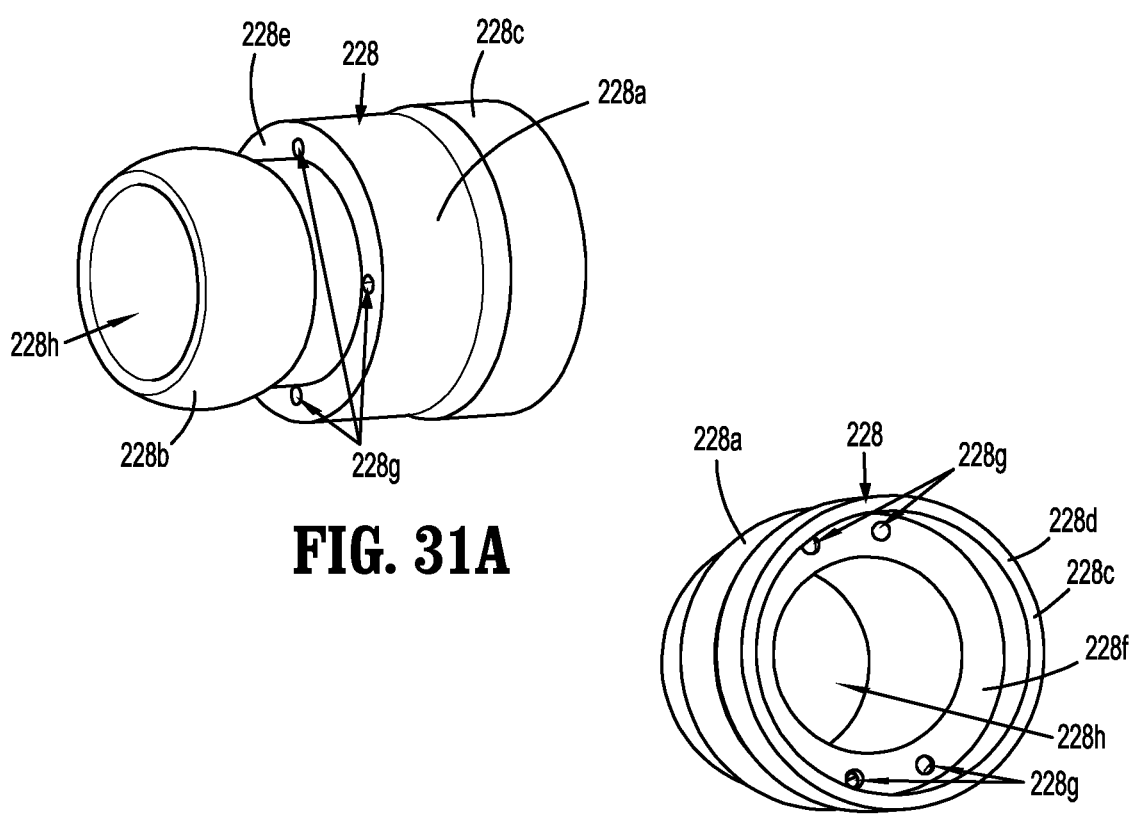
FIG. 31A
FIG. 31B
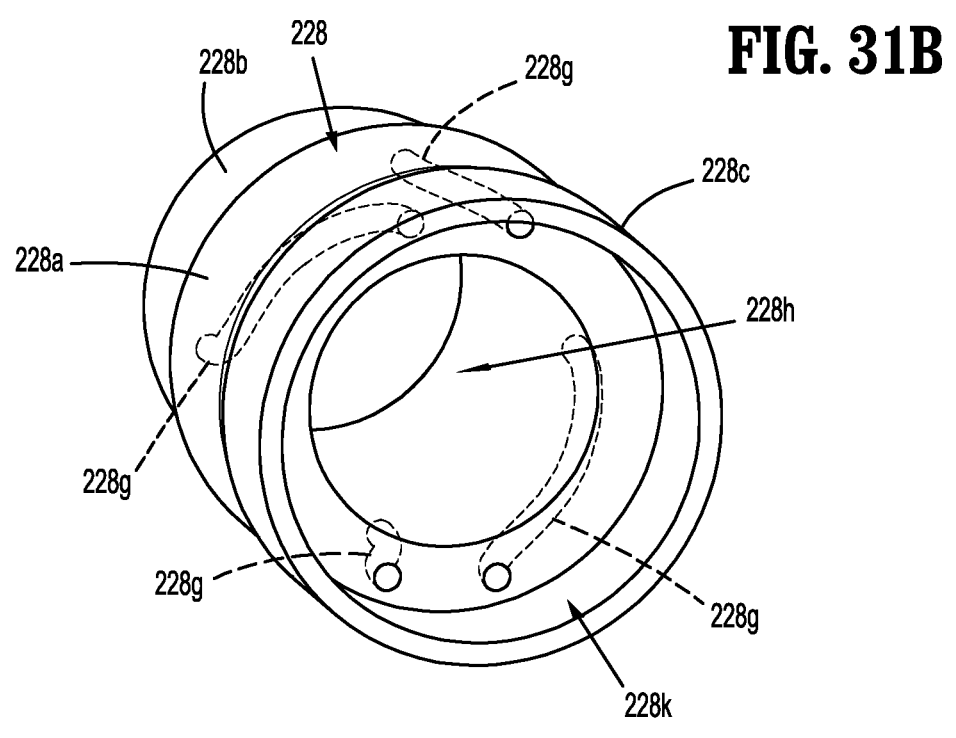
FIG. 31C

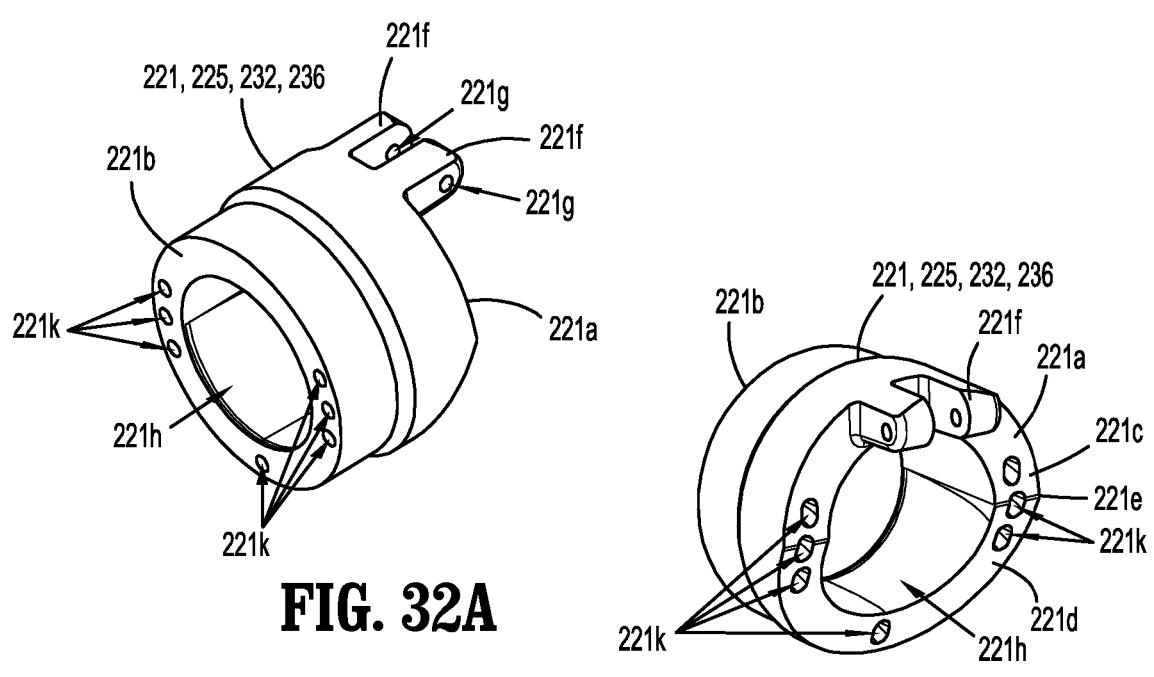
FIG. 32A
FIG. 32B
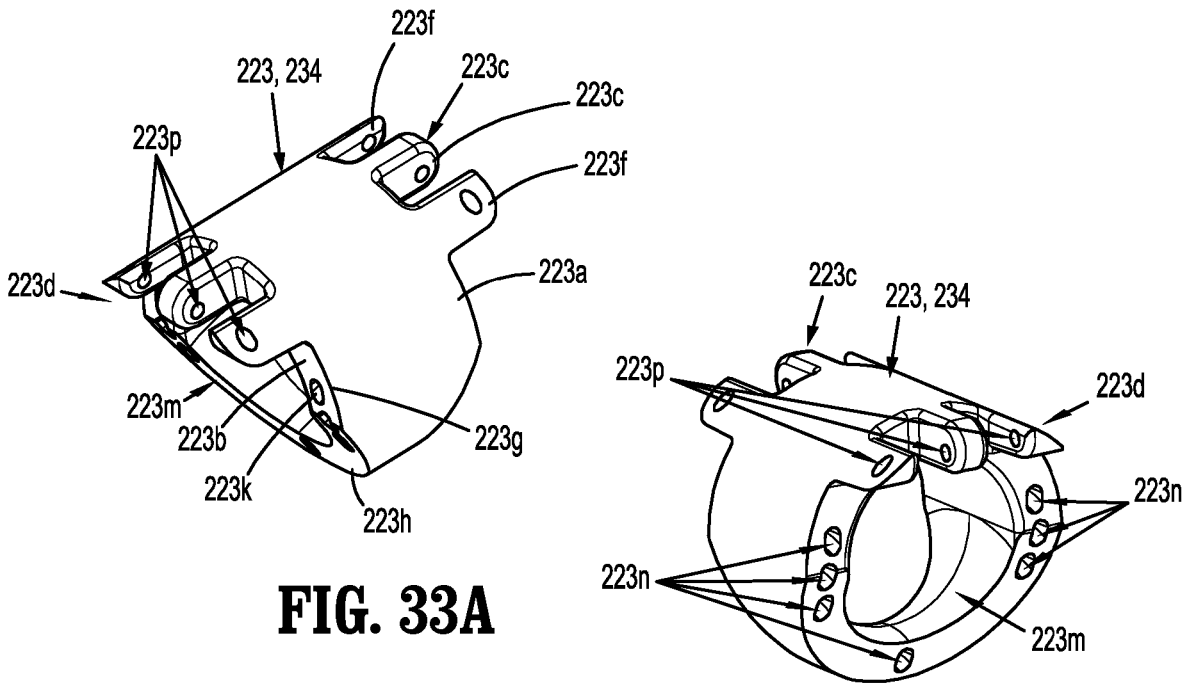
FIG. 33A
FIG. 33B

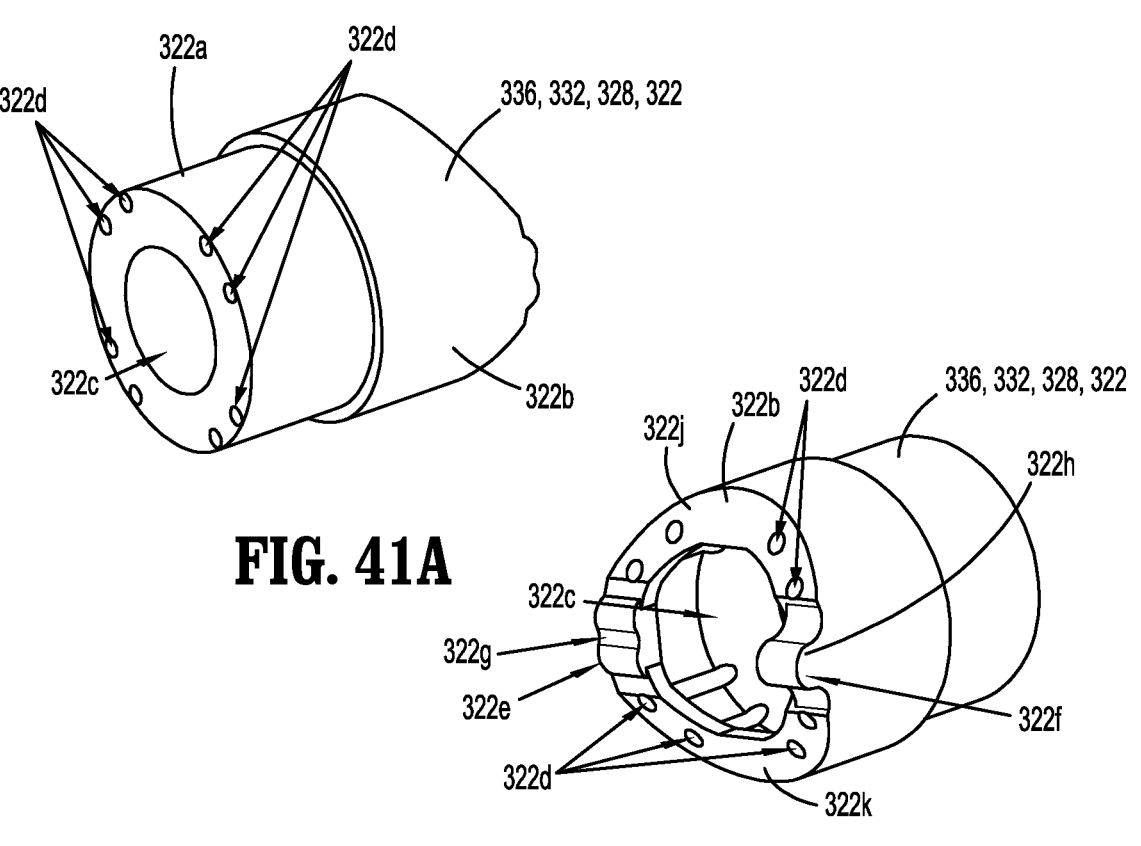
FIG. 41A
FIG. 41B
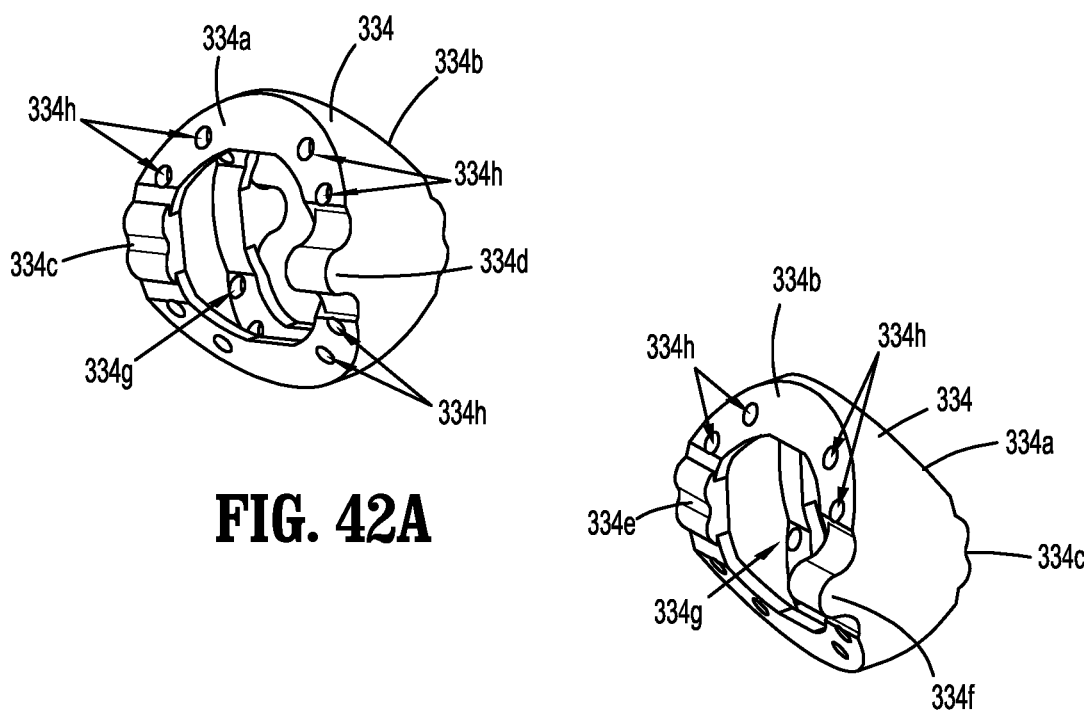
FIG. 42A
FIG. 42B

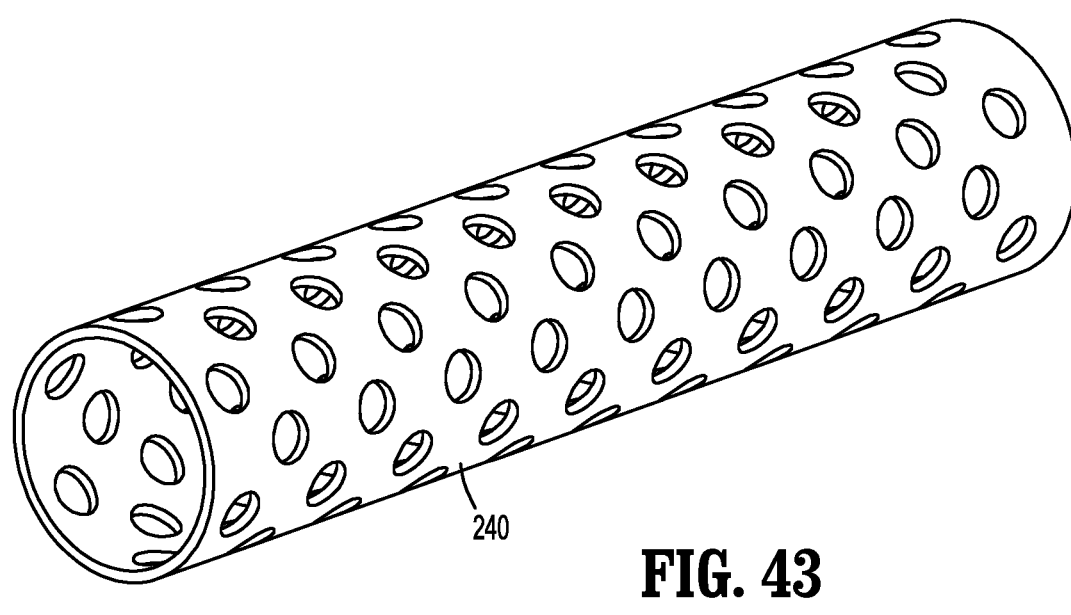
FIG. 43
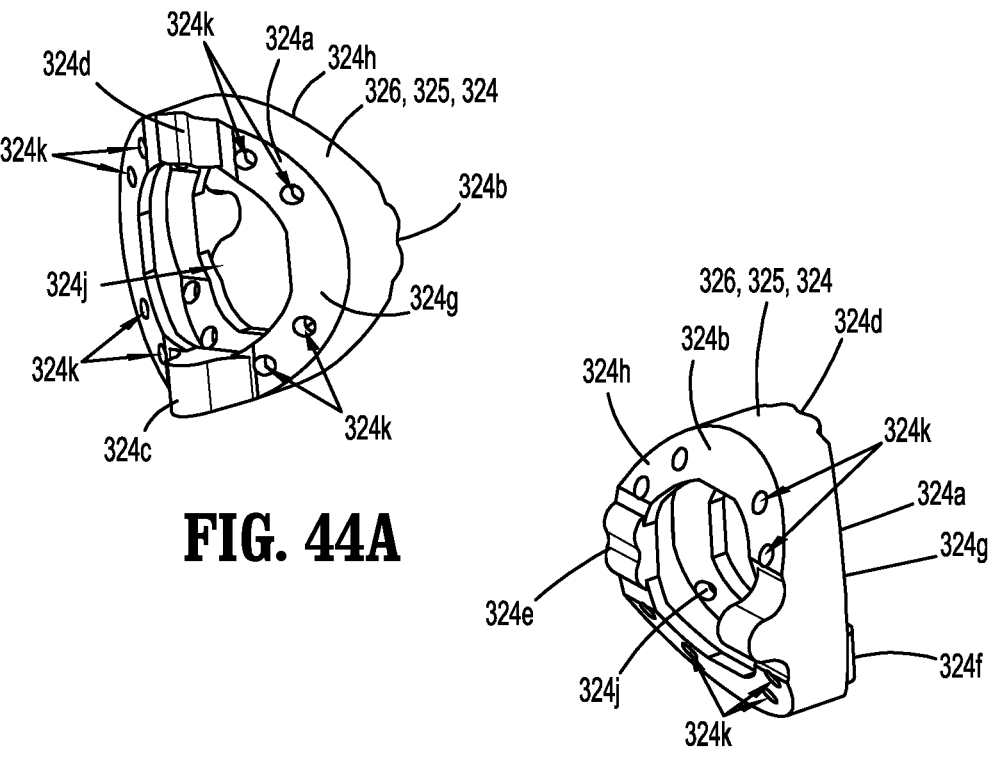
FIG. 44A
FIG. 44B

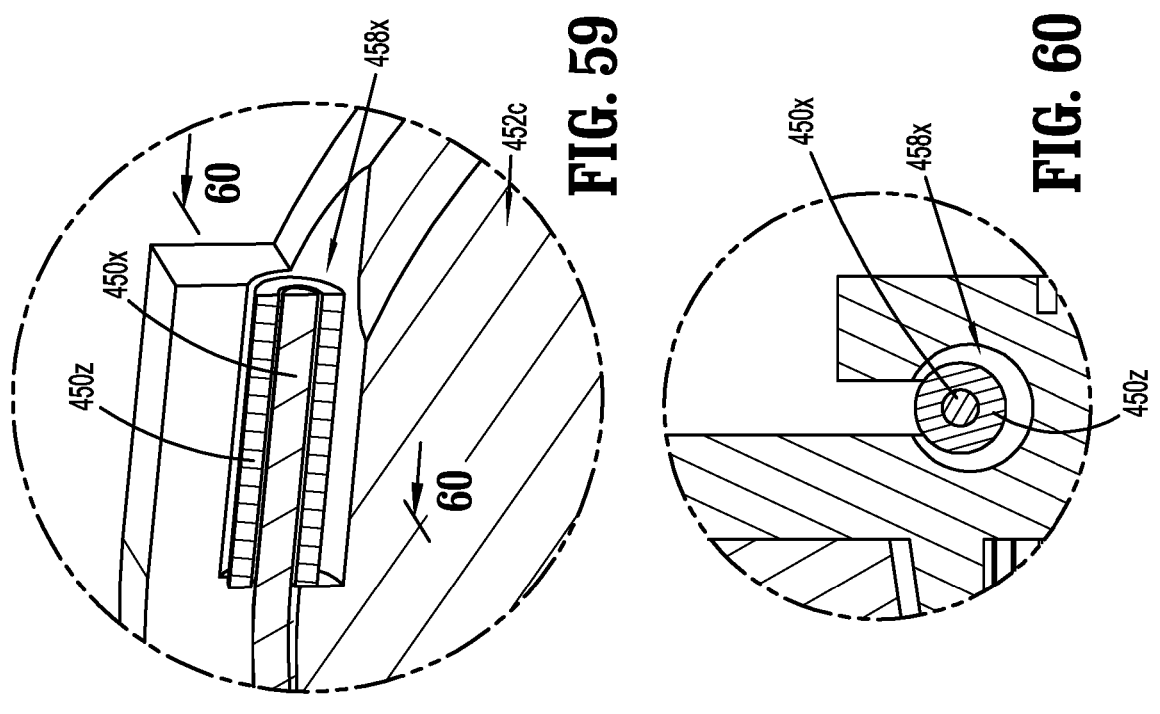
FIG. 59
FIG. 60
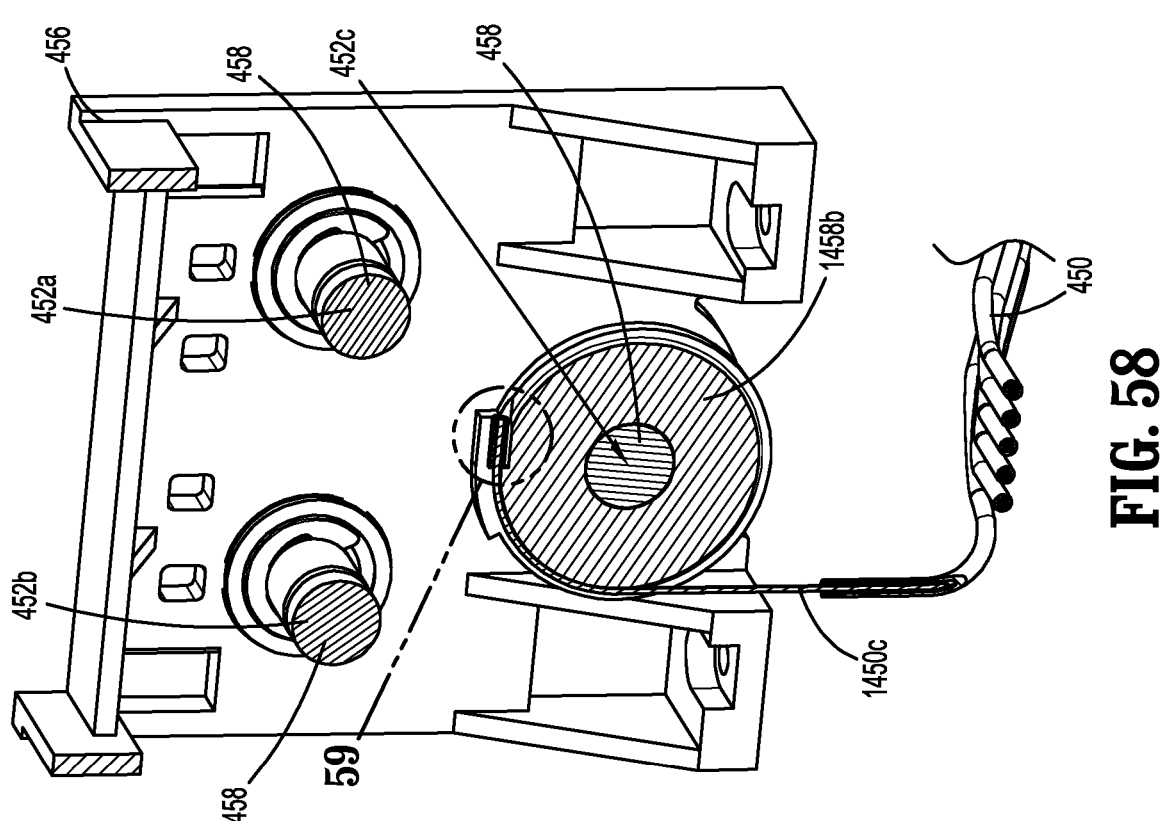
FIG. 58

ROBOTIC SURGICAL SYSTEMS WITH DEXTEROUS ENDOSCOPE

CROSS REFERENCE TO RELATED APPLICATIONS

This application is a U.S. National Stage Application of International Application No. PCT/CA2022/050392, filed Mar. 15, 2022, which claims the benefit of U.S. Provisional Application Ser. No. 63/161,170, filed Mar. 15, 2021, the entire contents of which are incorporated by reference herein.

TECHNICAL FIELD

This disclosure relates to robotic systems and, more particularly, to robotic systems having dexterous endoscopes with robust workspace fields of view.

BACKGROUND

Endoscopes with miniaturized cameras are used during investigative medical procedures and surgical procedures such as laparoscopic surgery to produce images of a site of the procedure within a body cavity of a patient. The camera generally has a field of view that captures only a portion of the body cavity of the patient and may have a positioning mechanism for orienting the camera to change the portion of the body cavity within the field of view.

SUMMARY

In accordance with an aspect of this disclosure, a robotic surgical system includes a drive assembly, an insertion tube, and a dexterous endoscope defining a longitudinal axis and insertable through the insertion tube. The dexterous endoscope is operatively coupled to the drive assembly. The drive assembly is actuatable to manipulate the dexterous endoscope. The dexterous endoscope includes a camera assembly and an articulation assembly. The camera assembly has a compact camera and a sleeve extending proximally from the compact camera module. The articulation assembly supports the compact camera on a distal end portion thereof and is actuatable to move the compact camera relative to the longitudinal axis of the dexterous endoscope. The articulation assembly includes a distal wrist assembly and a proximal wrist assembly that receive the sleeve of the camera assembly therethrough. The distal wrist assembly includes a first plurality of links. The links of the first plurality of links are movable relative to one another. The proximal wrist assembly includes a second plurality of links. The links of the second plurality of links are movable relative to one another.

In aspects, the first plurality of links may be pinned together.

In aspects, the second plurality of links may be pinned together.

In aspects, the articulation assembly may include a plurality of articulation cables that extends through at least some links of the first plurality of links. The plurality of articulation cables may extend through at least some links of the second plurality of links. At least some articulation cables of the plurality of articulation cables may be coupled to at least one link of the second plurality of links by ferrules. At least some articulation cables of the plurality of articulation cables may be coupled to at least one link of the first plurality of links by ferrules.

In aspects, at least some links of the first and second plurality of links may define cable passages therethrough for supporting the plurality of articulation cables.

In aspects, the first plurality of links may include a distal head link engaged with the compact camera module, a distal link that is pivotably coupled to the distal head link, an intermediate link that is pivotably coupled to the distal link, and a proximal link that is pivotably coupled to the intermediate link and frictionally engaged with a distal end portion of the connector tube. The second plurality of links may include a distal link frictionally engaged with a proximal end portion of the connector tube, an intermediate link pivotably coupled to the distal link of the second plurality of links, and a proximal link pivotably coupled to the intermediate link of the second plurality of links.

In accordance with another aspect of this disclosure, a surgical system includes an insertion tube, a first surgical instrument, and a dexterous endoscope. The insertion tube defines a plurality of conduits therethrough. The first surgical instrument is insertable through a first one of the plurality of conduits. The dexterous endoscope defines a longitudinal axis and is insertable through a second one of the plurality of conduits. The dexterous endoscope includes a camera assembly and an articulation assembly. The articulation assembly supports the camera assembly and is actuatable to pan, tilt, and/or elevate the camera assembly relative to the longitudinal axis. The articulation assembly includes a distal wrist assembly and a proximal wrist assembly that are longitudinally spaced apart by a connector tube. The distal and proximal wrist assemblies are movable relative to one another and the connector tube.

In aspects, the surgical system includes a second surgical instrument that may be insertable through a third one of the plurality of conduits and a third surgical instrument that may be insertable through a fourth one of the plurality of conduits, wherein the dexterous endoscope, the first instrument, the second instrument, and the third instrument may be simultaneously positionable within the four separate conduits.

In aspects, the distal wrist assembly may include a first plurality of links. The links of the first plurality of links may be movable relative to one another. The proximal wrist assembly may include a second plurality of links. The links of the second plurality of links may be movable relative to one another. The first plurality of links may be pinned together. The second plurality of links may be pinned together.

In aspects, the articulation assembly may include a plurality of articulation cables that extends through at least some links of the first plurality of links. The plurality of articulation cables may extend through at least some links of the second plurality of links. At least some articulation cables of the plurality of articulation cables may be coupled to at least one link of the second plurality of links by ferrules. At least some articulation cables of the plurality of articulation cables may be coupled to at least one link of the first plurality of links by ferrules.

According to yet another aspect, this disclosure is directed to a surgical system including a drive assembly and a dexterous endoscope defining a longitudinal axis. The dexterous endoscope actuatable by the drive assembly and including a camera assembly and an articulation assembly. The articulation assembly supports the camera assembly and is actuatable to pan, tilt, and/or elevate the camera assembly relative to the longitudinal axis. The articulation assembly includes a distal wrist assembly and a proximal wrist assembly that are coupled together by a plurality of articulation cables. The distal wrist assembly includes a first plurality of links. The links of the first plurality of links are movable relative to one another. The proximal wrist assembly includes a second plurality of links. The links of the second plurality of links are movable relative to one another. The first plurality of links includes at least three links pinned together and the second plurality of links includes at least three links pinned together.

According to one aspect, this disclosure is directed to a robotic surgical system. The robotic surgical system includes a drive assembly and a dexterous endoscope operatively coupled to the drive assembly and defining a longitudinal axis. The dexterous endoscope includes a camera assembly and an articulation assembly supporting the camera assembly on a distal end portion thereof. The articulation assembly is actuatable by the drive assembly. The articulation assembly includes a ball joint assembly, a first pin joint assembly, and a second pin joint assembly that are movable relative to one another to articulate the camera assembly relative to the longitudinal axis of the dexterous endoscope.

In aspects, the first pin joint assembly may be disposed proximal to the ball joint assembly and distal to the second pin joint assembly.

In aspects, the robotic surgical system may further comprise a connector tube that separates the first pin joint assembly and the second pin joint assembly.

In aspects, the ball joint assembly may include a first plurality of links. The first plurality of links may include a distal ball joint link, an intermediate ball joint link disposed proximal to the distal ball joint link, and a proximal ball joint link that is disposed proximal to the intermediate ball joint link.

In aspects, the robotic surgical system may further comprise a distal head link coupled to a distal end portion of the distal ball joint link. The distal head link may be positioned to support the camera assembly.

In aspects, the first pin joint assembly may include a second plurality of links. The second plurality of links may include a first distal pin joint, a first intermediate pin joint disposed proximal to the first distal pin joint, and a first proximal pin joint, the first proximal pin joint disposed proximal to the first intermediate pin joint.

In aspects, the second pin joint assembly may include a third plurality links. The third plurality of links may include a second distal pin joint, a second intermediate pin joint disposed proximal to the second distal pin joint, and a second proximal pin joint, the second proximal pin joint disposed proximal to the second intermediate pin joint.

According to a further aspect, this disclosure is directed to a surgical system. The surgical system includes an insertion tube defining a plurality of conduits therethrough, a first surgical instrument insertable through a first one of the plurality of conduits, and a dexterous endoscope defining a longitudinal axis and insertable through a second one of the plurality of conduits. The dexterous endoscope includes a camera assembly and an articulation assembly supporting the camera assembly. The articulation assembly is actuatable to pan, tilt, and/or elevate the camera assembly relative to the longitudinal axis. The articulation assembly includes a ball joint assembly, a first pin joint assembly, and a second pin joint assembly that are movable relative to one another.

According to still another aspect, this disclosure is directed to a surgical system. The surgical system includes a drive assembly and a dexterous endoscope. The dexterous endoscope defines a longitudinal axis and is actuatable by the drive assembly. The dexterous endoscope includes a camera assembly and an articulation assembly supporting the camera assembly. The articulation assembly is actuatable to pan, tilt, and/or elevate the camera assembly relative to the longitudinal axis. The articulation assembly includes a distal wrist assembly and a proximal wrist assembly that are coupled together by a plurality of articulation cables. The distal wrist assembly includes a ball joint assembly and a first pin joint assembly that are movable relative to one another. The proximal wrist assembly includes a plurality of joints pinned together.

In accordance with one aspect, this disclosure is directed to a robotic surgical system comprising a drive assembly and a dexterous endoscope operatively coupled to the drive assembly. The dexterous endoscope defines a longitudinal axis and includes a camera assembly and an articulation assembly. The articulation assembly supports the camera assembly on a distal end portion thereof and is actuatable by the drive assembly. The articulation assembly includes a first wrist assembly having a plurality of vertebral links. The vertebral links of the plurality of vertebral links are pivotable relative to one another to articulate the camera assembly relative to the longitudinal axis of the dexterous endoscope.

In aspects, the robotic surgical system may further comprise a second wrist assembly having a plurality of links. The links of the plurality of links of the second wrist assembly may be pivotable relative to one another.

In aspects, each vertebral link of the plurality of vertebral links may include a tooth segment and a groove segment. The tooth segment and the groove segment may be disposed on diametrically opposed sides of each respective vertebral link.

In aspects, a plurality of articulation cables may be coupled to the plurality of vertebral links. The plurality of articulation cables may be actuatable to move the vertebral links of the plurality of vertebral links relative to one another.

In aspects, at least some of the plurality of vertebral links may define cable passages therethrough that slidably receive the plurality of articulation cables. The plurality of articulation cables supports ferrules that secure the plurality of articulation cables to at least one vertebral link of the plurality of vertebral links.

In aspects, the plurality of vertebral links may include a first distal vertebral link, a first intermediate vertebral link rotationally offset from the first distal vertebral link, and a first proximal vertebral link rotationally offset from the first intermediate vertebral link.

In aspects, the robotic surgical system may further comprise a first distal head link pivotably coupled to the first distal vertebral link and a first proximal tail link pivotably coupled to the first proximal vertebral link. The first distal head link may support the camera assembly.

In aspects, the second wrist assembly may be proximal to the first wrist assembly. The plurality of links of the second wrist assembly may include a second distal head link, a second intermediate vertebral link pivotably coupled to the second distal head link, and a second proximal tail link pivotably coupled to the second intermediate vertebral link.

According to another aspect, a surgical system includes an insertion tube defining a plurality of conduits therethrough, a first surgical instrument insertable through a first one of the plurality of conduits, and a dexterous endoscope defining a longitudinal axis and insertable through a second one of the plurality of conduits. The dexterous endoscope includes a camera assembly and an articulation assembly supporting the camera assembly. The articulation assembly is actuatable to pan, tilt, and/or elevate the camera assembly relative to the longitudinal axis. The articulation assembly includes a first wrist assembly, a second wrist assembly, and a connector tube that couples the first and second wrist assemblies together. The first wrist assembly includes a plurality of vertebral links. The vertebral links of the plurality of vertebral links are pivotably coupled to one another.

According to still another aspect, this disclosure is directed to a surgical system comprising a drive assembly and a dexterous endoscope defining a longitudinal axis. The dexterous endoscope is actuatable by the drive assembly and includes a camera assembly and an articulation assembly supporting the camera assembly. The articulation assembly is actuatable to pan, tilt, and/or elevate the camera assembly relative to the longitudinal axis. The articulation assembly includes a distal wrist assembly and a proximal wrist assembly that are coupled together by a plurality of articulation cables and a connector tube. The distal wrist assembly includes at least one vertebral link, and the proximal wrist assembly includes at least one vertebral link.

According to yet another aspect, this disclosure is directed to a surgical system. The surgical system includes a drive assembly and a dexterous endoscope defining a longitudinal axis. The dexterous endoscope is actuatable by the drive assembly and includes a camera assembly and a drive mechanism. The drive mechanism is operatively coupled to the drive assembly. The drive mechanism includes a cable assembly and a drive train assembly that is operatively coupled to the cable assembly. The drive train assembly is actuatable to manipulate the cable assembly, wherein manipulation of the cable assembly causes the camera assembly to pan up to 45 degrees relative to the longitudinal axis, tilt up to 68 degrees relative to the longitudinal axis, or elevate up to 68 degrees relative to the longitudinal axis.

In aspects, the drive mechanism may include a pan drive train that is rotatable to cause panning movement of the camera assembly. The drive mechanism may include a tilt drive train that is rotatable to cause tilting movement of the camera assembly. The drive mechanism may include an elevate drive train that is rotatable to cause the camera assembly to elevate or descend relative to the longitudinal axis. At least one of the elevate drive train or the tilt drive train may include an elongated lengthener hub having a non-circular cross section. The elongated lengthener hub may extend to an apex.

In aspects, the elevate drive train may extend to a first apex and the tilt drive train may extend to a second apex. The first apex may extend to a first radial distance from a first longitudinal axis of the elevate drive train, the second apex may extend to a second radial distance from a second longitudinal axis of the tilt drive train. The second radial distance may be different from the first radial distance.

In aspects, the pan drive train may include a hub having a circular cross section.

According to a further aspect, this disclosure is directed to a surgical system including an insertion tube defining a plurality of conduits therethrough, a first surgical instrument insertable through a first one of the plurality of conduits, and a dexterous endoscope defining a longitudinal axis and insertable through a second one of the plurality of conduits. The dexterous endoscope is movable between articulated and unarticulated positions relative to the longitudinal axis and includes a camera assembly and a drive mechanism. The drive mechanism includes a cable assembly and a drive train assembly that is operatively coupled to the cable assembly. The drive train assembly is actuatable to manipulate the cable assembly, wherein the drive train assembly includes at least one elongated lengthener hub having a non-circular cross-section around which the cable assembly winds. The at least one elongated lengthener hub is configured to maintain constant cable tension in the cable assembly as the dexterous endoscope moves between the articulated and unarticulated positions relative to the longitudinal axis.

According to one aspect, this disclosure is directed to a robotic surgical system including a drive assembly and a dexterous endoscope operatively coupled to the drive assembly. The dexterous endoscope defines a longitudinal axis and includes a camera assembly and a robotically controlled drive mechanism. The drive assembly includes a cable assembly and a drive train assembly that is operatively coupled to the cable assembly. The drive train assembly is actuatable to manipulate the cable assembly, wherein manipulation of the cable assembly causes the camera assembly to pan up to 45 degrees relative to the longitudinal axis, tilt up to 68 degrees relative to the longitudinal axis, or elevate up to 68 degrees relative to the longitudinal axis.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, explain the principles of this disclosure, wherein:

FIGS. 14A-21B show various enlarged, front and rear perspective views of links of the distal portion shown in FIGS. 12 and 13;

Figure 1:
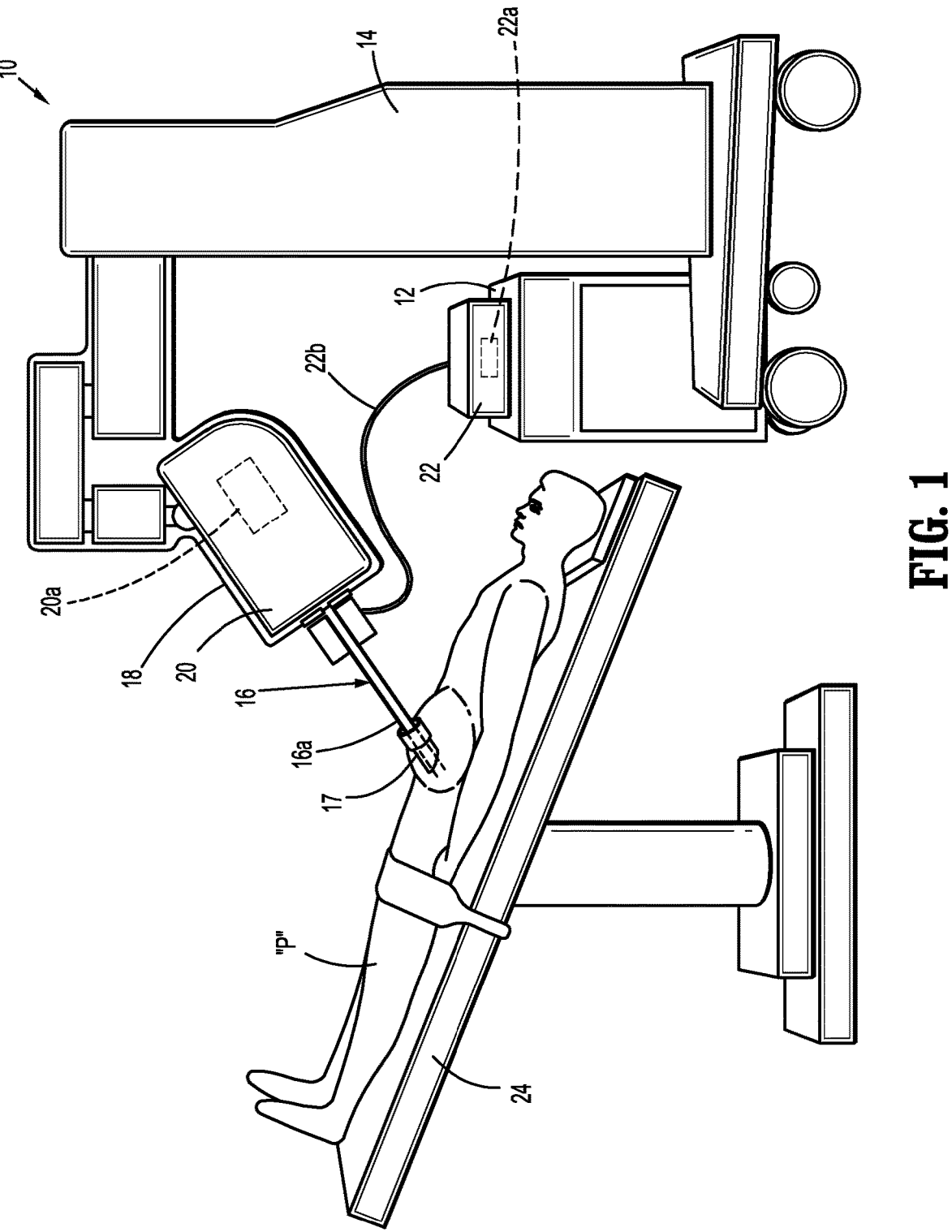
FIG. 1 is a perspective view of a robotic surgical system being used for a surgical procedure on a patient in accordance with the principles of this disclosure.
Figure 2:
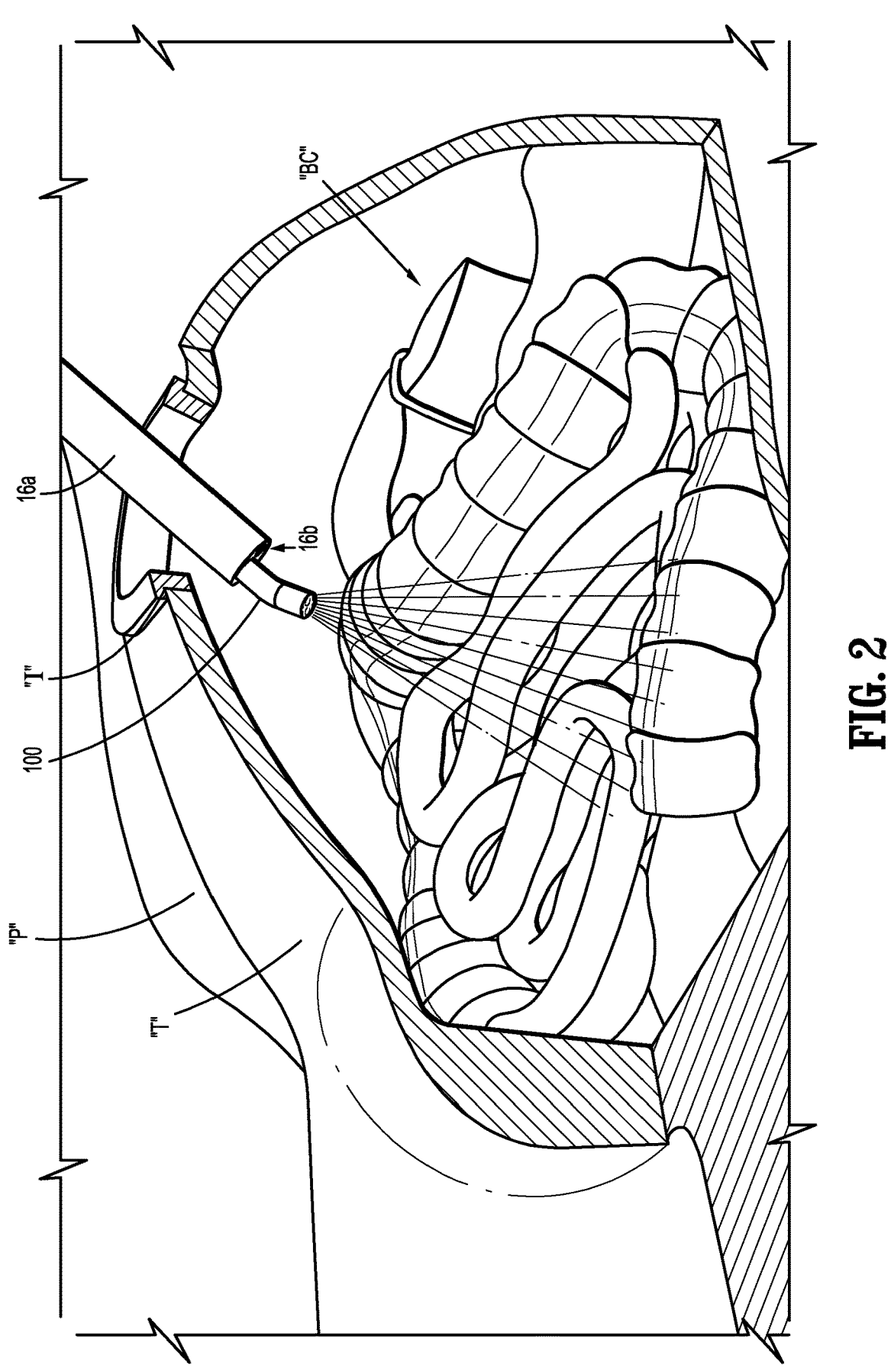
FIGS. 2-4 are progressive views illustrating one endoscopic system of the robotic surgical system of FIG. 1 being manipulated within a body cavity of the patient.
Figure 3:
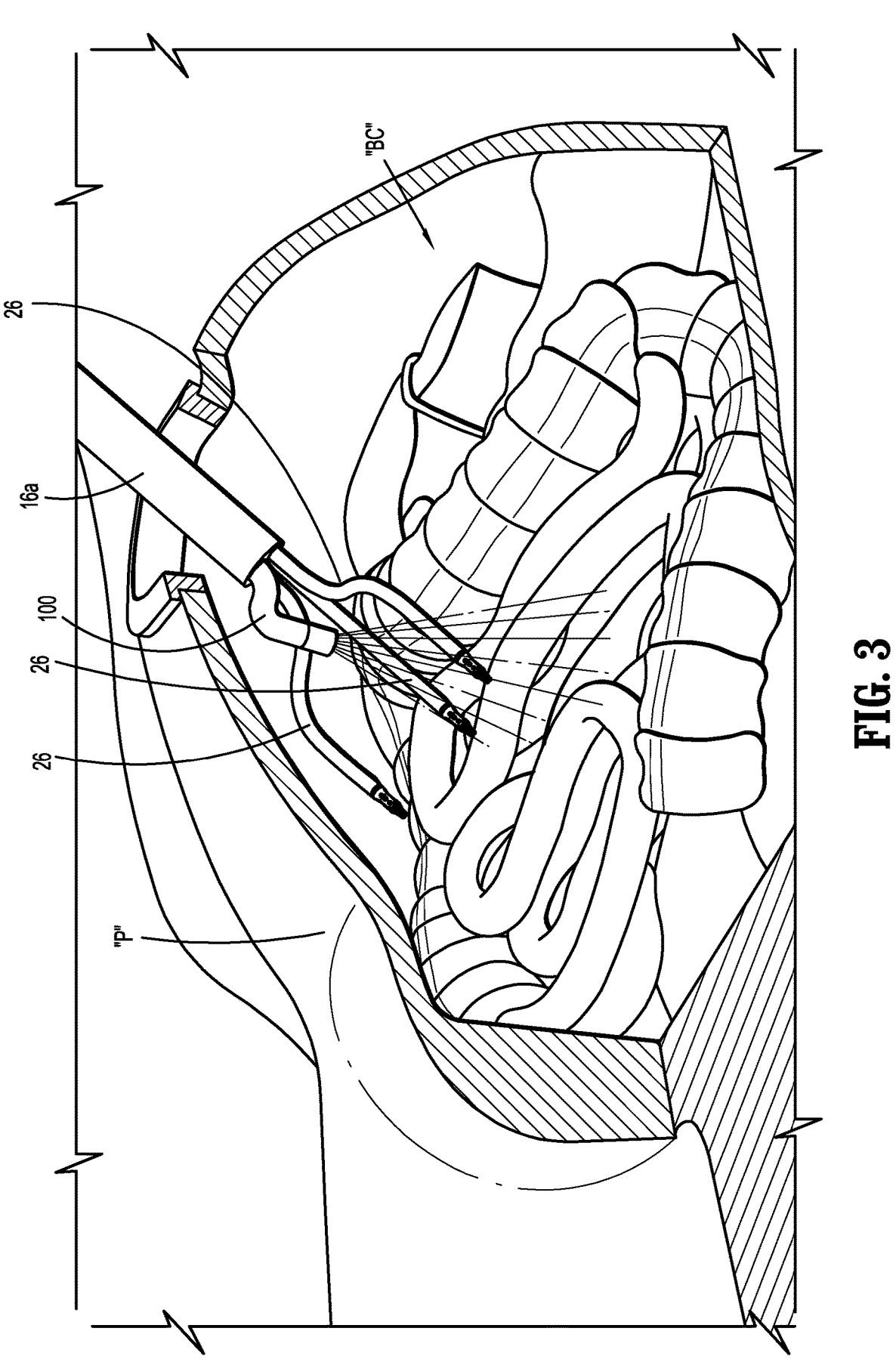
Figure 4:
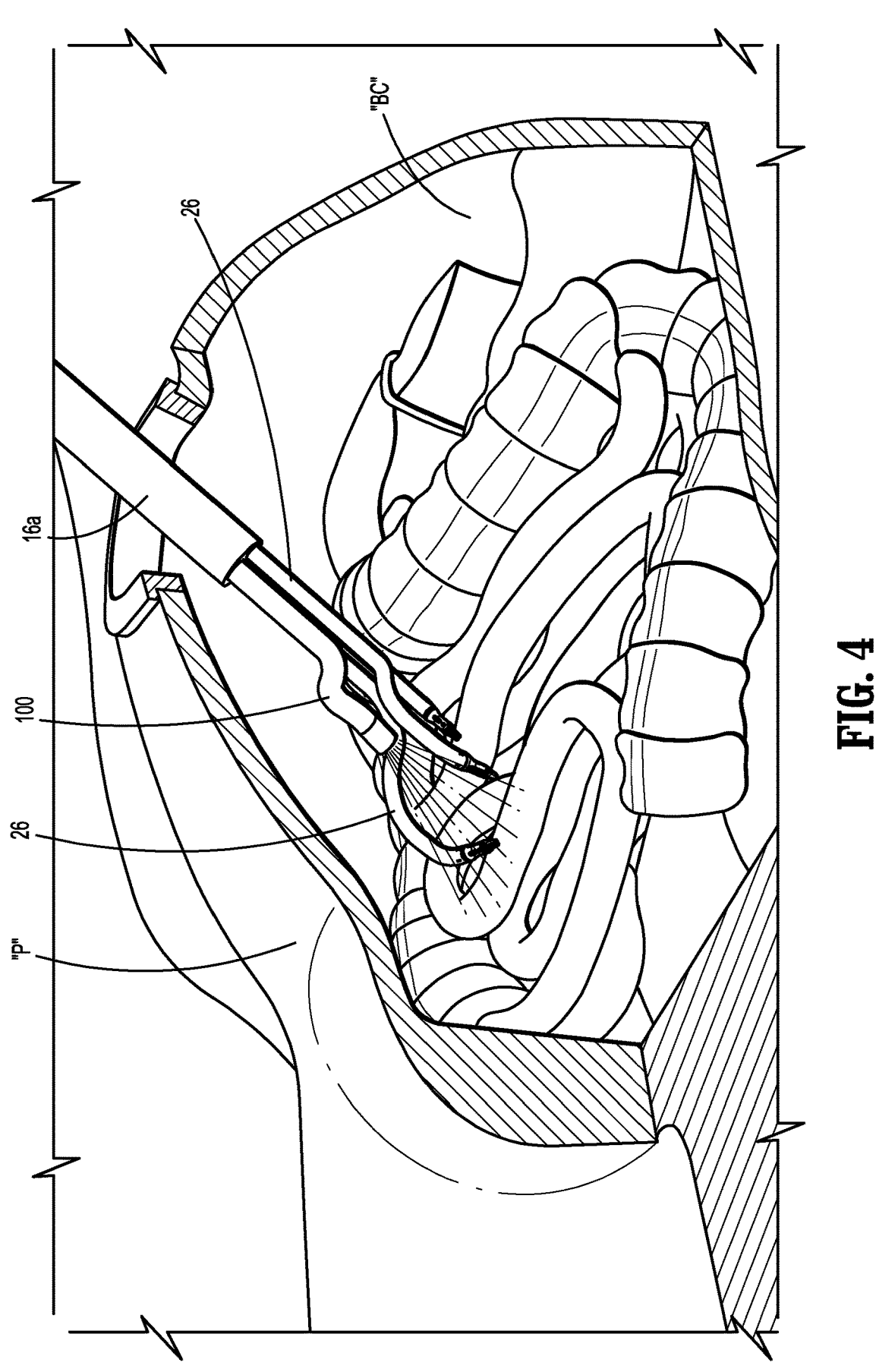
Figure 5:
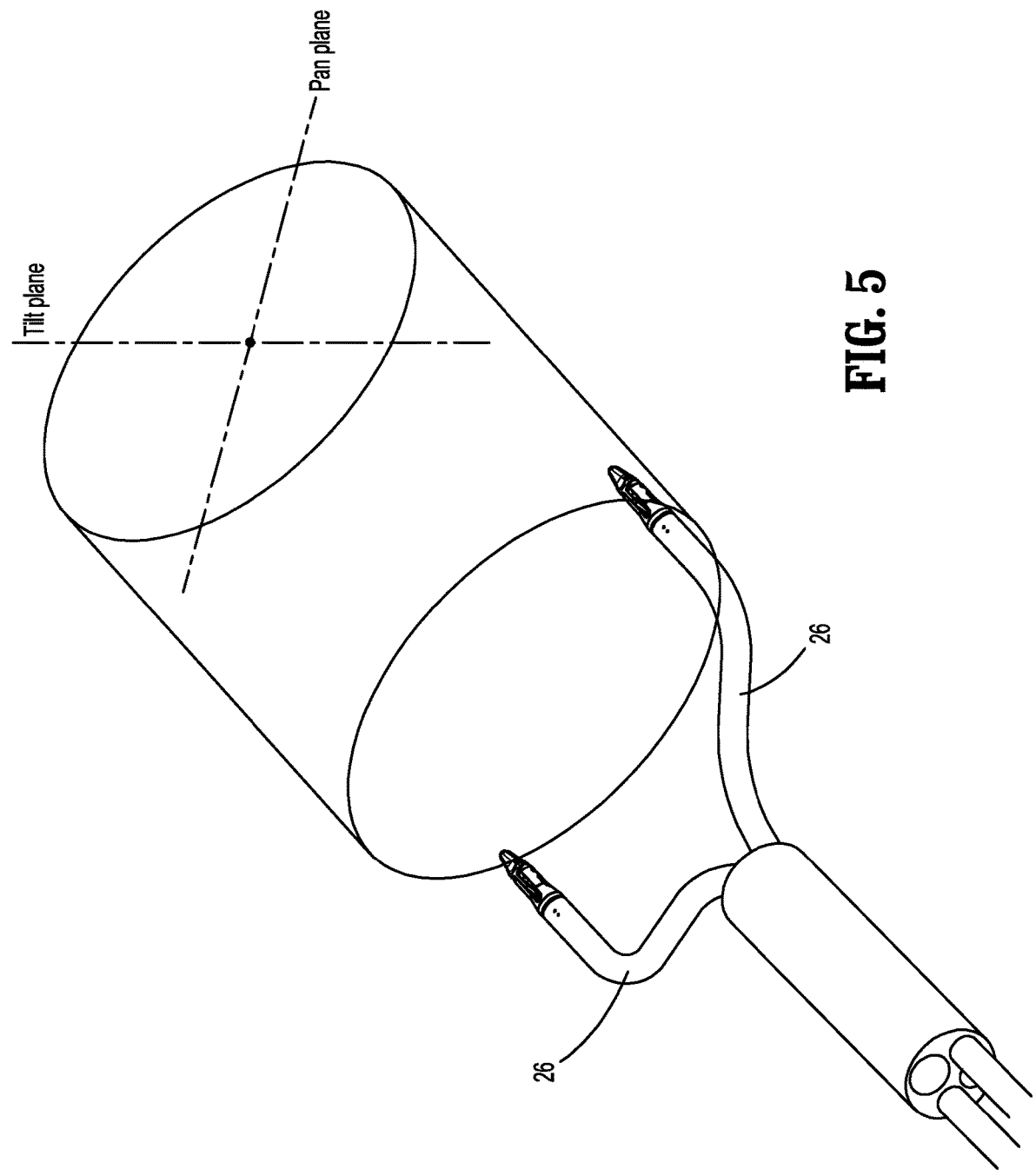
FIGS. 5-7 are various views of a distal portion of the endoscopic system of FIGS. 2-4 shown relative to a workspace field of view.
Figure 26:
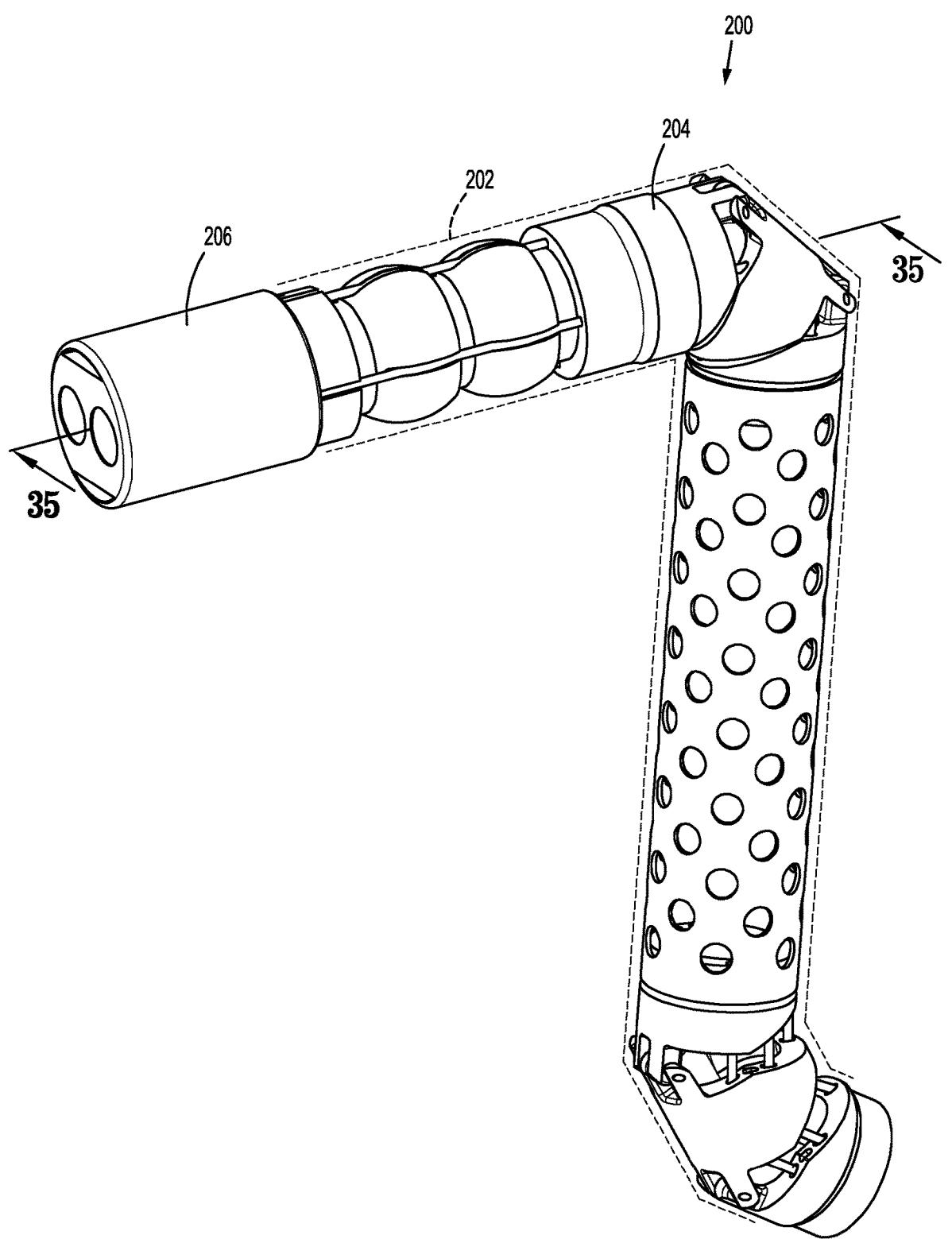
FIG. 26 is a perspective view of a distal portion of another dexterous endoscope of the robotic surgical system of FIG.
Figure 27:
Figure 28:
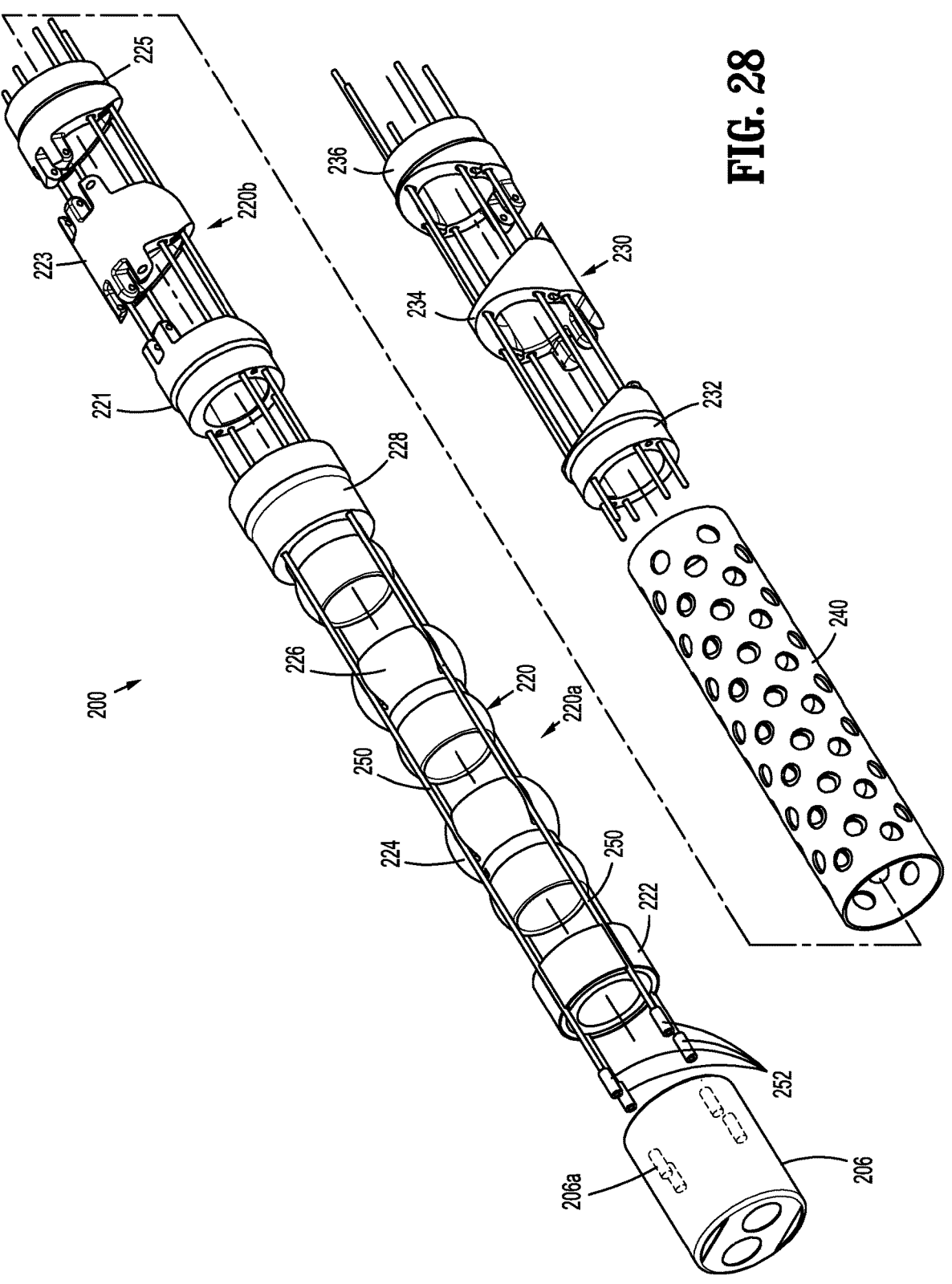
Figure 34:
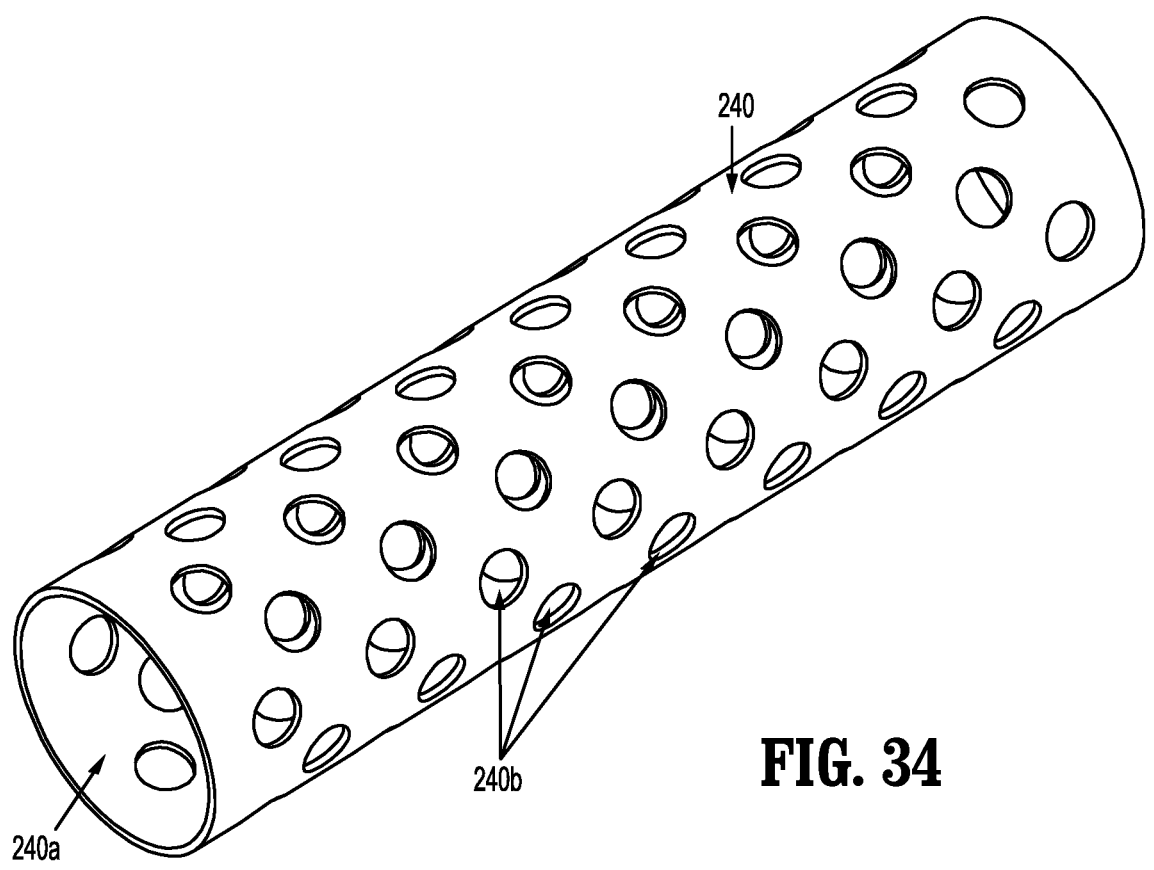
Figure 35:
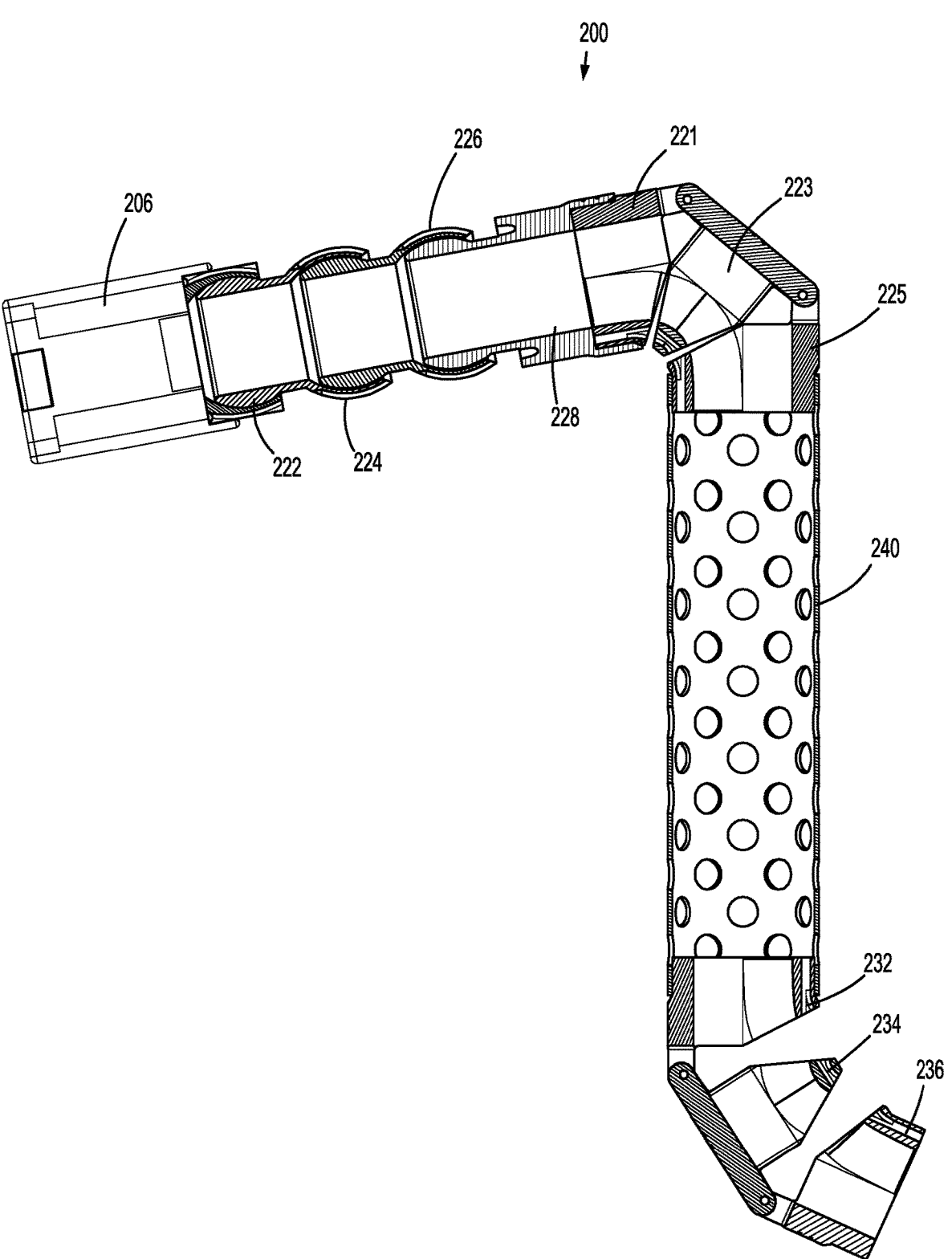
Figure 36:
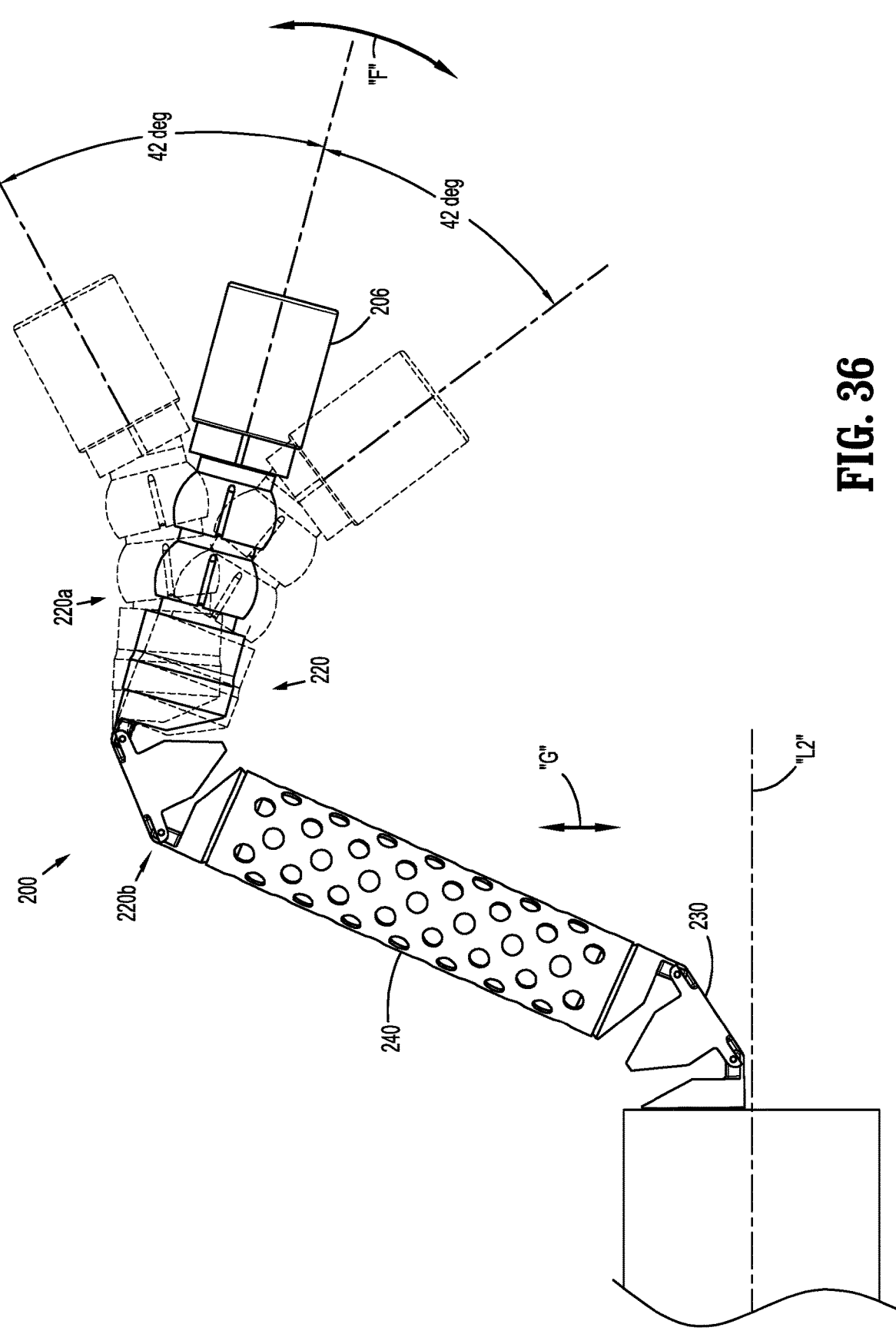
Figure 37:
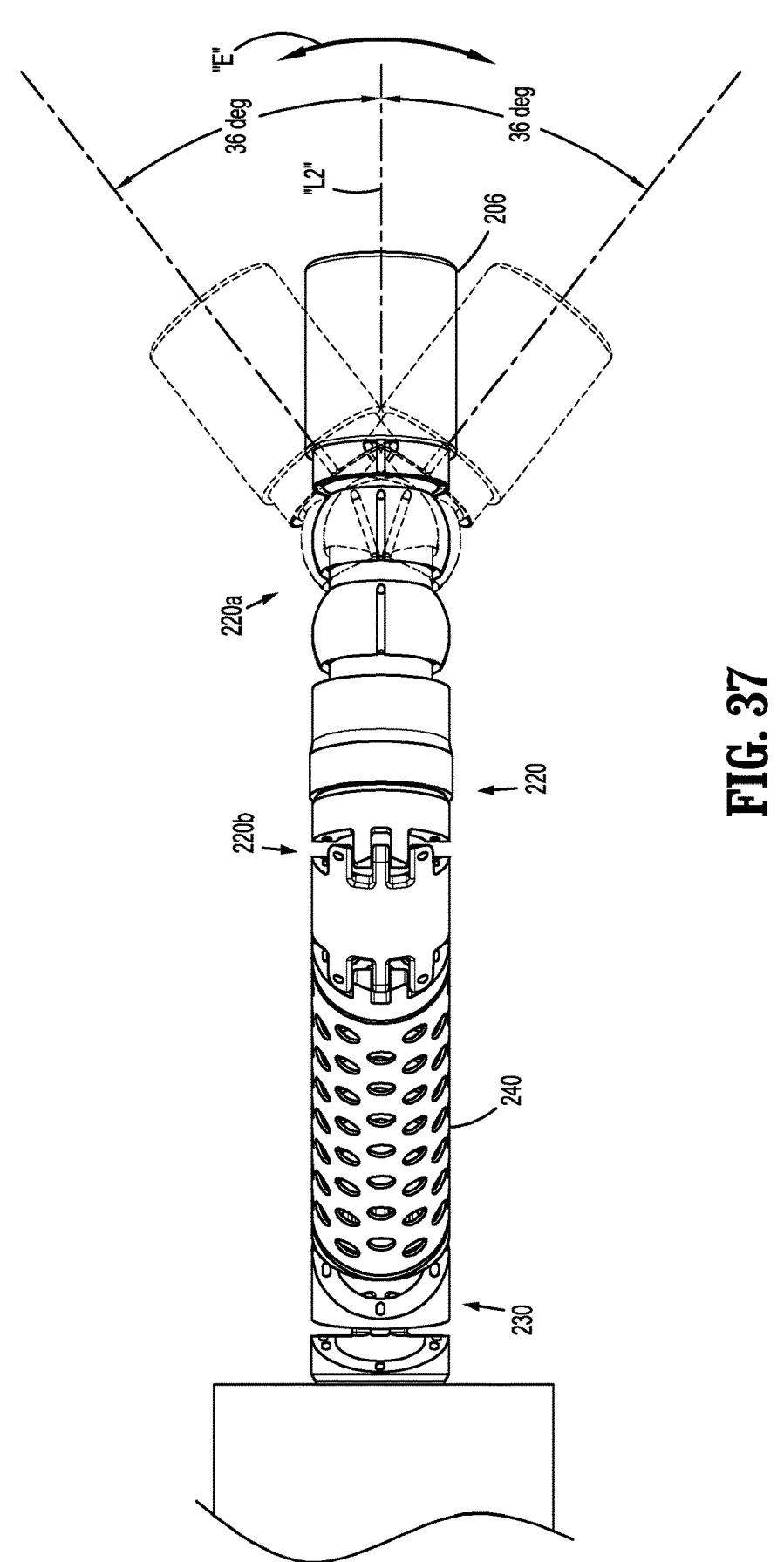
Figure 38:
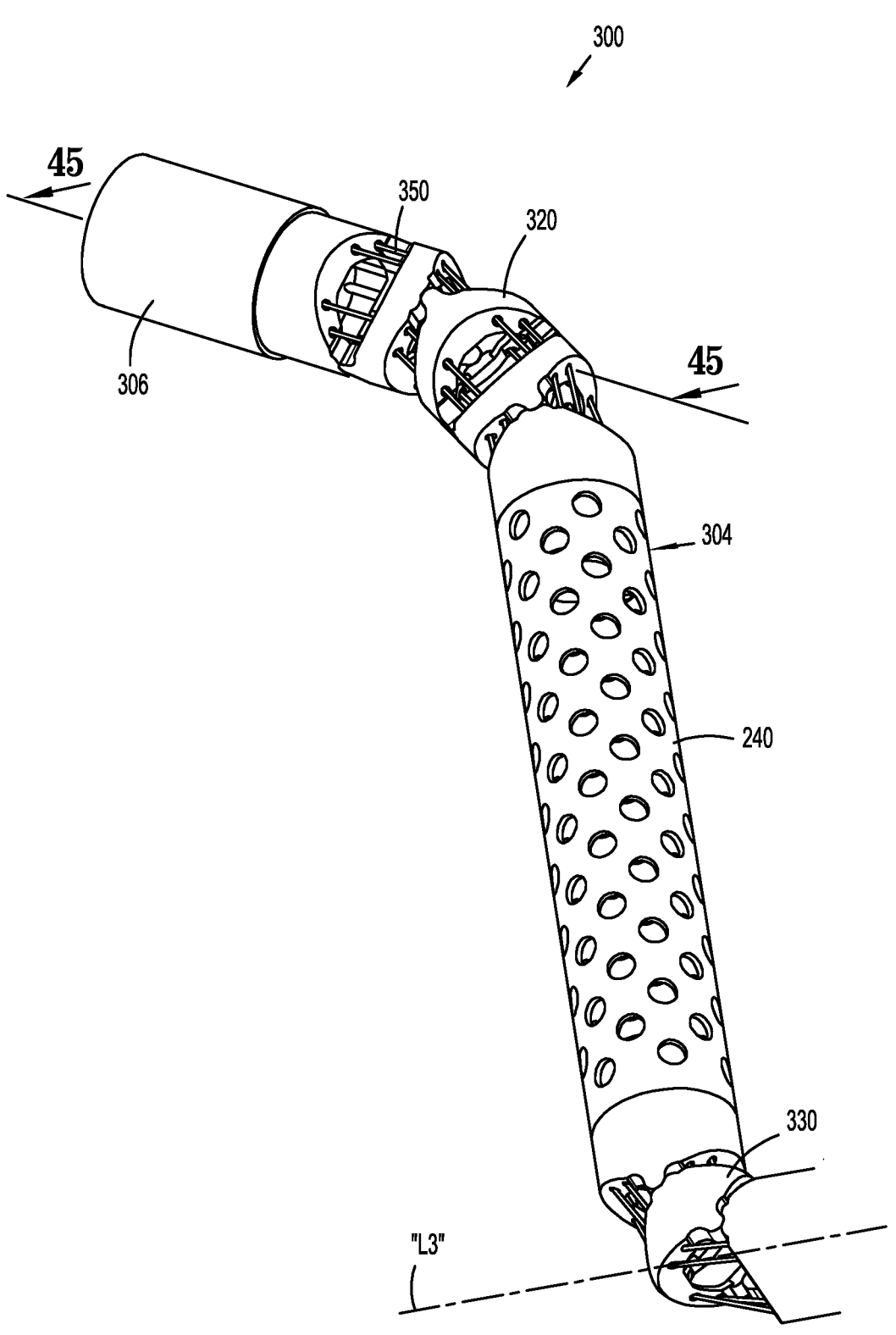
Figure 39:
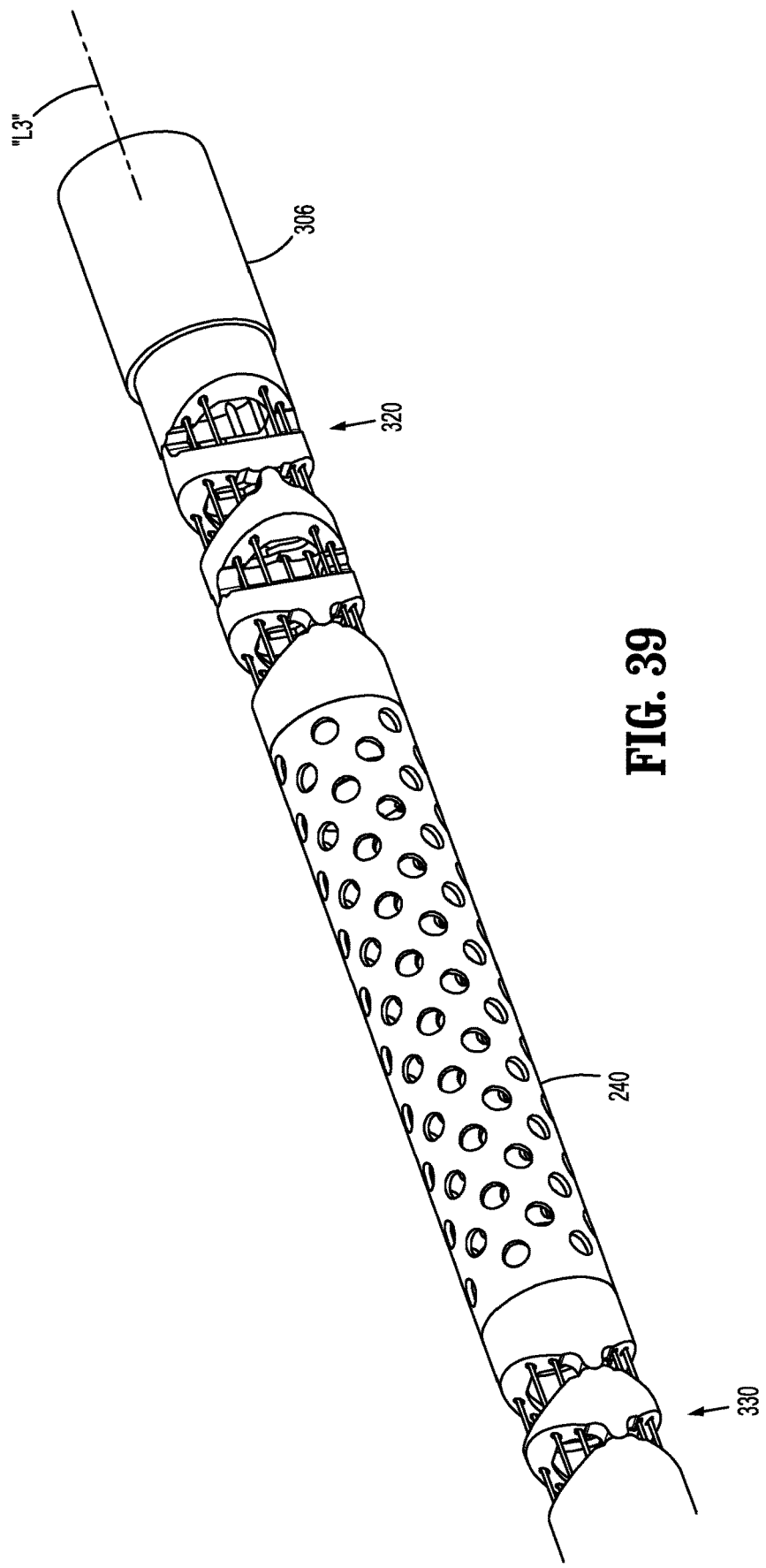
Figure 40:
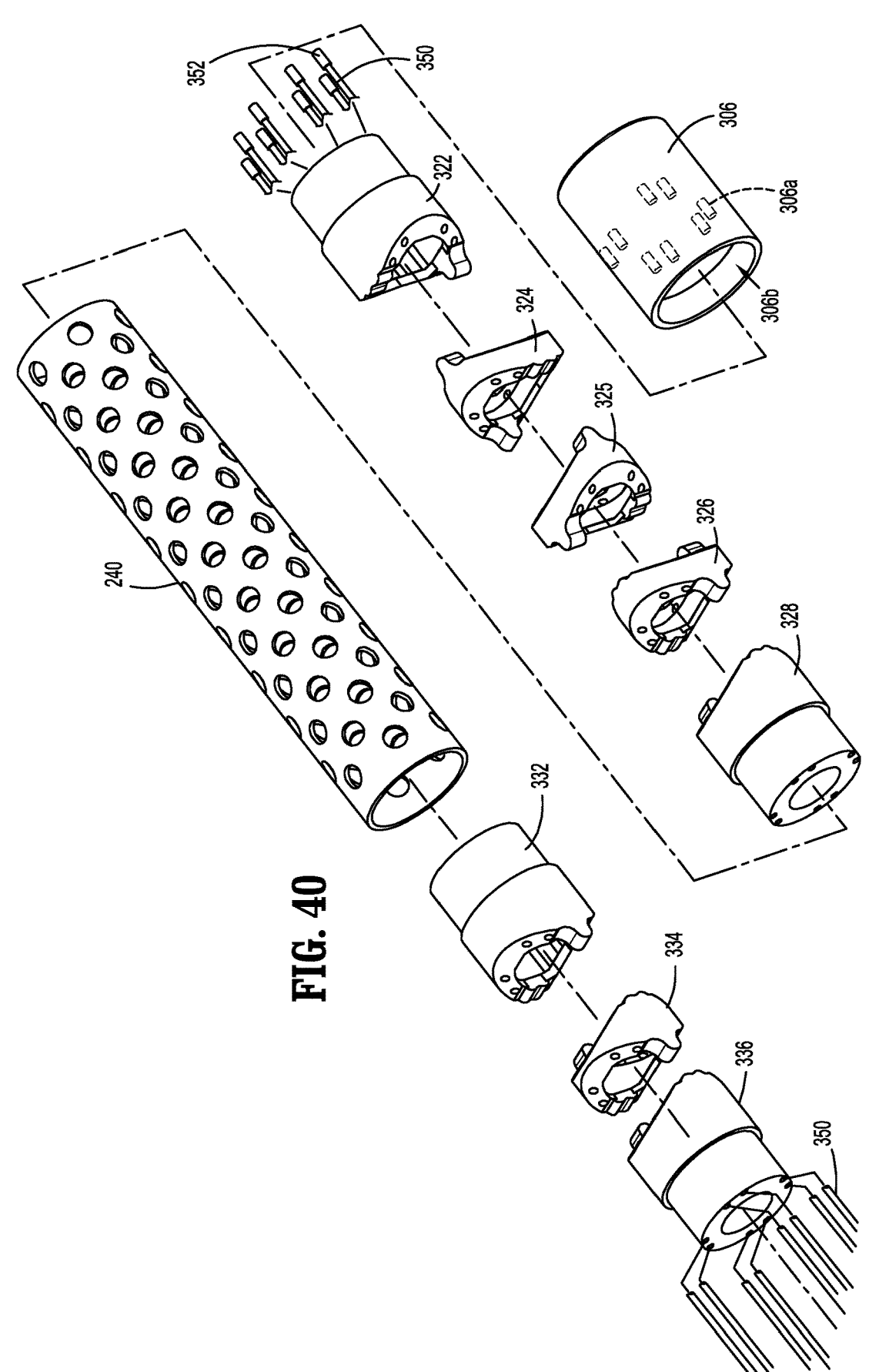
Figure 45:
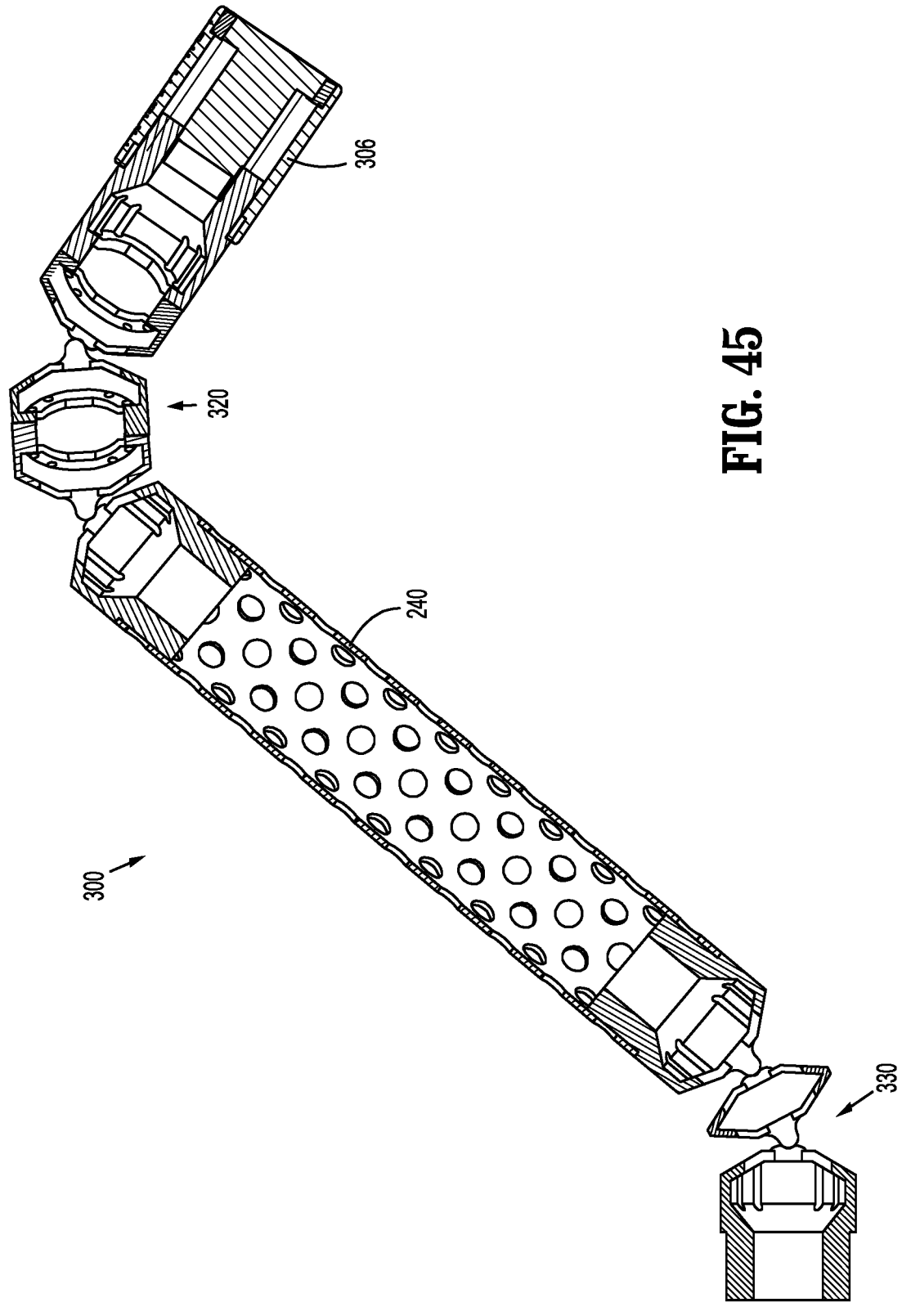
Figure 46:
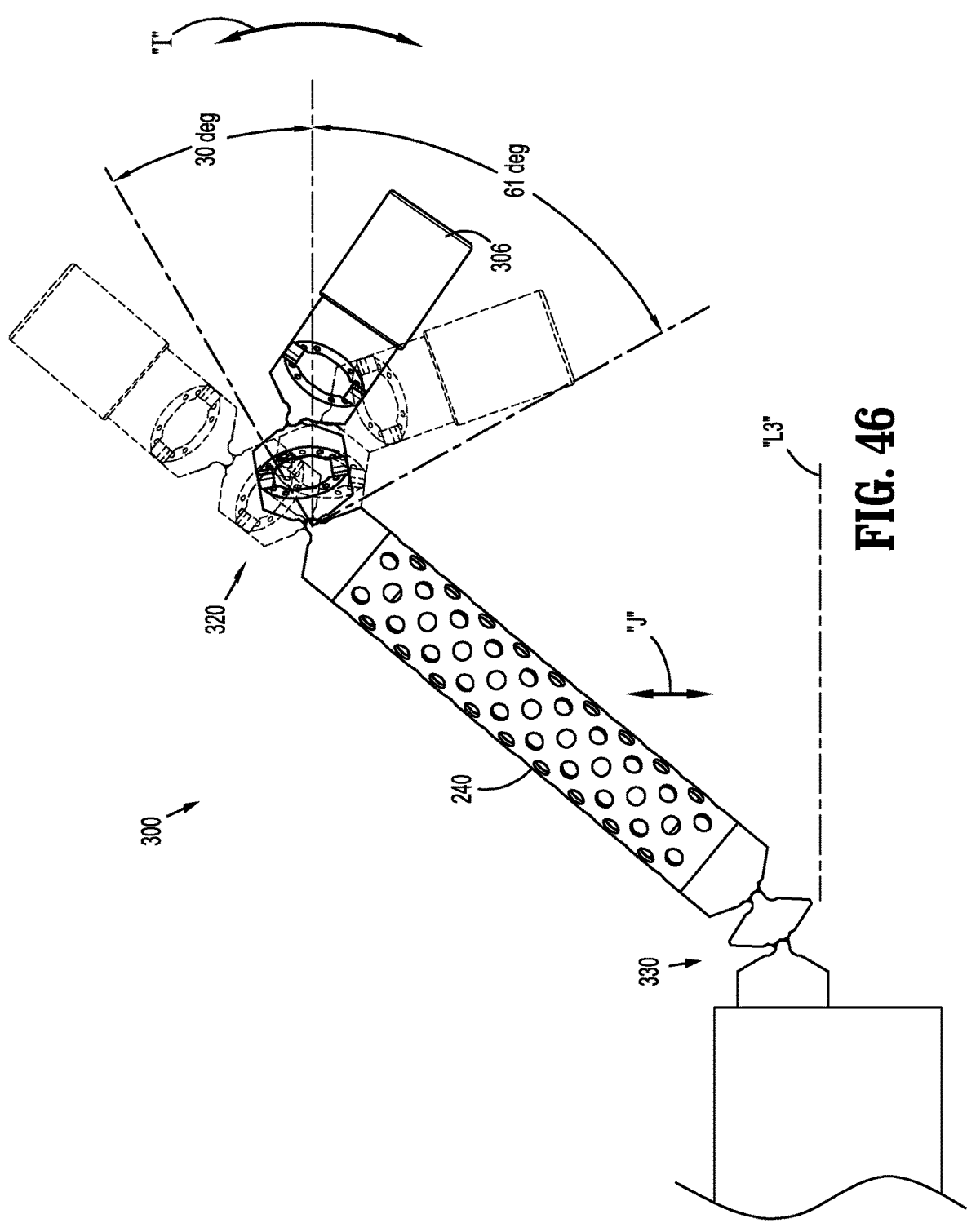
Figure 47:
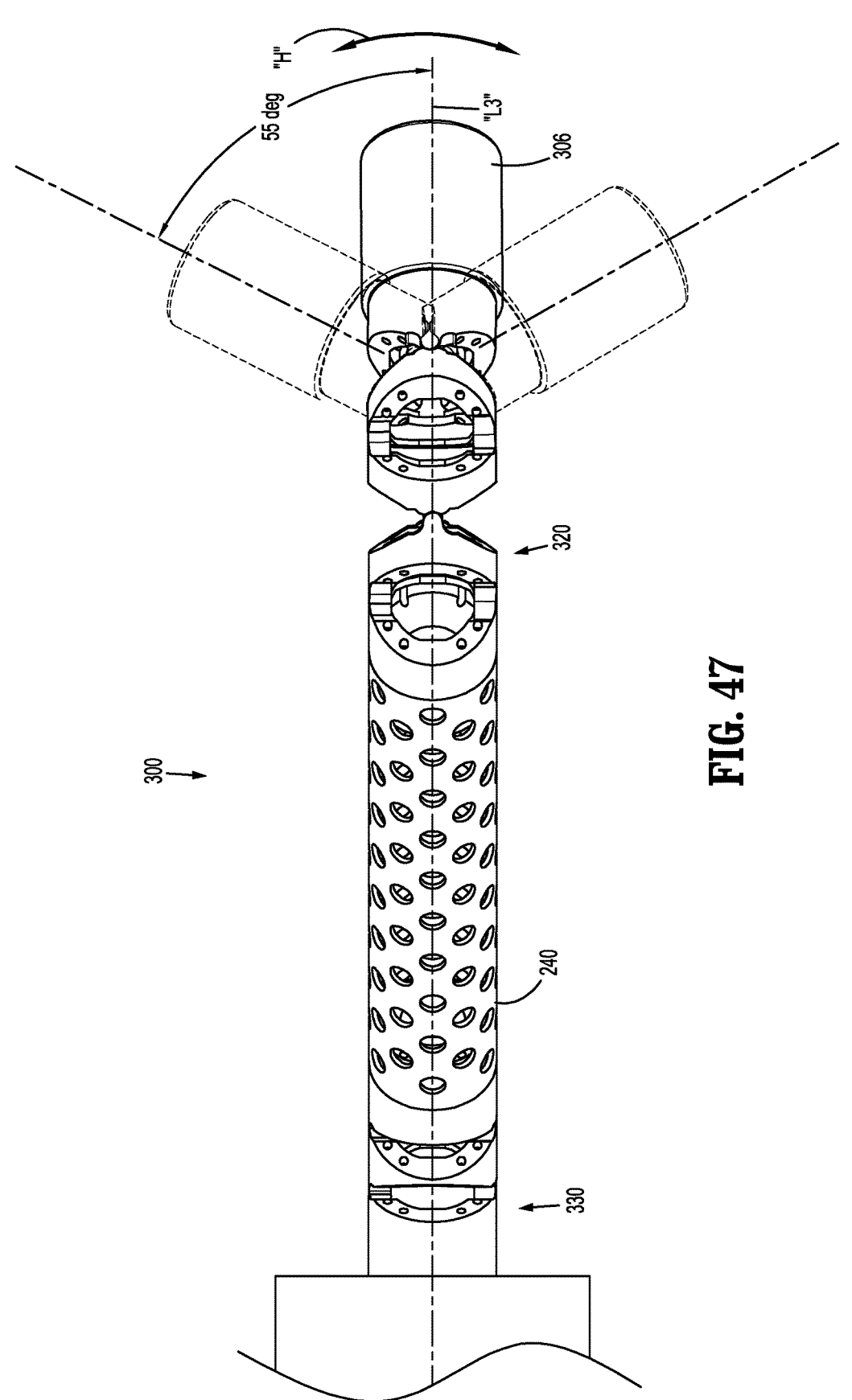
Figure 48:
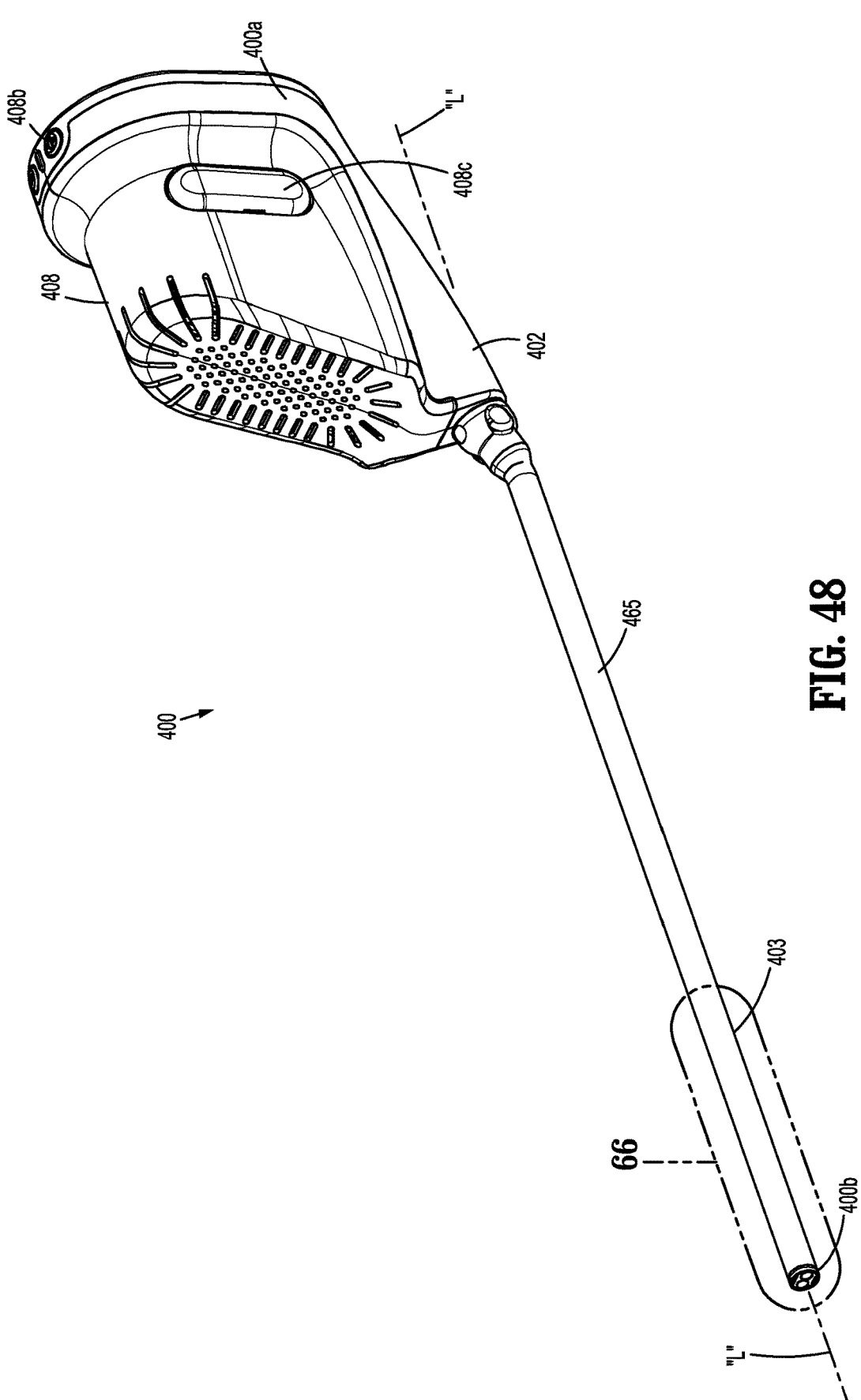
Figures 49, 50:
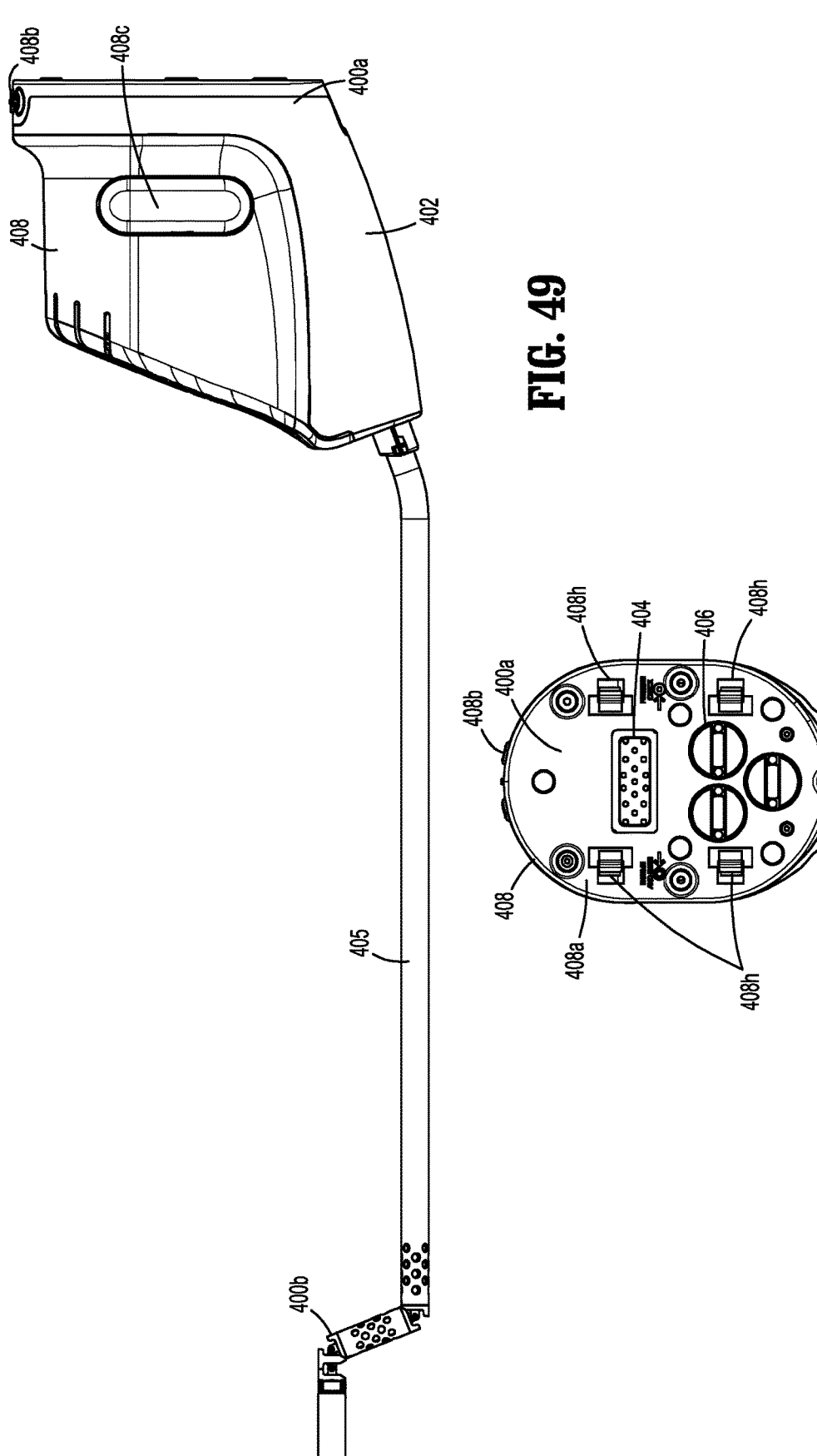
Figure 51A:
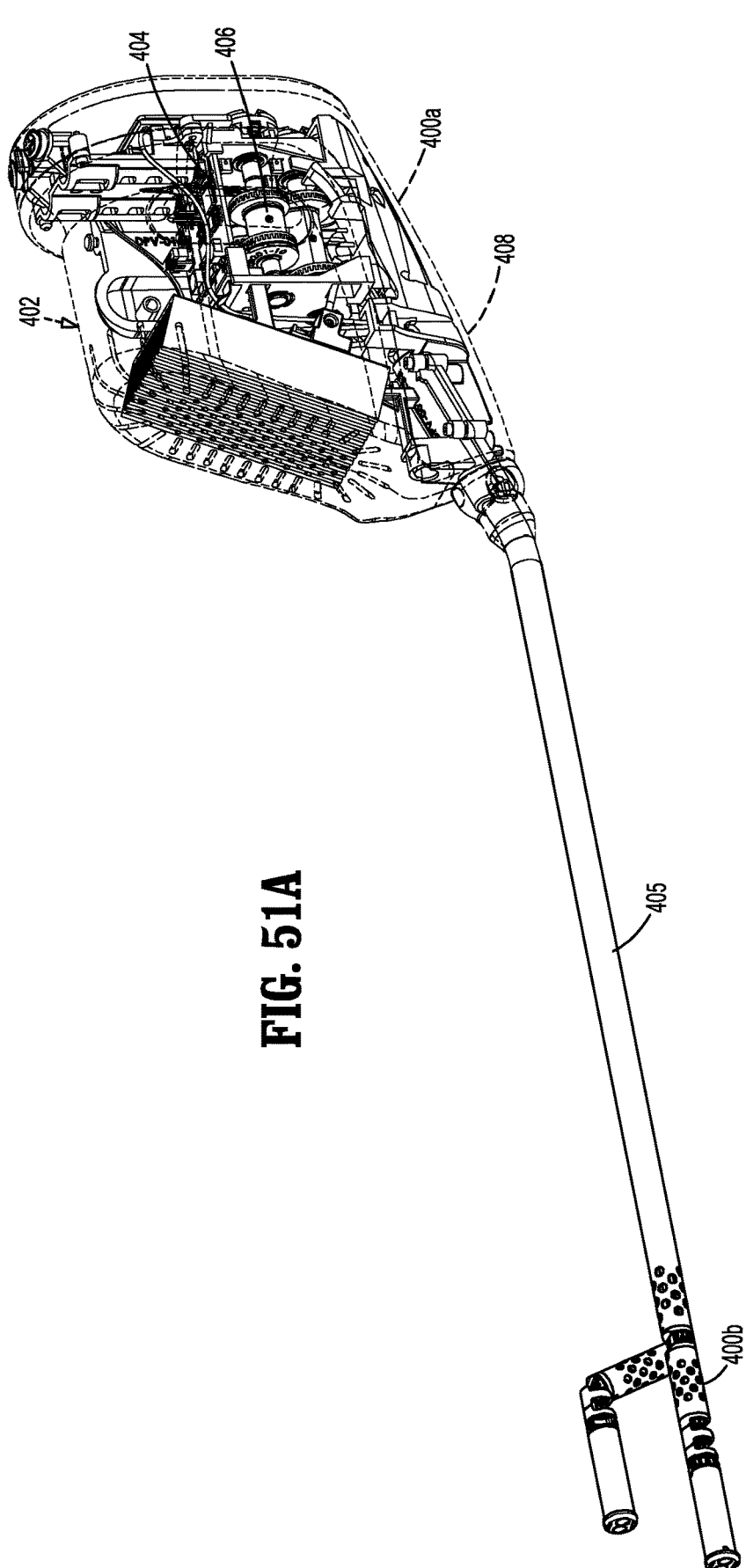
Figure 51B:
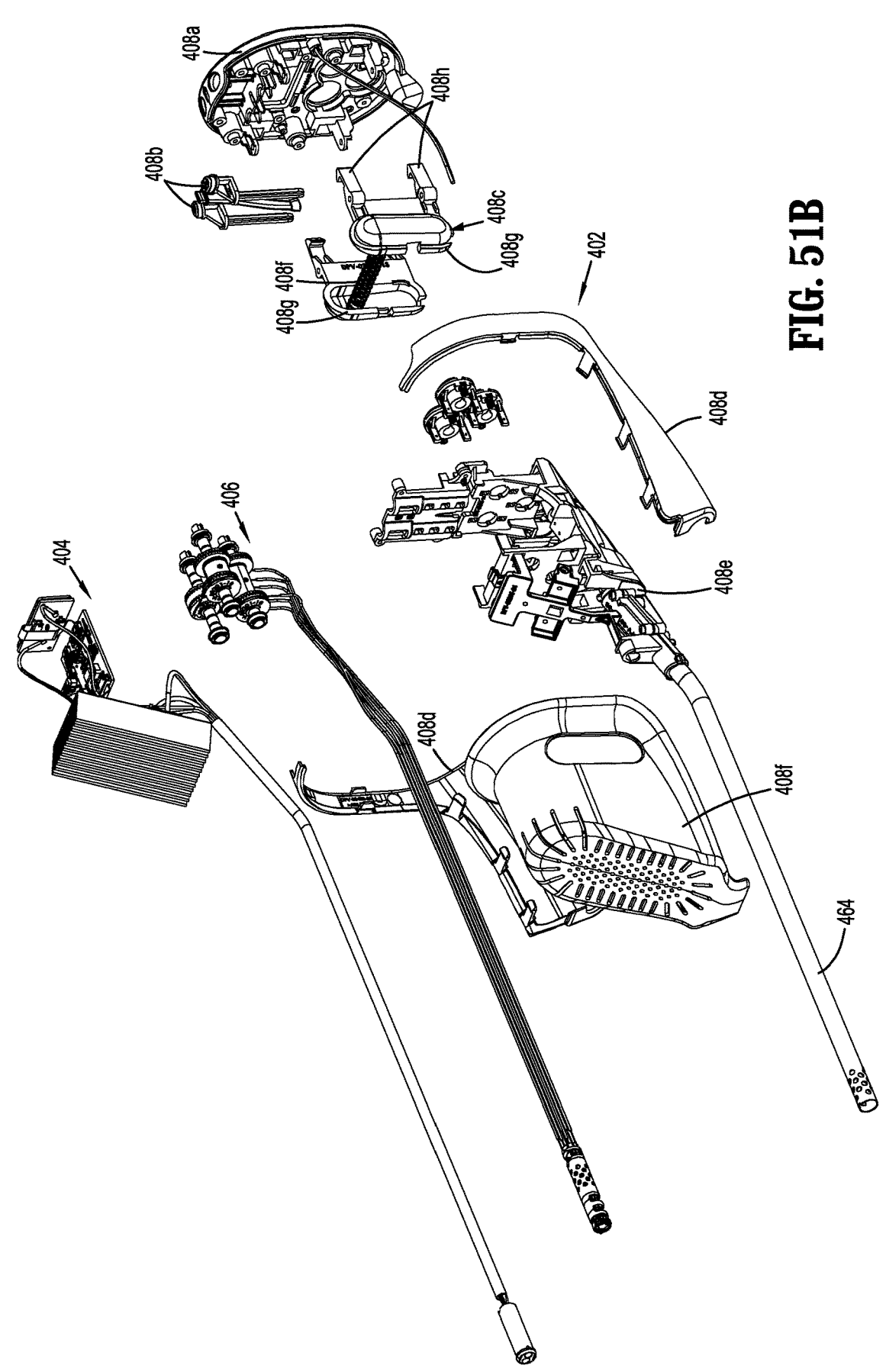
Figure 51C:
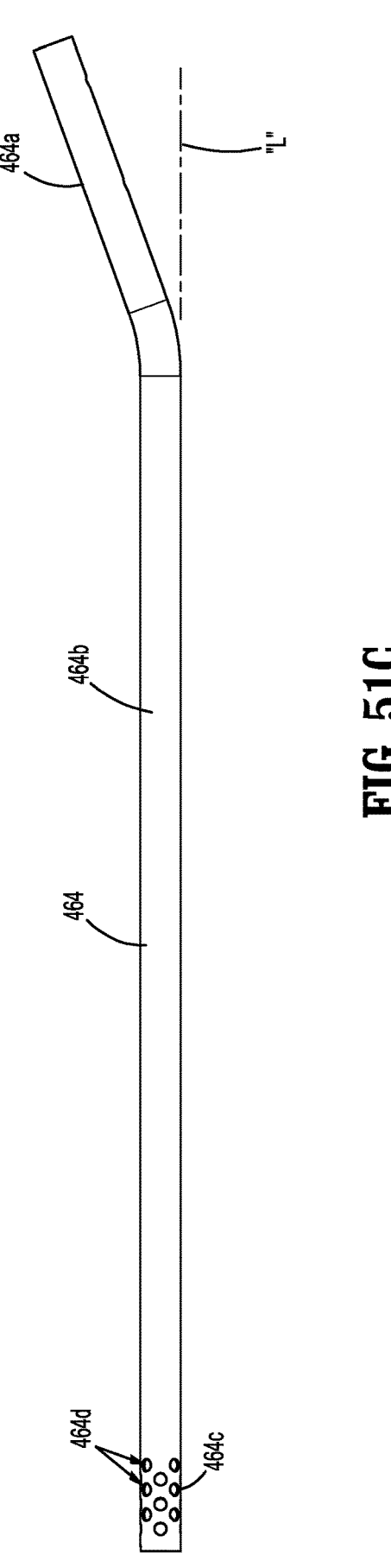
Figure 52A:
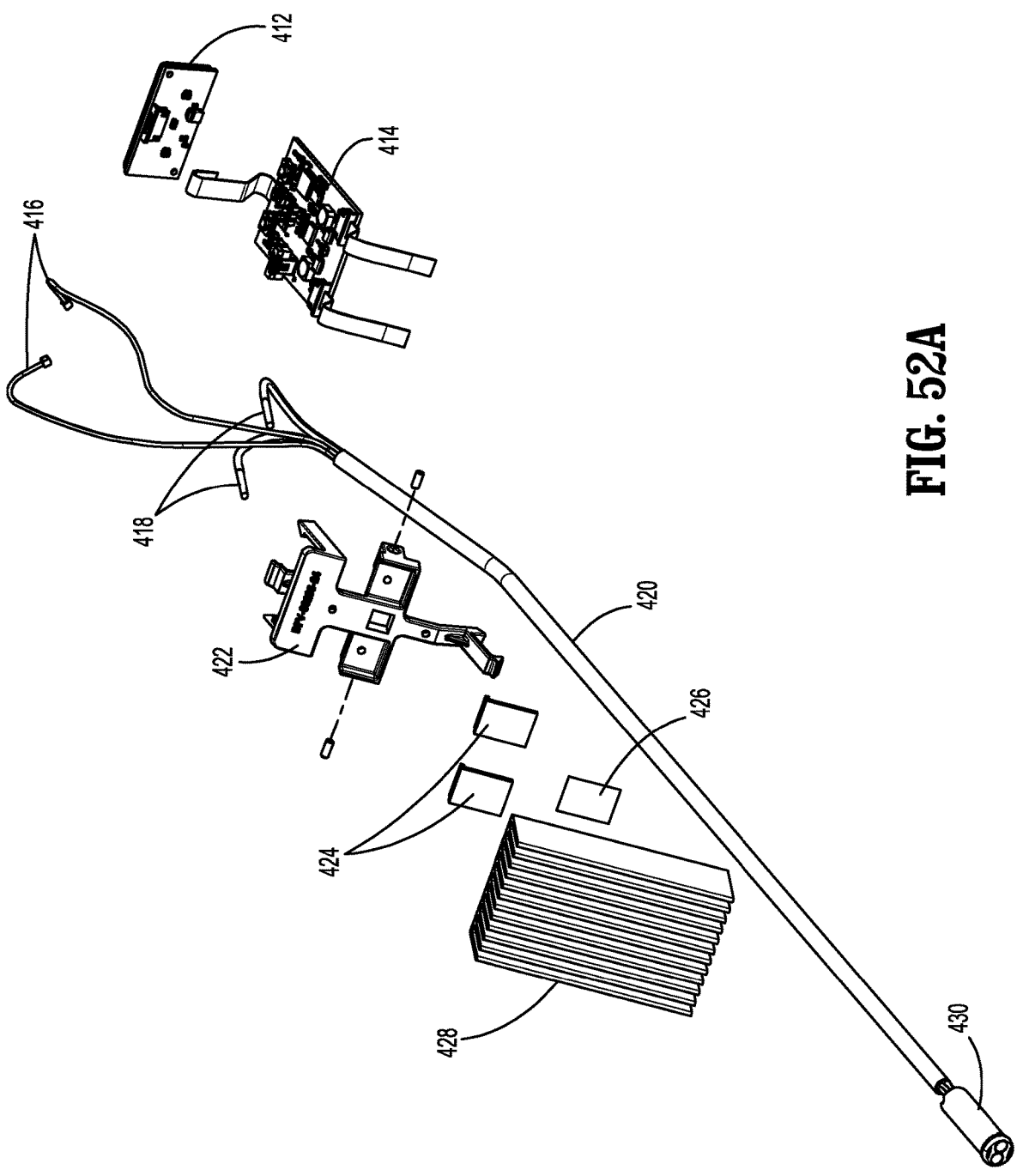
Figure 52B:
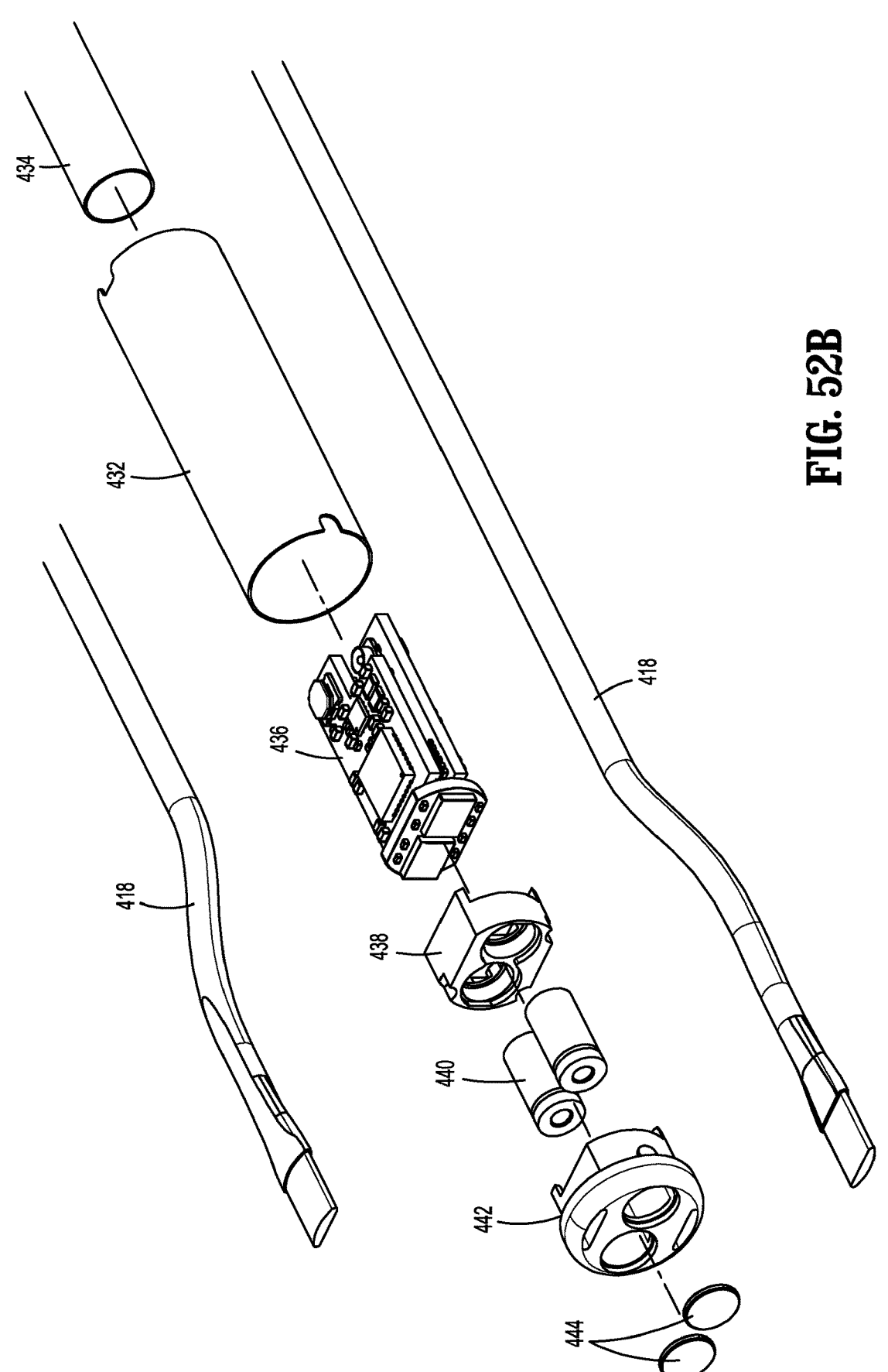
Figures 52C, 52D:
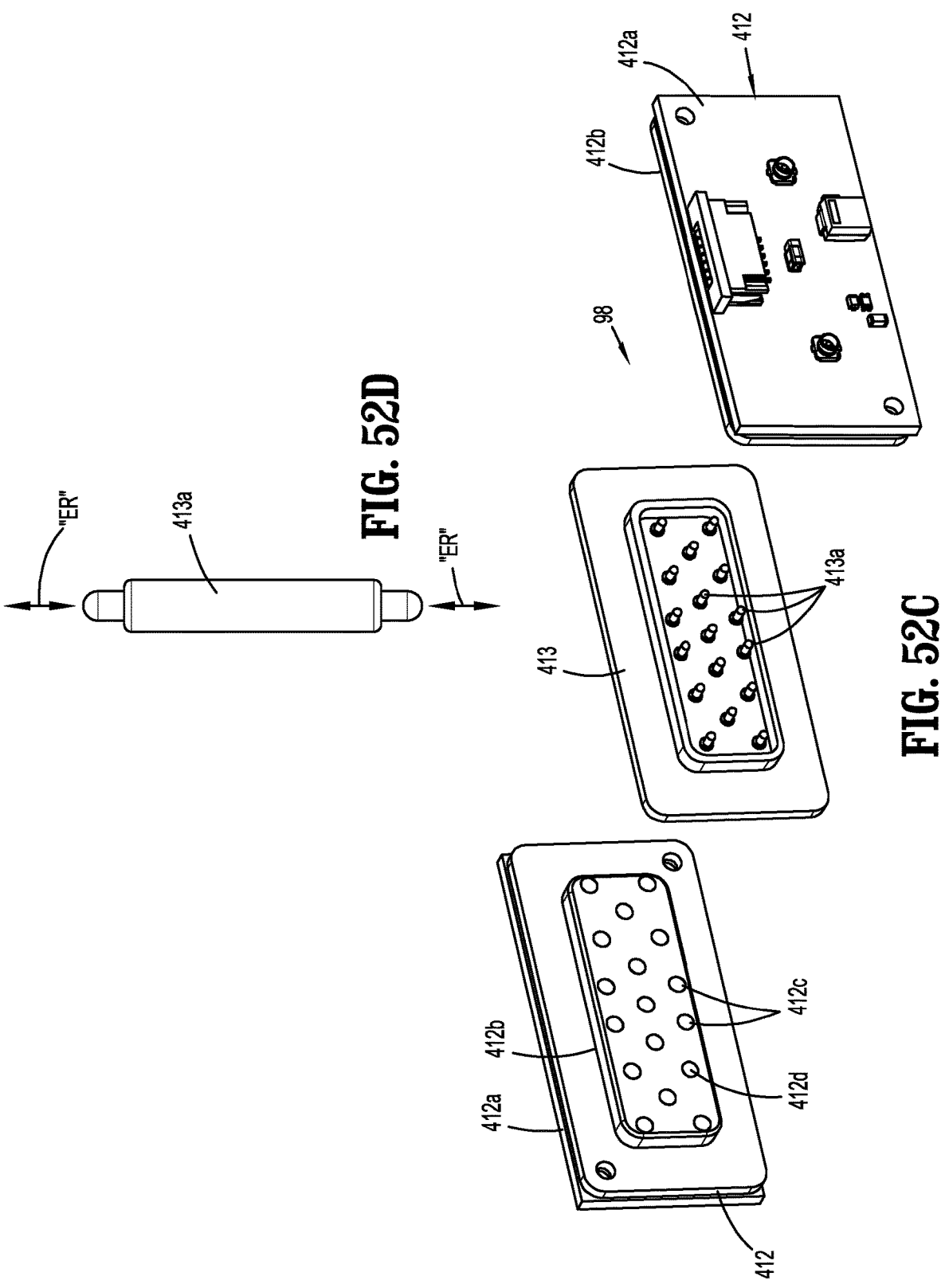
Figure 53:
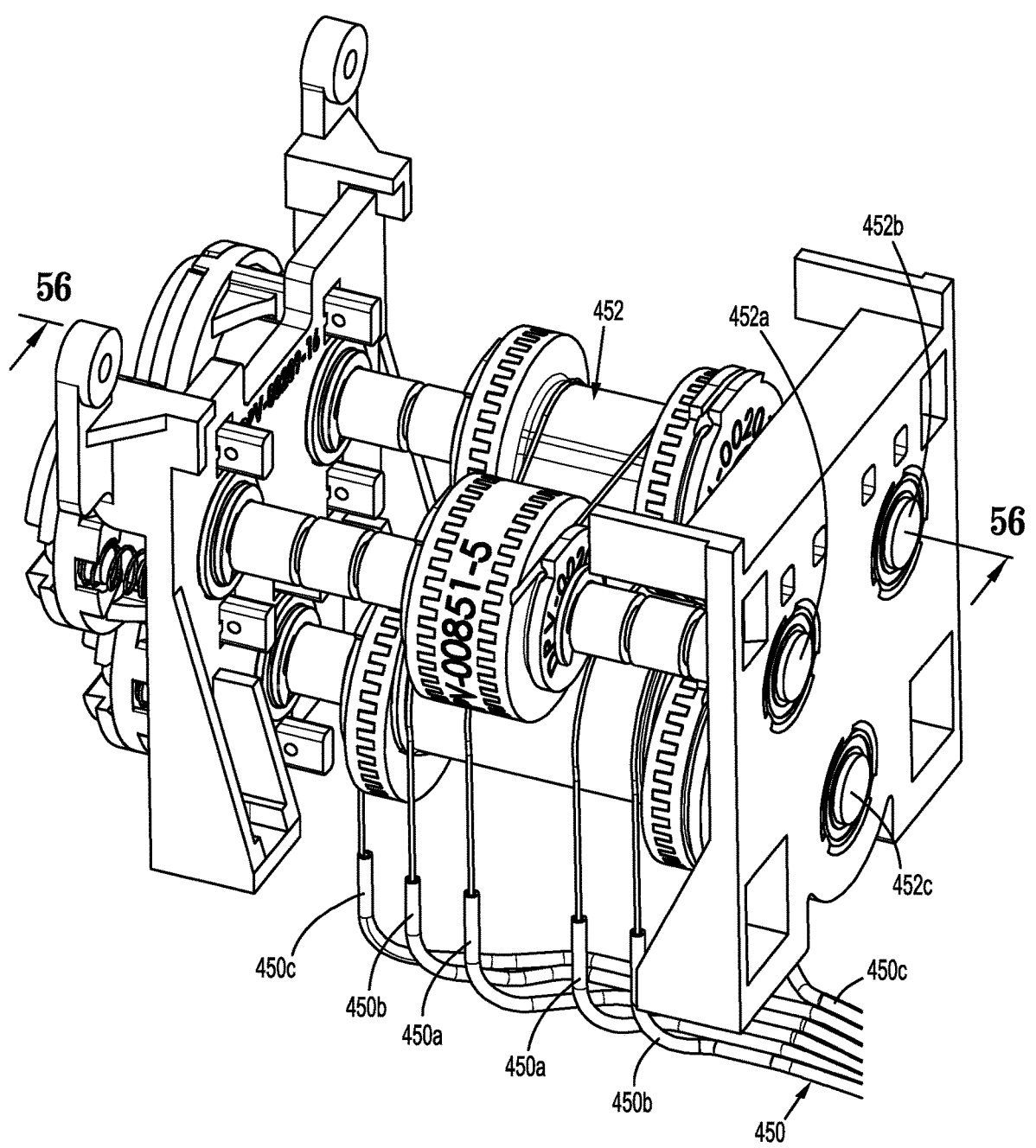
Figure 54:
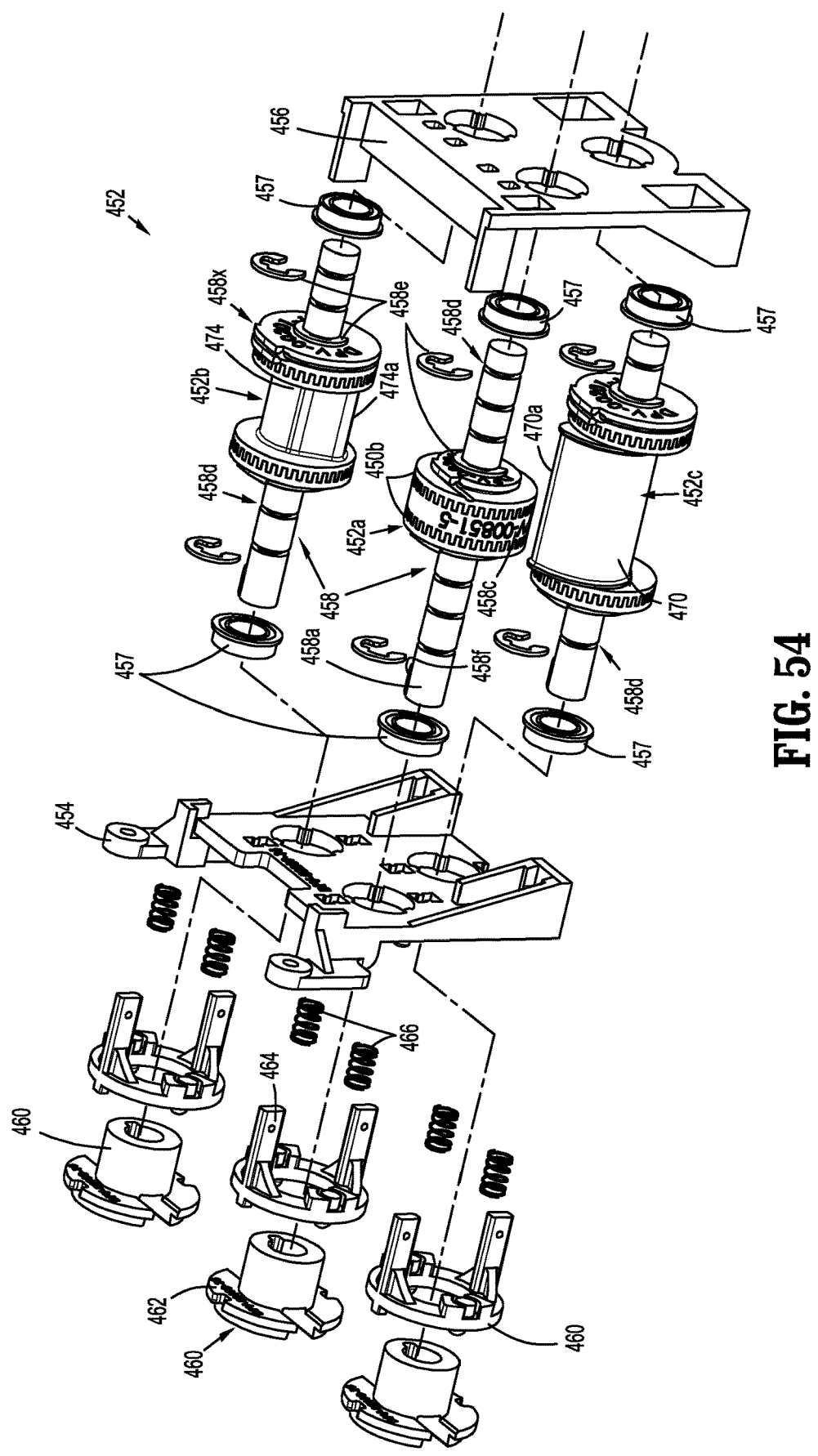
Figure 55:
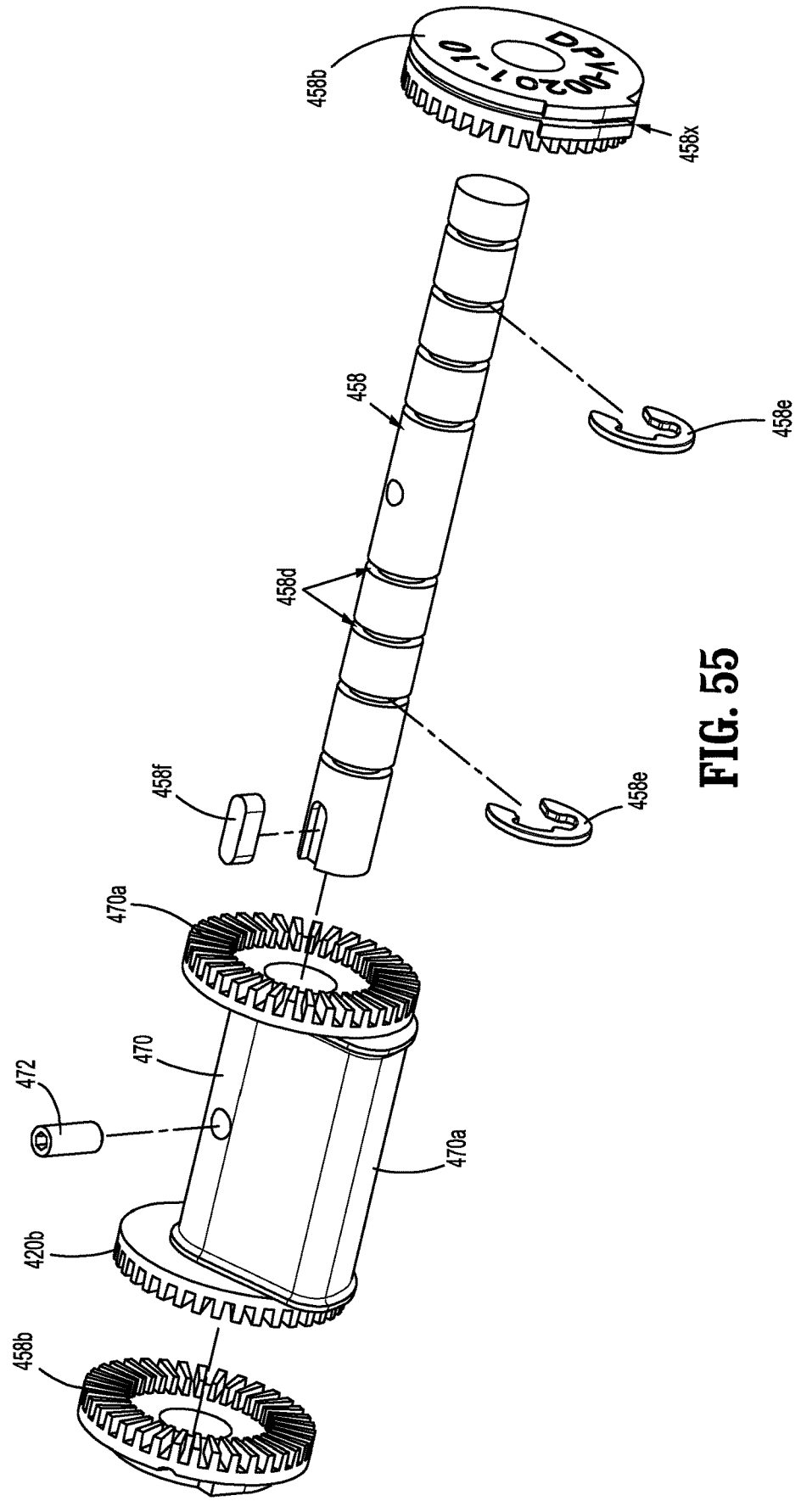
Figures 56, 57:
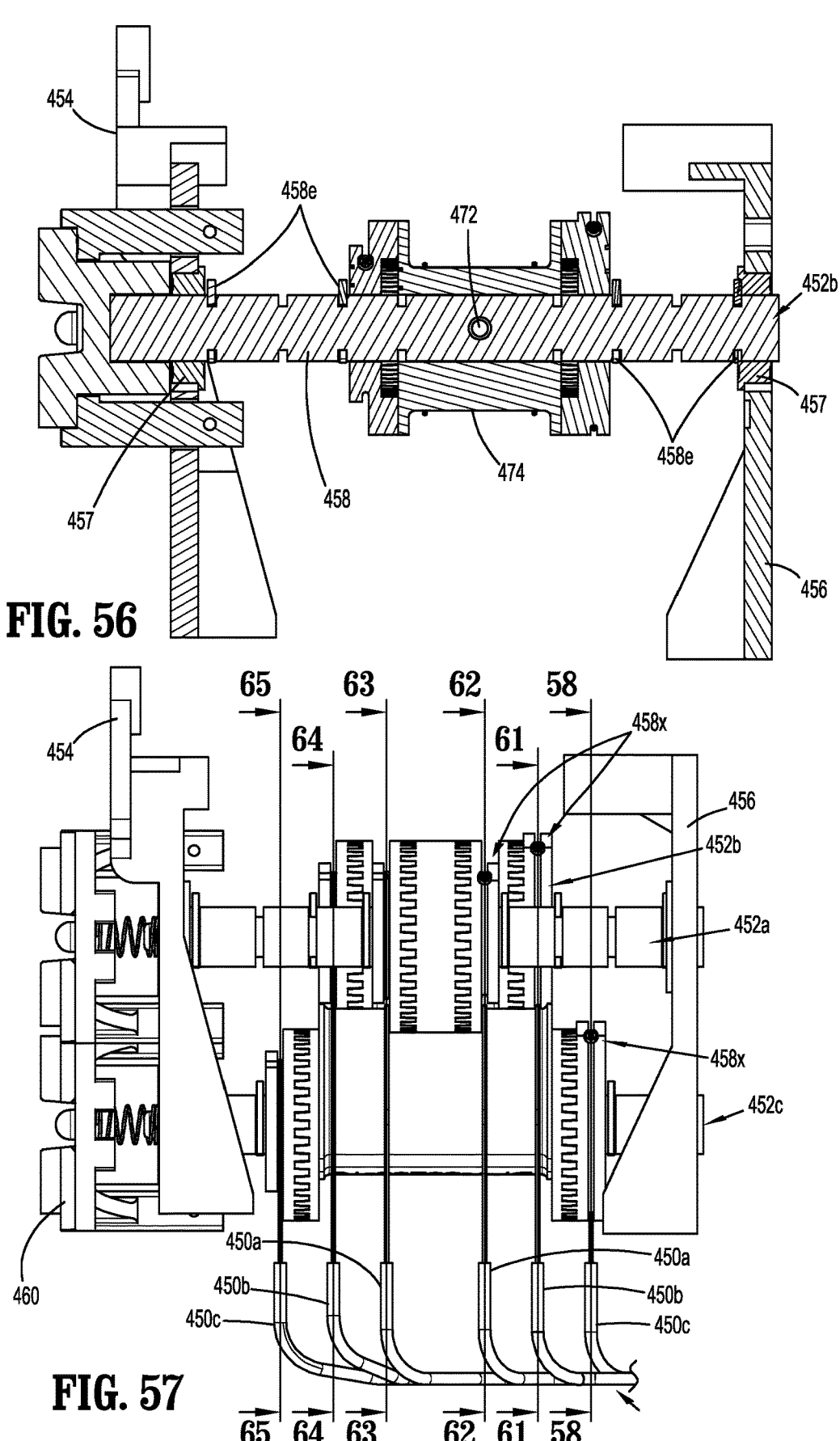
Figure 62:
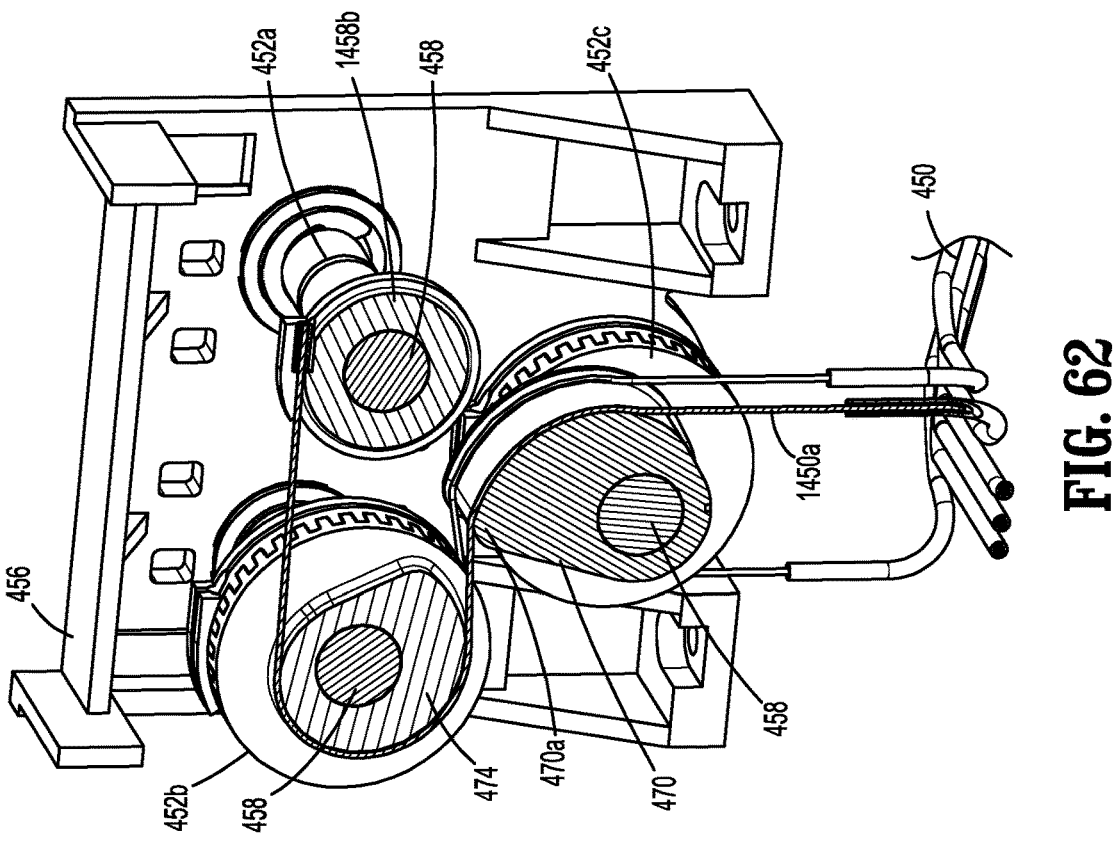
Figure 61:
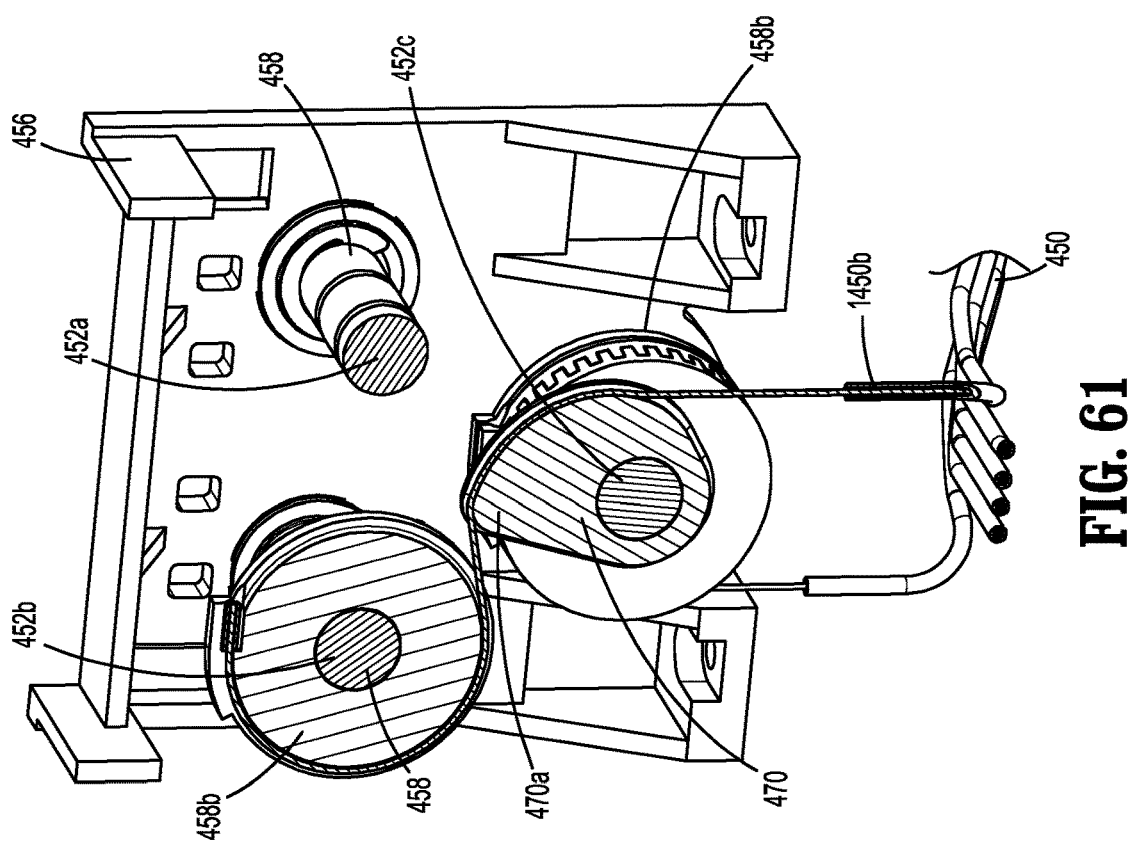
Figures 63, 64:
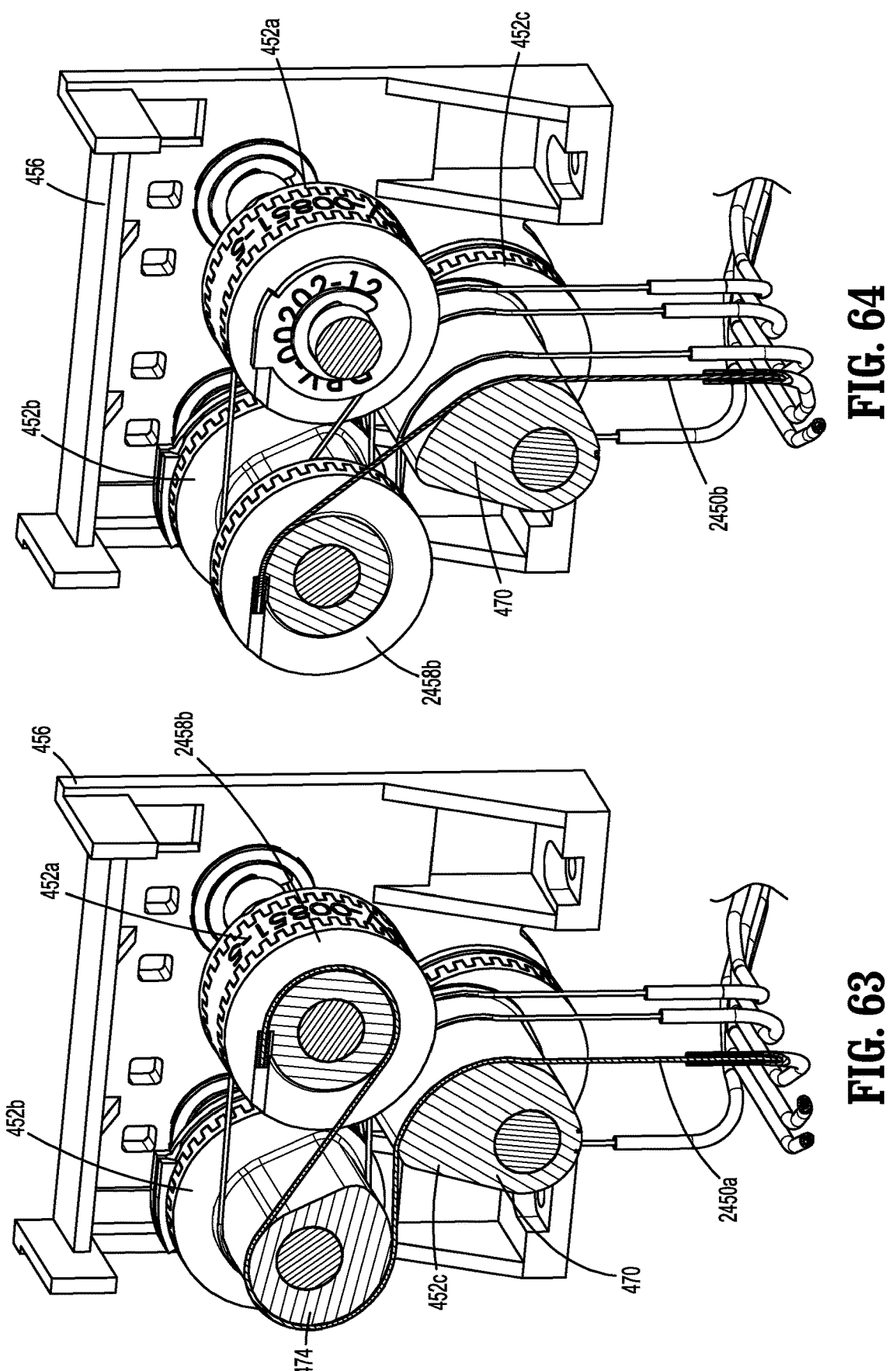
Figure 65:
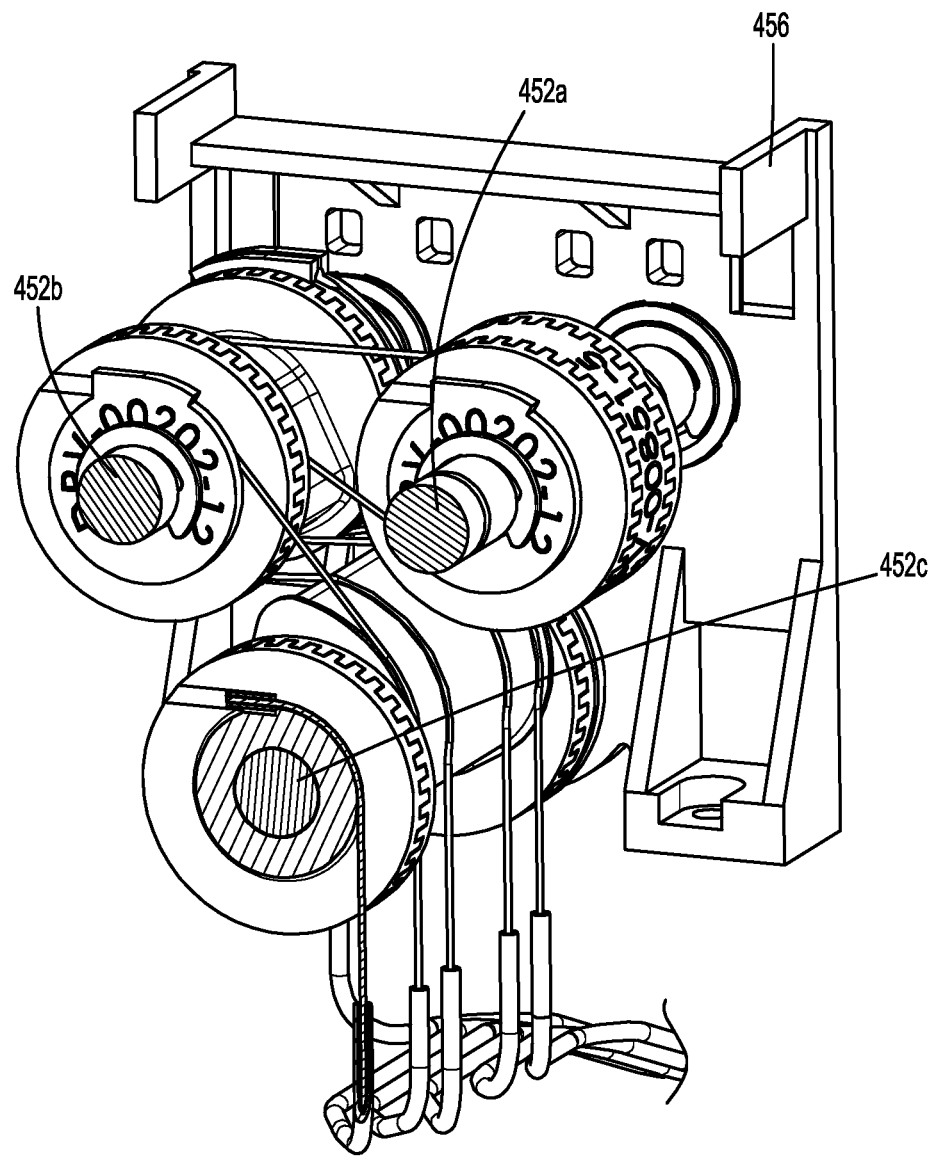
Figures 66, 67:
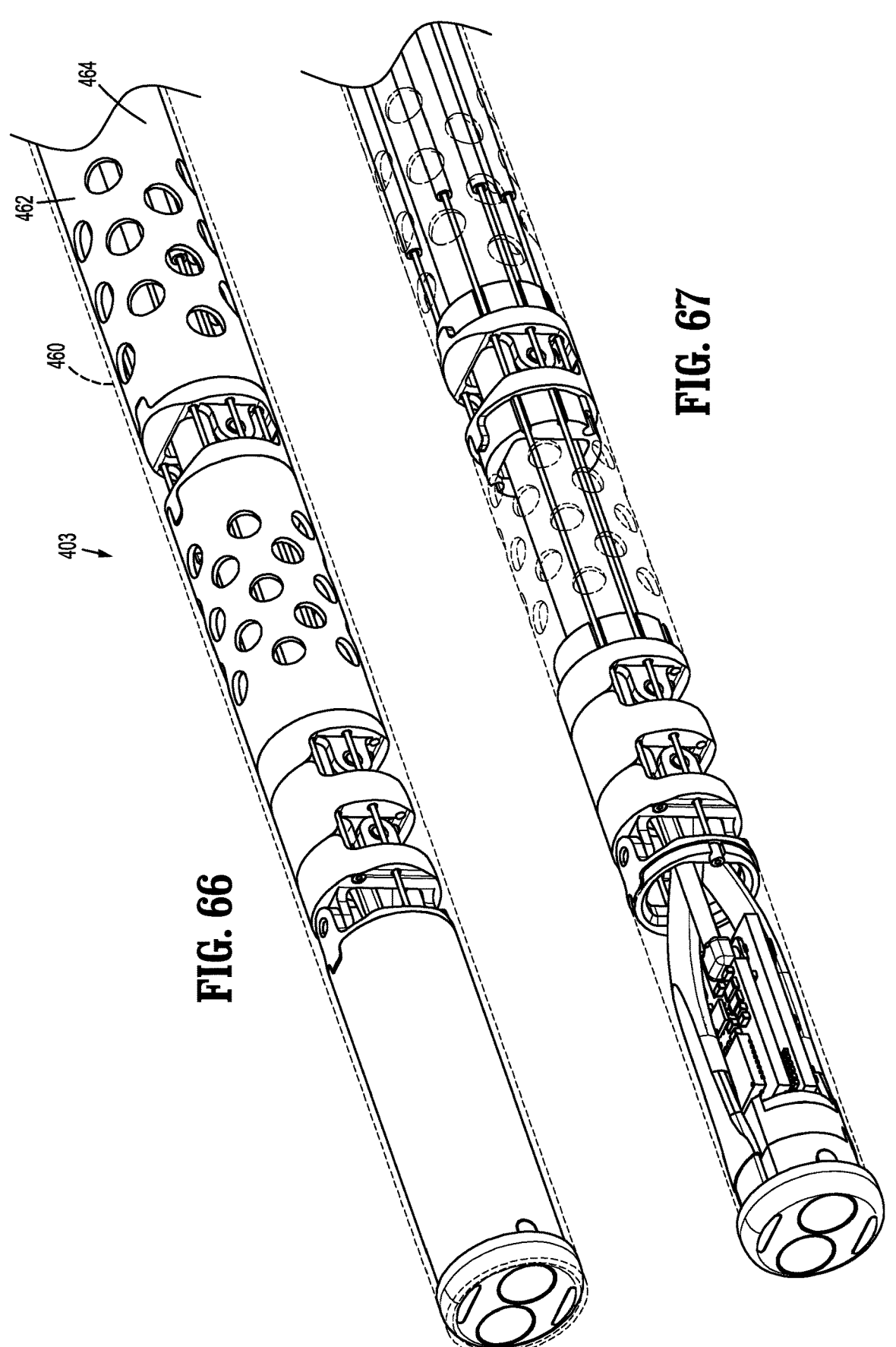
Figure 68:
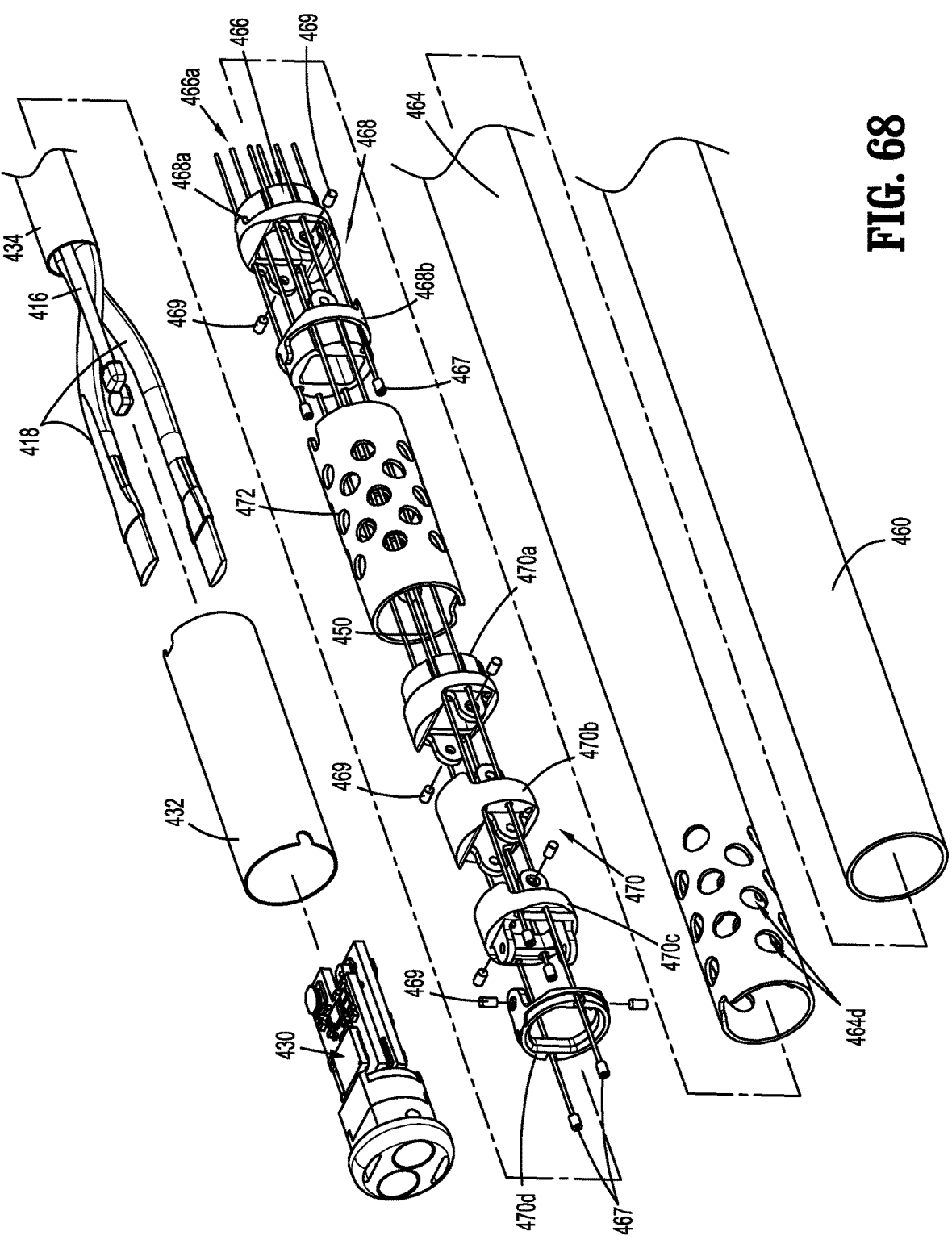
Figures 69, 70:
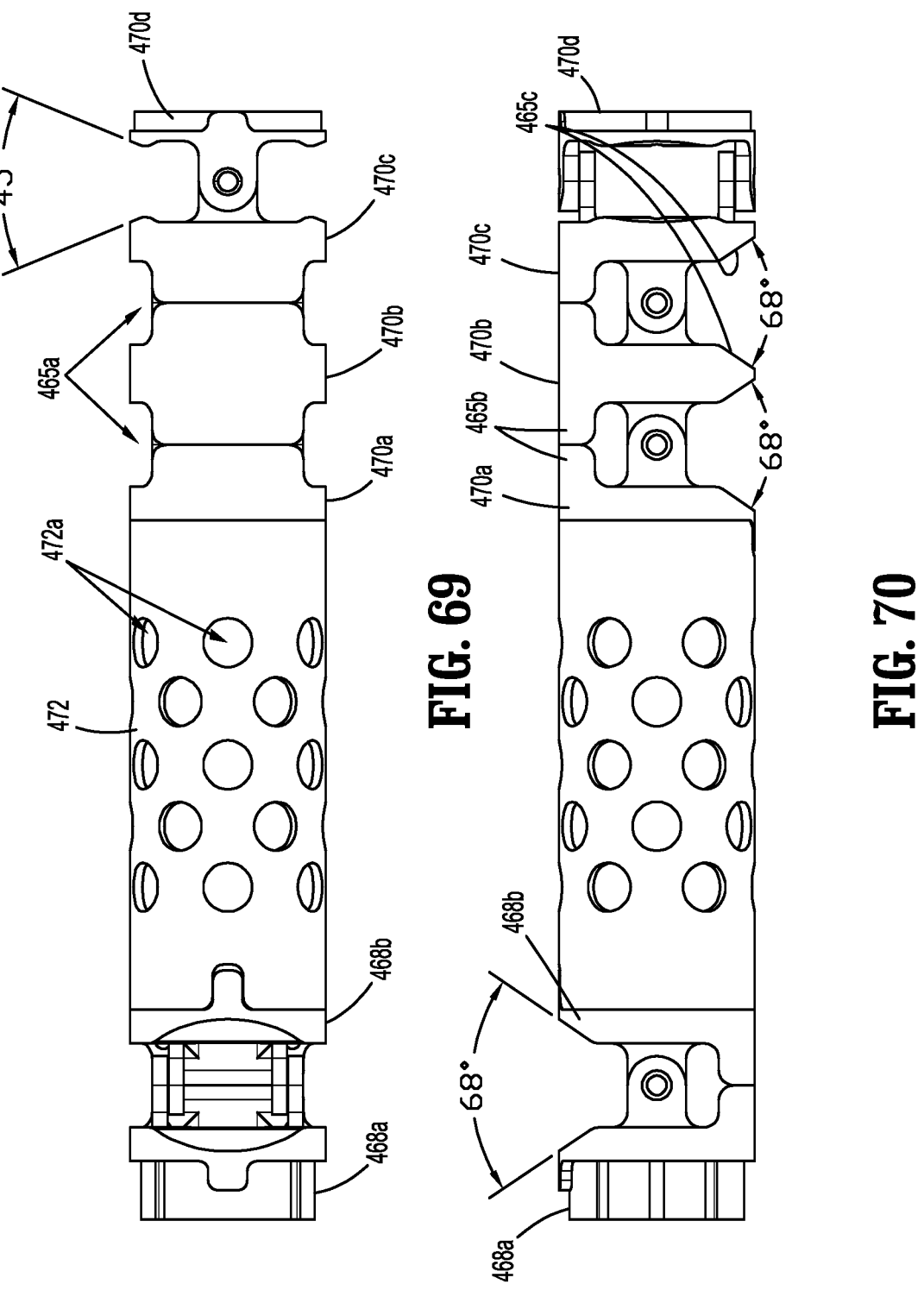
Figure 71:
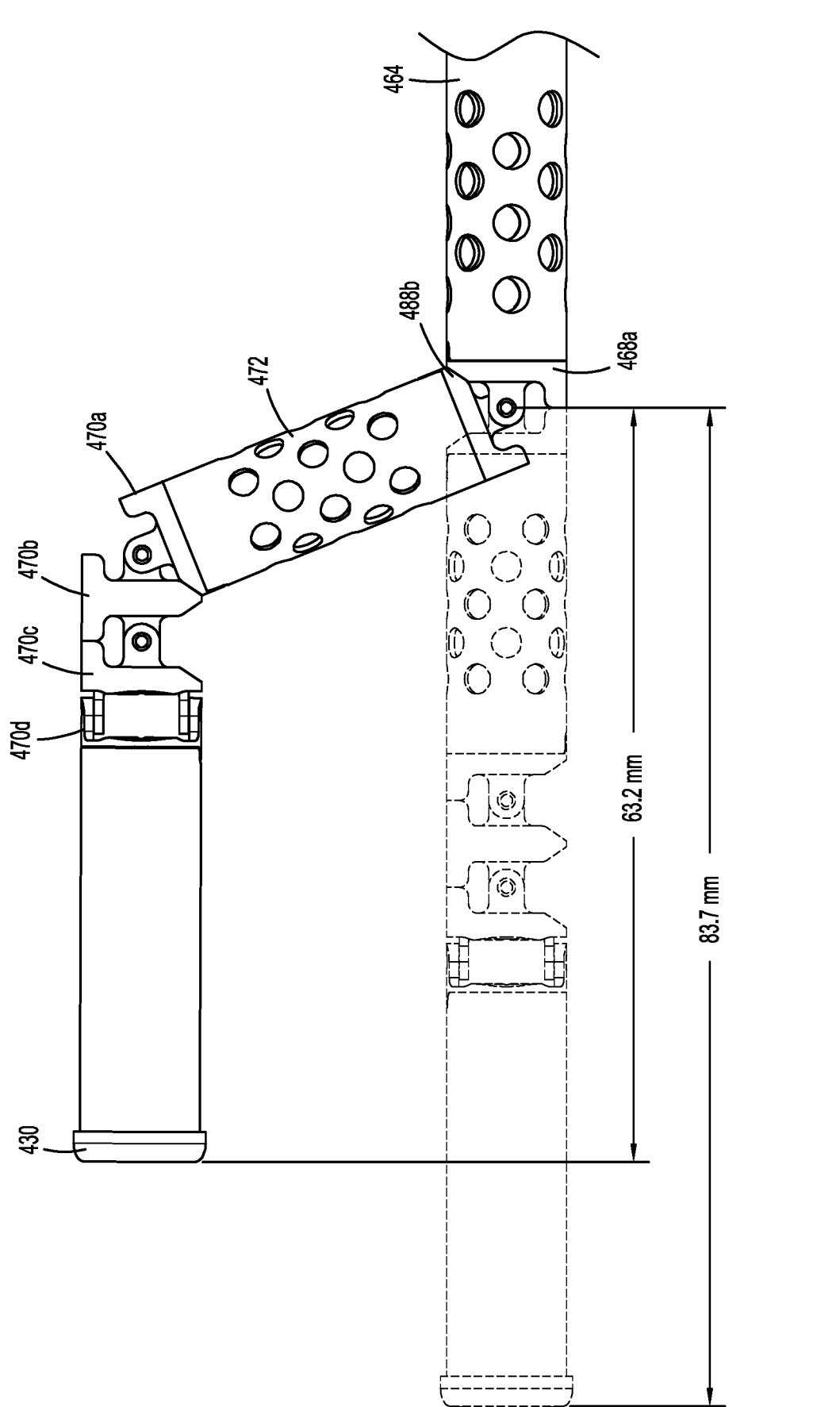
Figure 72:
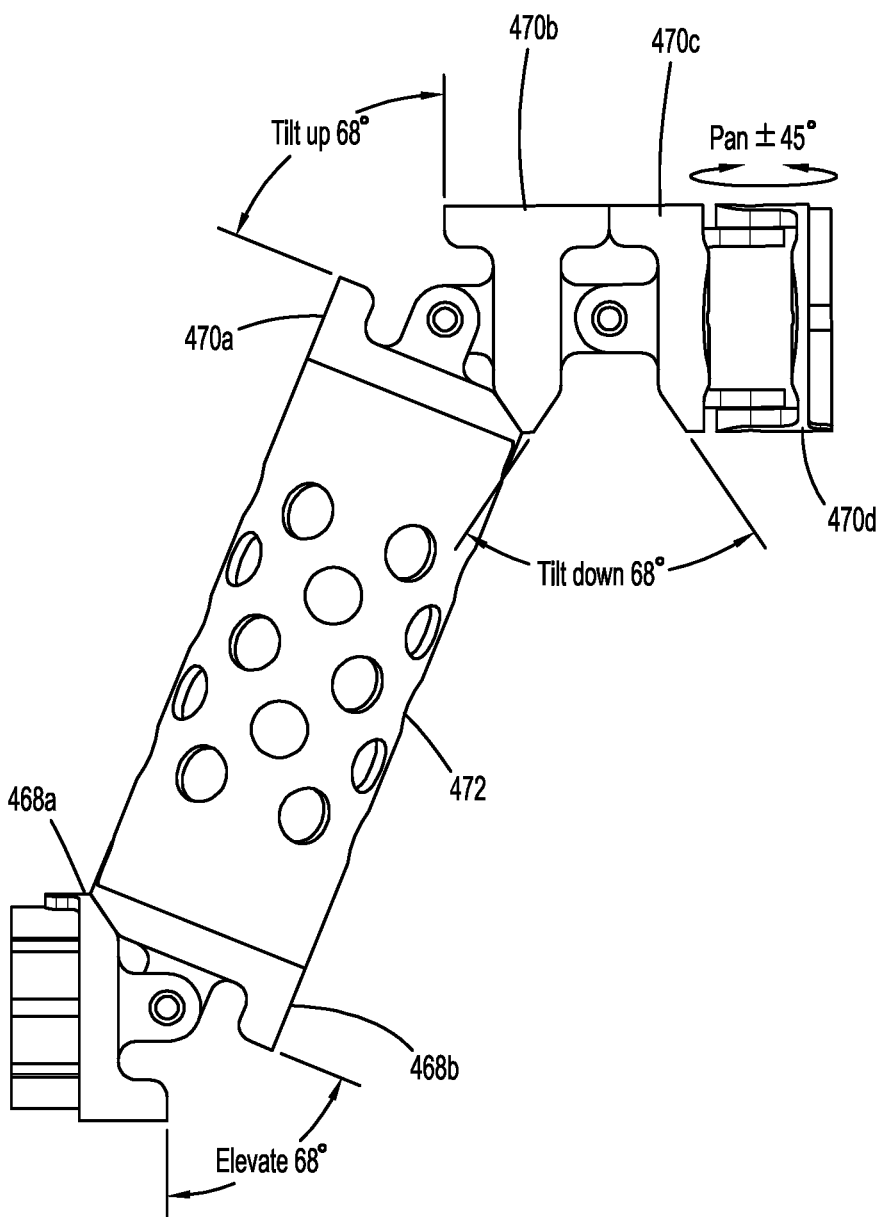
Figure 73:
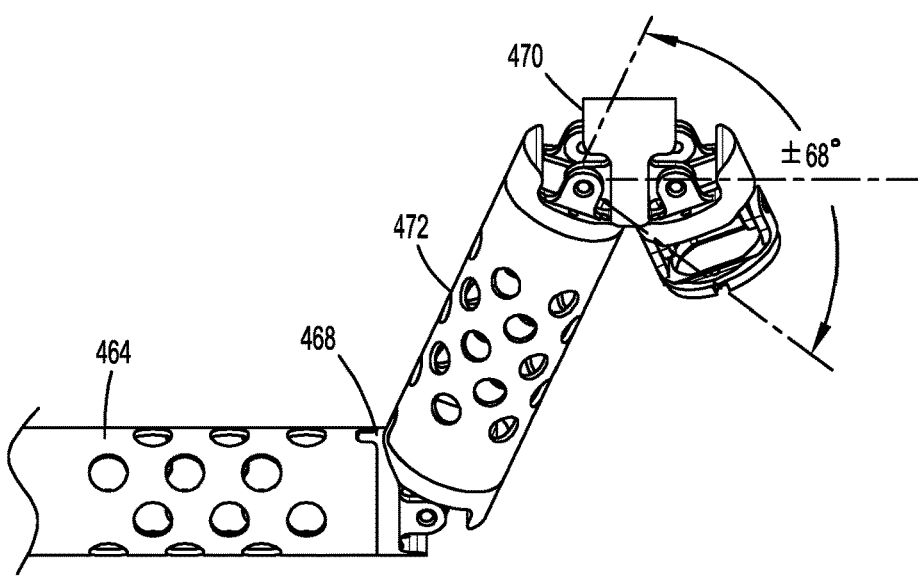
Figure 74:
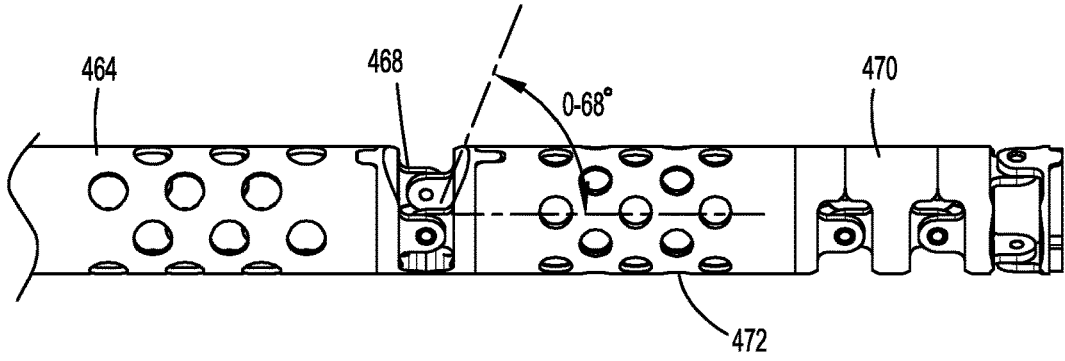
Figure 75:
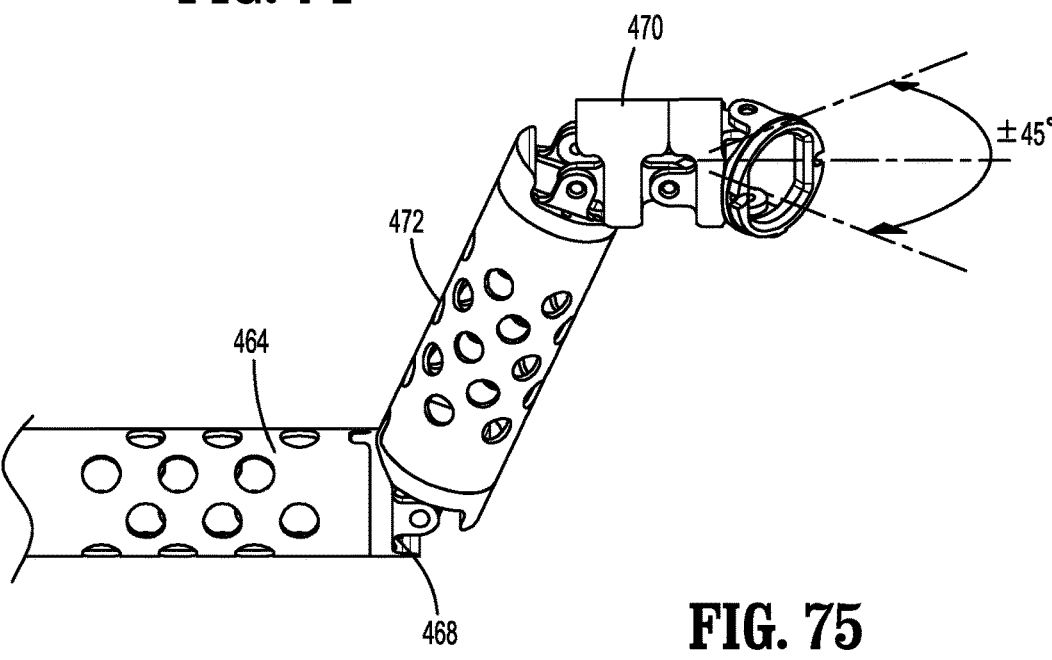
Figures 76, 77, 78:
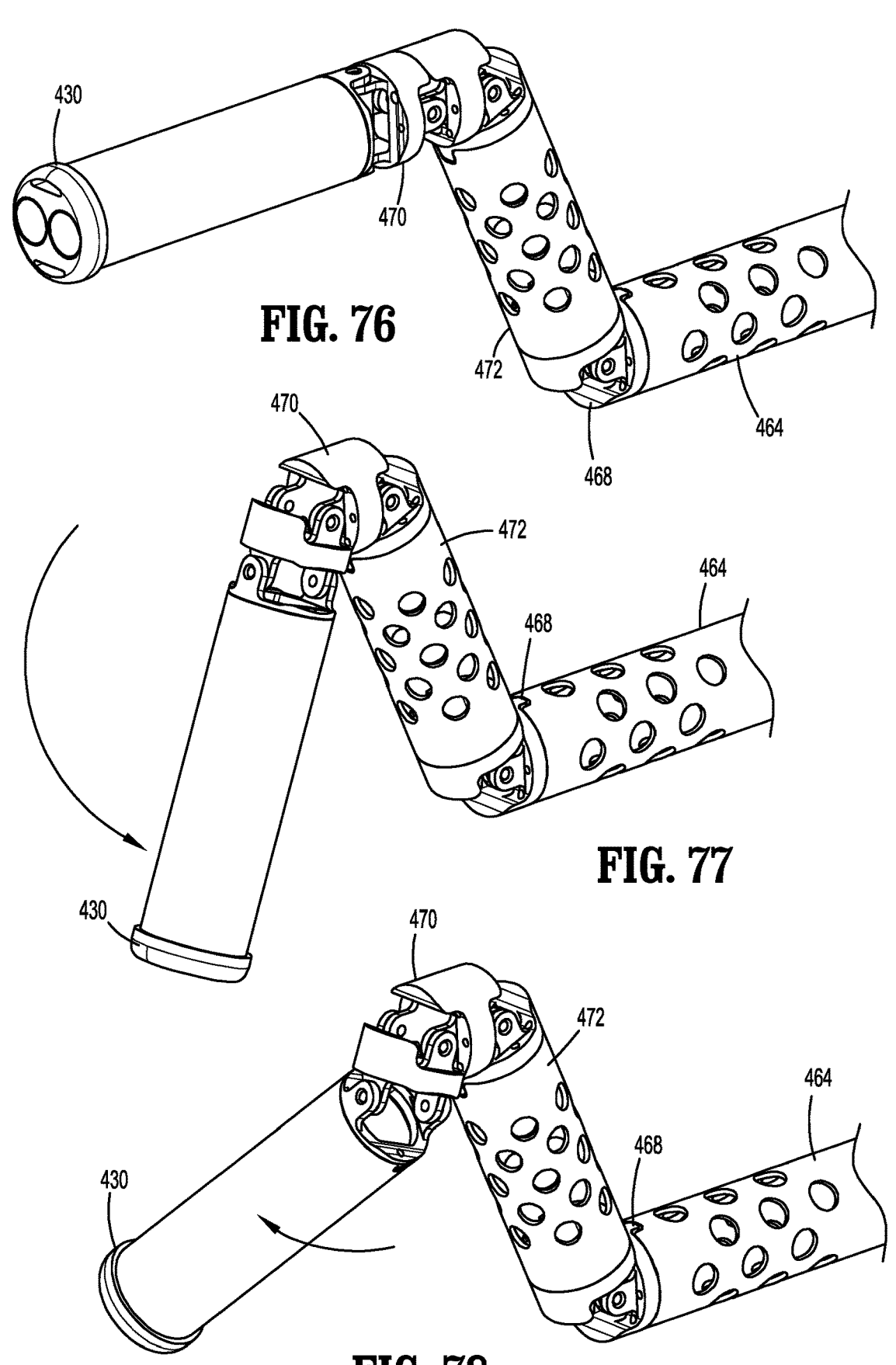
Figure 79:
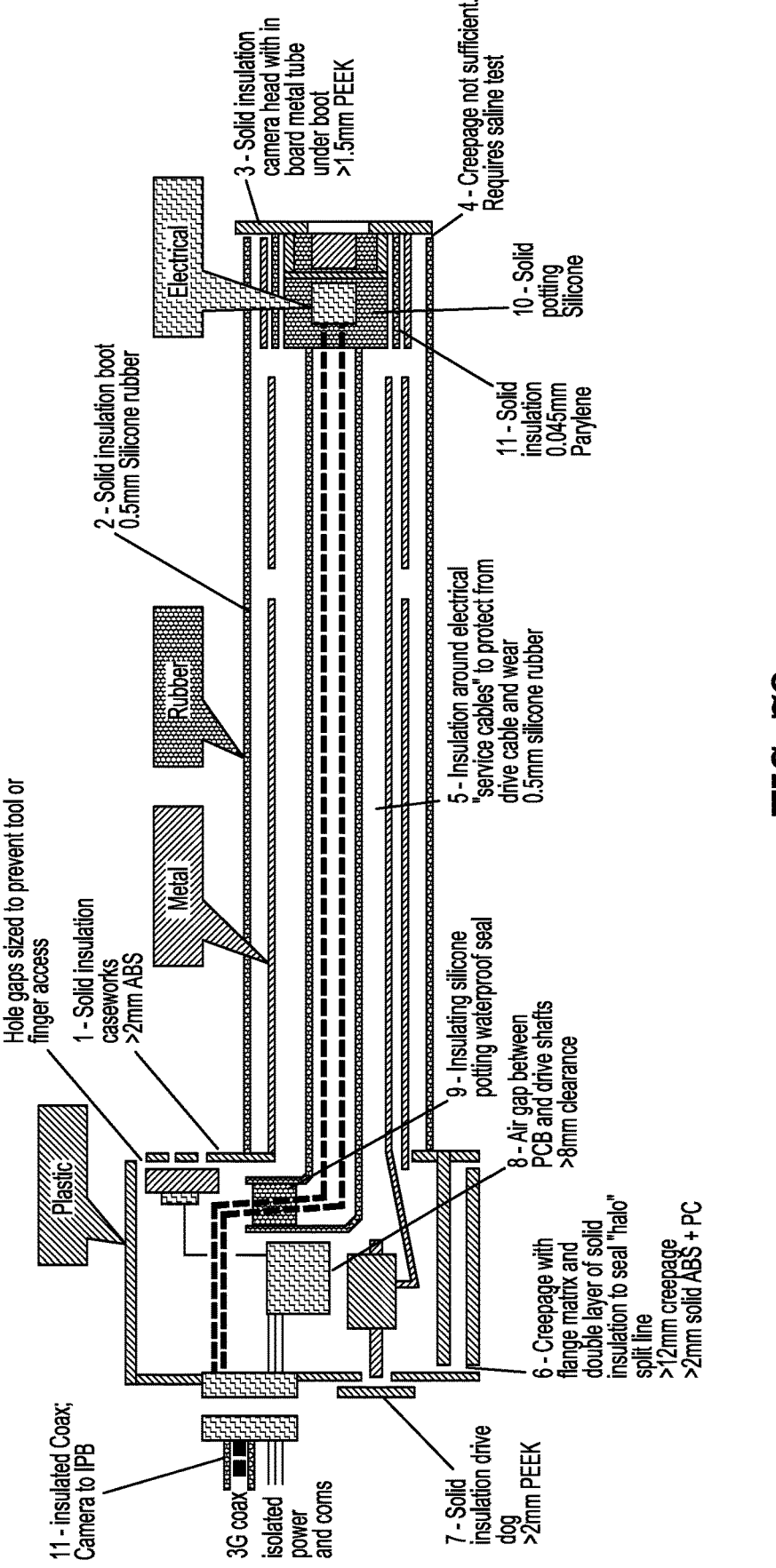

1 with portions thereof removed for clarity, the distal portion shown in an articulated position;

FIG. 27 is a perspective view of the distal portion of FIG. 26 in an unarticulated position;

FIG. 28 is a perspective view, with parts separated, of FIG. 27;

FIGS. 29A-33B show various enlarged, front and rear perspective views of links of the distal portion shown in FIG. 28;

FIG. 34 is a perspective view of a connector link of the distal portion shown in FIG. 28;

FIG. 35 is a cross-sectional view of the distal portion of the dexterous endoscope of FIG. 26 as taken along section line 26-26 shown in FIG. 26;

FIG. 36 is an enlarged, side view of the distal portion of the dexterous endoscope of FIG. 26 illustrating various tilt and elevated positions of the distal portion;

FIG. 37 is an enlarged, top view of the distal portion of the dexterous endoscope of FIG. 26 illustrating various pan positions of the distal portion;

FIG. 38 is a perspective view of a distal portion of yet another dexterous endoscope of the robotic surgical system of FIG. 1 with portions thereof removed for clarity, the distal portion shown in an articulated position;

FIG. 39 is a perspective view of the distal portion of FIG. 38 in an unarticulated position;

FIG. 40 is a perspective view, with parts separated, of FIG. 39;

FIGS. 41A-44B show various enlarged perspective views of links of the distal portion shown in FIG. 40;

FIG. 45 is a cross-sectional view of the distal portion of the dexterous endoscope of FIG. 38 as taken along section line 45-45 shown in FIG. 38;

FIG. 46 is a side view of the distal portion of the dexterous endoscope of FIG. 38 illustrating various tilt and elevate positions of the distal portion;

FIG. 47 is a top view of the distal portion of the dexterous endoscope of FIG. 38 illustrating various pan positions of the distal portion;

FIG. 48 is a perspective view of another dexterous endoscope with a distal portion thereof shown in an unarticulated position;

FIG. 49 is a side view of the dexterous endoscope of FIG. 48 with the distal portion shown in an articulated position;

FIG. 50 is a rear view of FIG. 49;

FIG. 51A is a perspective view of the dexterous endoscope of FIG. 48 with portions thereof removed or shown in phantom for clarity;

FIG. 51B is a perspective view, with parts separated, of FIG. 51A illustrating an electronics assembly thereof, a drive mechanism thereof, and a housing assembly thereof;

FIG. 51C is a side view of an elongated shaft of the housing assembly of FIG. 51B;

FIG. 52A is an enlarged, perspective view, with parts separated, of the electronics assembly of FIG. 51B;

FIG. 52B is an enlarged, perspective view, with parts separated, of a distal portion of the electronics assembly shown in FIG. 52A;

FIG. 52C is an enlarged, perspective view, with parts separated, of an electrical connector assembly of the robotic surgical system of FIG. 1;

FIG. 52D is an enlarged, top view illustrating a spring-biased pin of a pin plate of the electrical connector assembly of FIG. 52C;

FIG. 53 is an enlarged, perspective view, of a proximal portion of the drive mechanism of FIG. 51B;

FIG. 54 is a reduced, perspective view, with parts separated, of FIG. 53, the view illustrated with a cable assembly of the drive mechanism removed for clarity;

FIG. 55 is an enlarged, perspective view, with parts separated, of an elevate drive train of the drive mechanism shown in FIG. 54;

FIG. 56 is an enlarged, cross-sectional view, as taken along section line 56-56 of FIG. 53 illustrating a tilt drive train of the drive mechanism shown in FIG. 54;

FIG. 57 is a side view of FIG. 53;

FIG. 58 is a cross-sectional view as taken along section line 58-58 shown in FIG. 57;

FIG. 59 is an enlarged view of the indicated area of detail shown in FIG. 58;

FIG. 60 is a cross-sectional view as taken along section line 60-60 shown in FIG. 59;

FIG. 61 is a cross-sectional view as taken along section line 61-61 shown in FIG. 57;

FIG. 62 is a cross-sectional view as taken along section line 62-62 shown in FIG. 57;

FIG. 63 is a cross-sectional view as taken along section line 63-63 shown in FIG. 57;

FIG. 64 is a cross-sectional view as taken along section line 64-64 shown in FIG. 57;

FIG. 65 is a cross-sectional view as taken along section line 65-65 shown in FIG. 57;

FIGS. 66 and 67 are enlarged, perspective views of a distal portion of the dexterous endoscope of FIG. 48 with portions thereof shown in phantom or removed for clarity;

FIG. 68 is a perspective view, with parts separated, of FIG. 67;

FIGS. 69-78 are various views illustrating ranges of motion of the distal portion of the dexterous endoscope of FIG. 48; and FIG. 79 is a schematic view of aspects of one dexterous endoscope in accordance with the principles of this disclosure.

DETAILED DESCRIPTION

Aspects of this disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel and/or equipment operators.

In the following description, well-known functions or constructions are not described in detail to avoid obscuring the present disclosure in unnecessary detail.

Robotic surgical systems have been used in minimally invasive medical procedures and can include robotic arm assemblies. Such procedures may be referred to as what is commonly referred to as "Telesurgery." Some robotic arm assemblies include one or more robot arms to which surgical instruments can be coupled. Such surgical instruments include, for example, endoscopes, electrosurgical forceps, cutting instruments, staplers, graspers, electrocautery devices, or any other endoscopic or open surgical devices. Prior to or during use of the robotic surgical system, various surgical instruments can be selected and connected to the robot arms for selectively actuating end effectors of the connected surgical instruments.

With reference to FIGS. 1-7, a robotic surgical system is shown generally at 10. Robotic surgical system 10 employs various robotic elements to assist the clinician and allow remote operation (or partial remote operation) of surgical instrumentation such as endoscope 100. Various robotic arms, gears, cams, pulleys, electric and mechanical motors, etc. may be employed for this purpose and may be designed with surgical system 10 to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

Robotic surgical system 10 includes a workstation 12 and an instrument cart 14. The instrument cart 14 includes an instrument assembly 16 mounted on a moveable drive unit 18 that houses a drive assembly such as an instrument drive assembly or an endoscope drive assembly 20 for manipulating the instrument assembly 16 and/or independent surgical instruments thereof. The instrument drive assembly or endoscope drive assembly 20 may include a respective drive for selectively imparting drive forces to respective surgical instruments or endoscopes. The surgical instruments can include, for example, graspers 26 (e.g., three separate graspers) and an endoscope 100 that are driven by one or more associated tool drives (not shown) of endoscope drive assembly 20. The instrument assembly 16 includes an insertion tube 16a defining a plurality of separate conduits, channels or lumens 16b therethrough that are configured to receive, for instance, the graspers 26 and the endoscope 100 for accessing a body cavity "BC" of a patient "P." In other aspects, the insertion tube 16a may define a single conduit, channel or lumen therethrough that is configured to receive, for instance, the graspers 26 and the endoscope 100 for accessing a body cavity "BC" of a patient "P." In particular, the insertion tube 16a can be inserted through an incision "I" and/or access device 17 (e.g., a surgical portal, which may include or more seals to facilitate sealed insertion through tissue "T" of the patient "P") and into the body cavity "BC" of the patient "P"). With insertion tube 16a positioned in the patient "P," the graspers 26 and/or the endoscope 100 can be advanced through insertion tube 16a into the body cavity "BC" of the patient "P." Further, the workstation 12 includes an input device 22 for use by a clinician for controlling the insertion tube 16a and the various surgical instruments of instrument assembly 16 via the instrument drive assembly or endoscope drive assembly 20 to perform surgical operations on the patient "P" while the patient "P" is supported on a surgical table 24, for example. Input device 22 is configured to receive input from the clinician and produces input signals. Input device 22 may also be configured to generate feedback to the clinician. The feedback can be visual, auditory, haptic, or the like.

The workstation 12 can further include a master processor circuit 22a in communication with the input device 22 for receiving the input signals and generating control signals for controlling the robotic surgical system 10, which can be transmitted to the instrument cart 14 via an interface cable 22b. In some cases, transmission can be wireless and interface cable 22b may not be present. The input device 22 can include right and left-hand controllers (not shown) and/or foot pedals (not shown), which are moved/operated to produce input signals at the input device 22 and/or to control robotic surgical system 10. The instrument cart 14 can include a slave processor circuit 20a that receives and the control signals from the master processor circuit 22a and produces slave control signals operable to control the instrument insertion and visualization devices such as endoscope

100 and one or more instruments such as graspers 26 (and their respective end effectors) during a surgical procedure. Besides graspers 26 and endoscope 100, the one or more surgical instruments can include dexterous tools, such as grippers, needle drivers, staplers, dissectors, cutters, hooks, graspers, scissors, coagulators, irrigators, suction devices, that are used for performing a surgical procedure. While both master and slave processor circuits are illustrated, in other embodiments a single processor circuit may be used to perform both master and slave functions. The workstation 12 can also include a user interface, such as a display (not shown) in communication with the master processor circuit 22a for displaying information (such as, body cavity images) for a region or site of interest (for example, a surgical site, a body cavity, or the like) and other information to a clinician.

Figure 6:
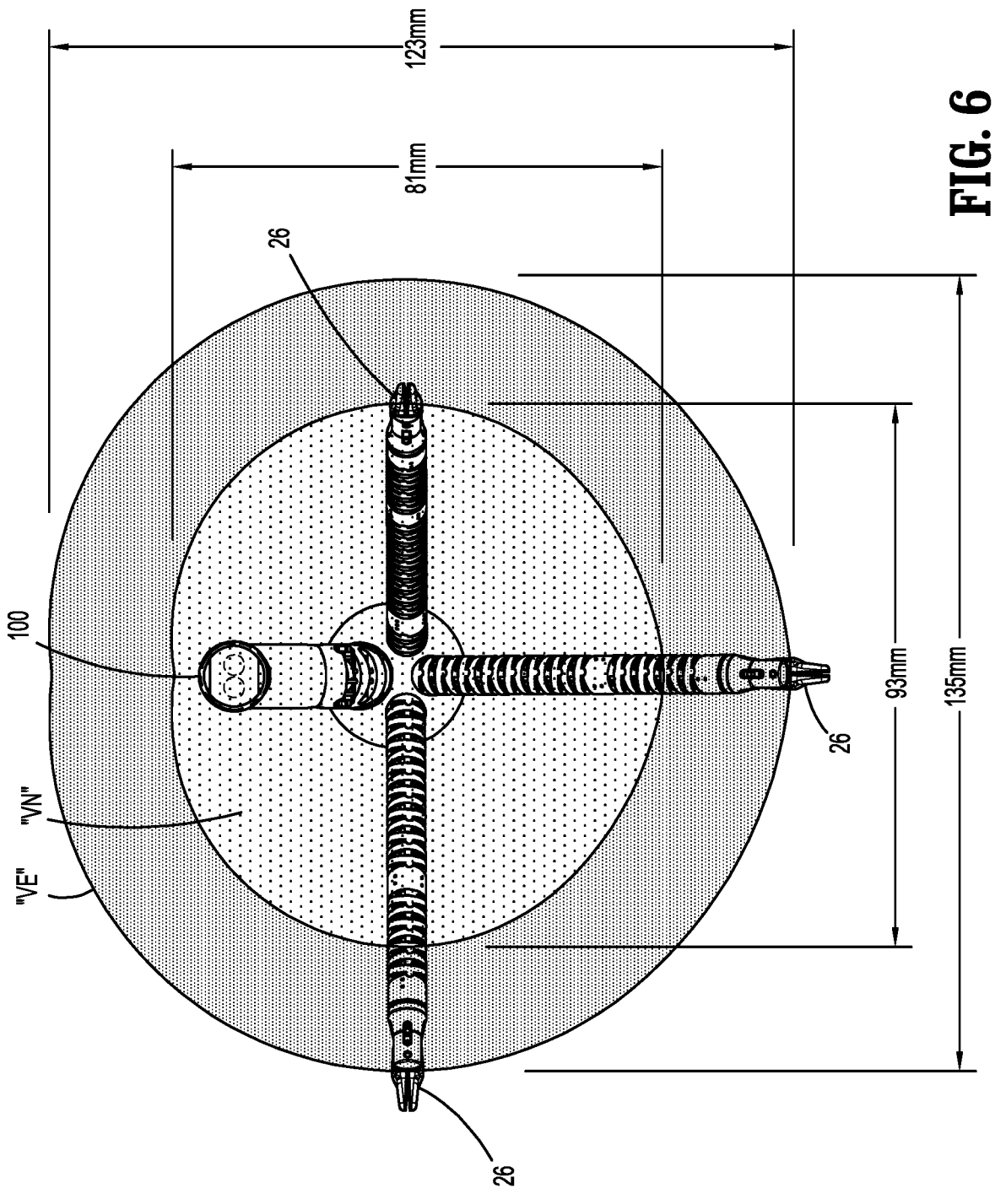
Figure 7:
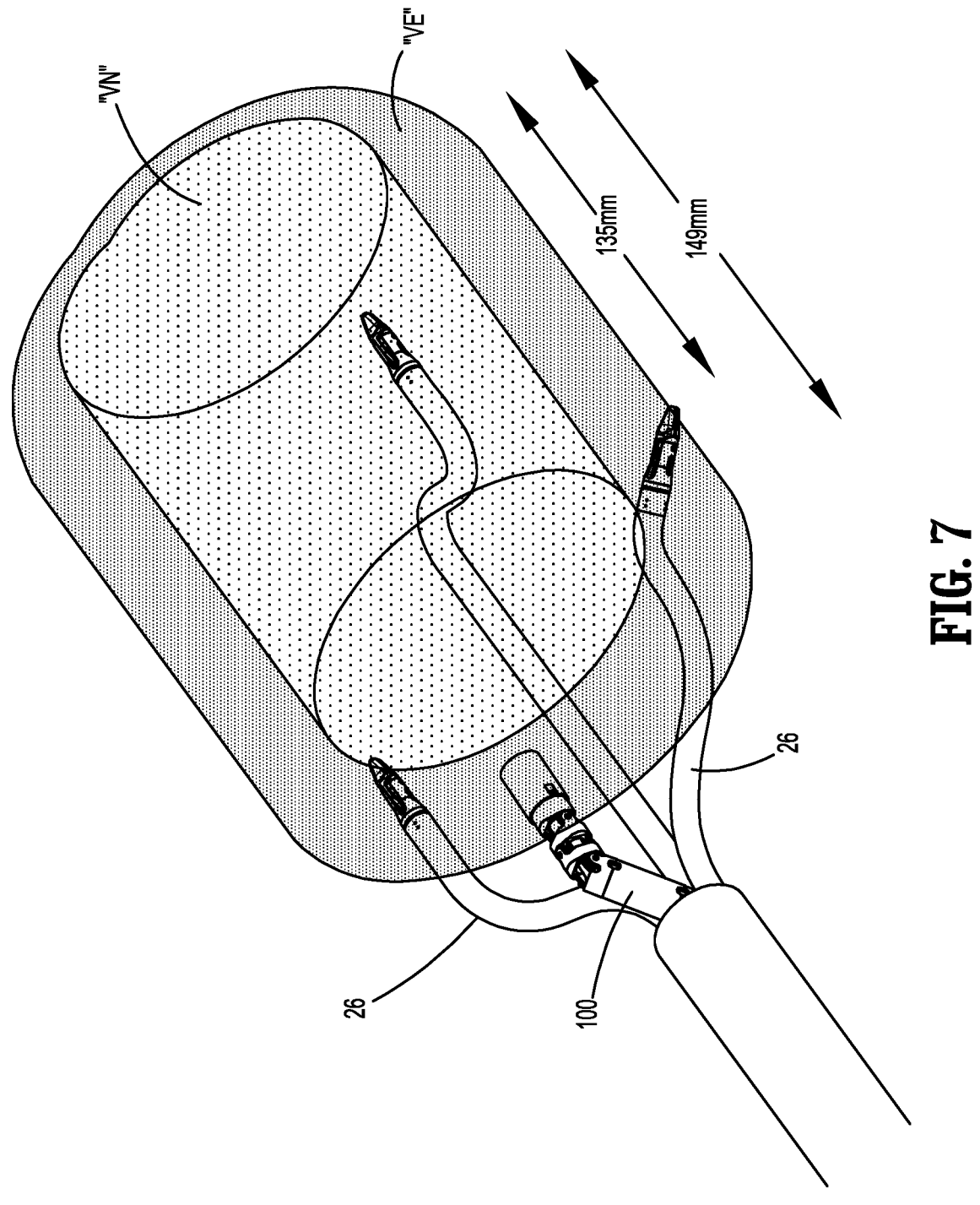

Advantageously, the present disclosure describes a dexterous endoscope 100 that provides extreme wrist or articulating movement in panning, tilting, and elevating directions (see FIG. 5) to enable a larger workspace field of view than prior endoscopes that have limited wrist or articulating movement, if any, by comparison. As seen in FIGS. 6 and 7, a normal workspace field of view "VN" for prior endoscopes typically has a maximum diameter of about 93 mm and a maximum length of about 135 mm, whereas the dexterous endoscope 100 of this disclosure provides an extreme workspace field of view "VE" having a maximum diameter of at least about 135 mm and a maximum length of at least about 149 mm. The dexterous endoscope 100 of this disclosure also provides a short camera module, a reduced fiber-optic bundle, and a powered elevation feature. Accordingly, the dexterous endoscope 100 provides increased clinician control, flexibility, and durability.

Figures 8, 9:
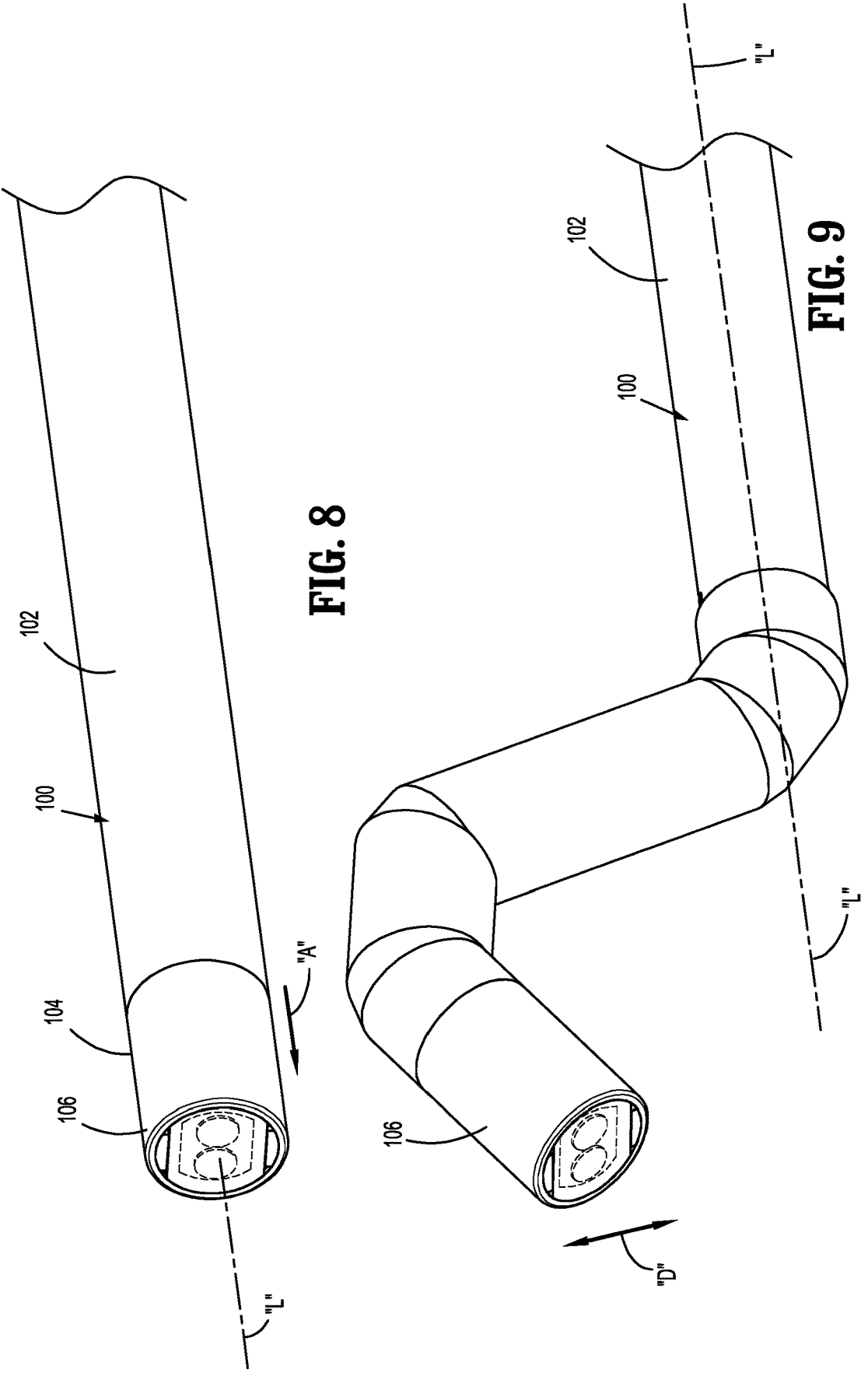
FIG. 8 is an enlarged, perspective view of a distal portion of a dexterous endoscope of the endoscopic system of FIGS. 2-4, the distal portion shown in an unarticulated position.
FIG. 9 is a perspective view of the distal portion of the dexterous endoscope shown in FIG. 8, the distal portion shown in one articulated position.
Figure 22:
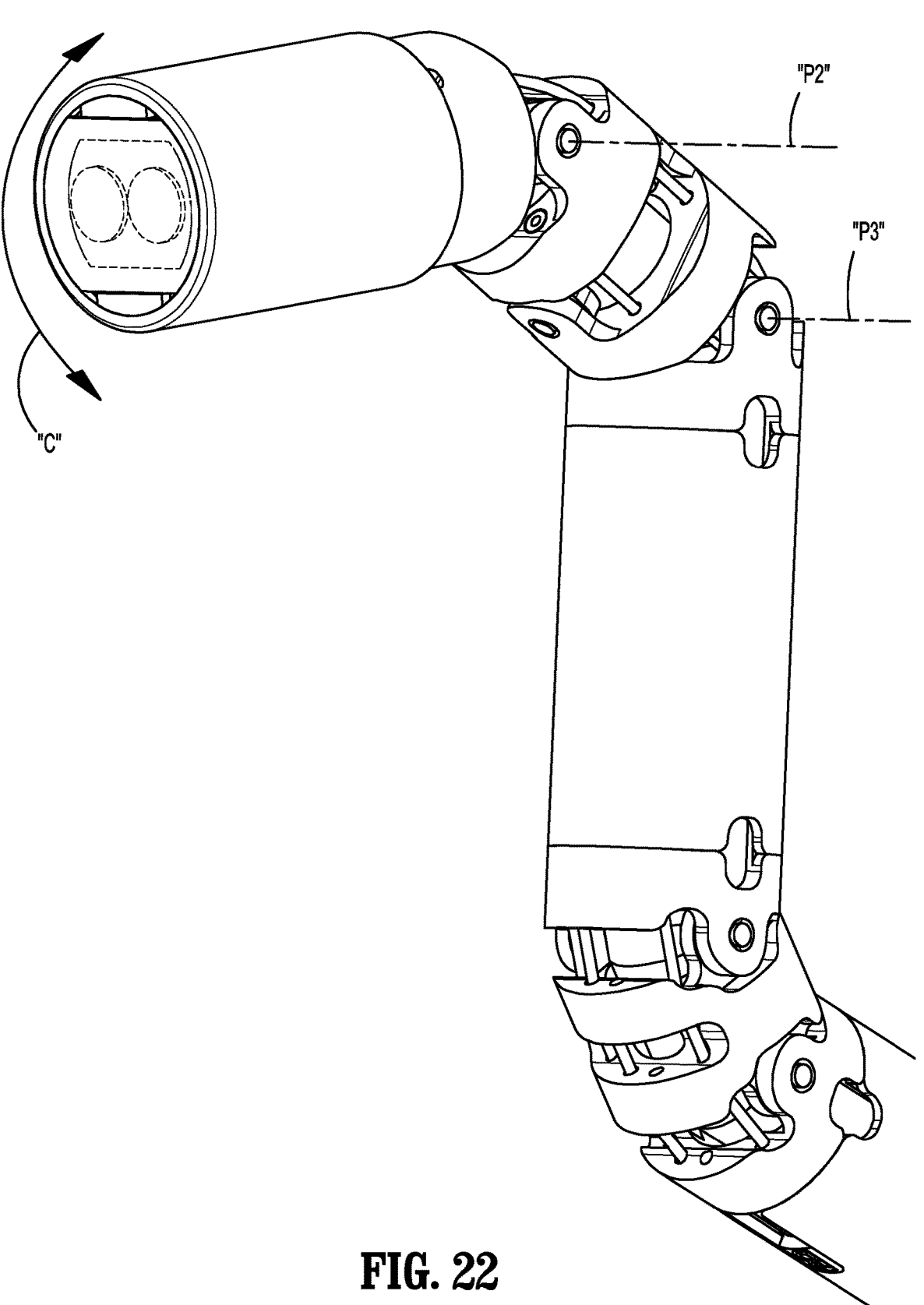
FIGS. 22 and 23 are enlarged, perspective views of the distal portion of the endoscopic system of FIGS. 2-4 shown in another articulated position.
Figure 23:
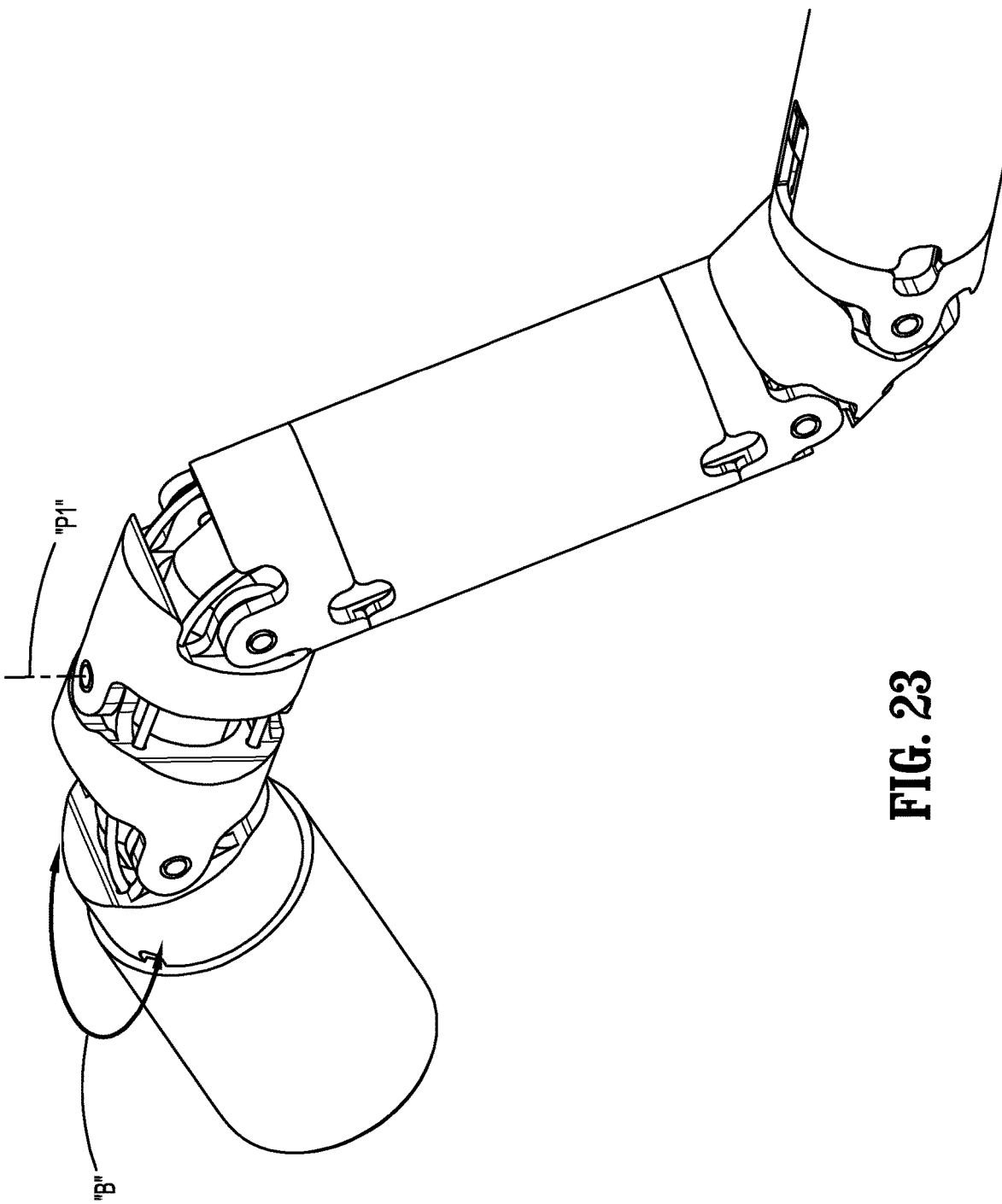
Figure 24:
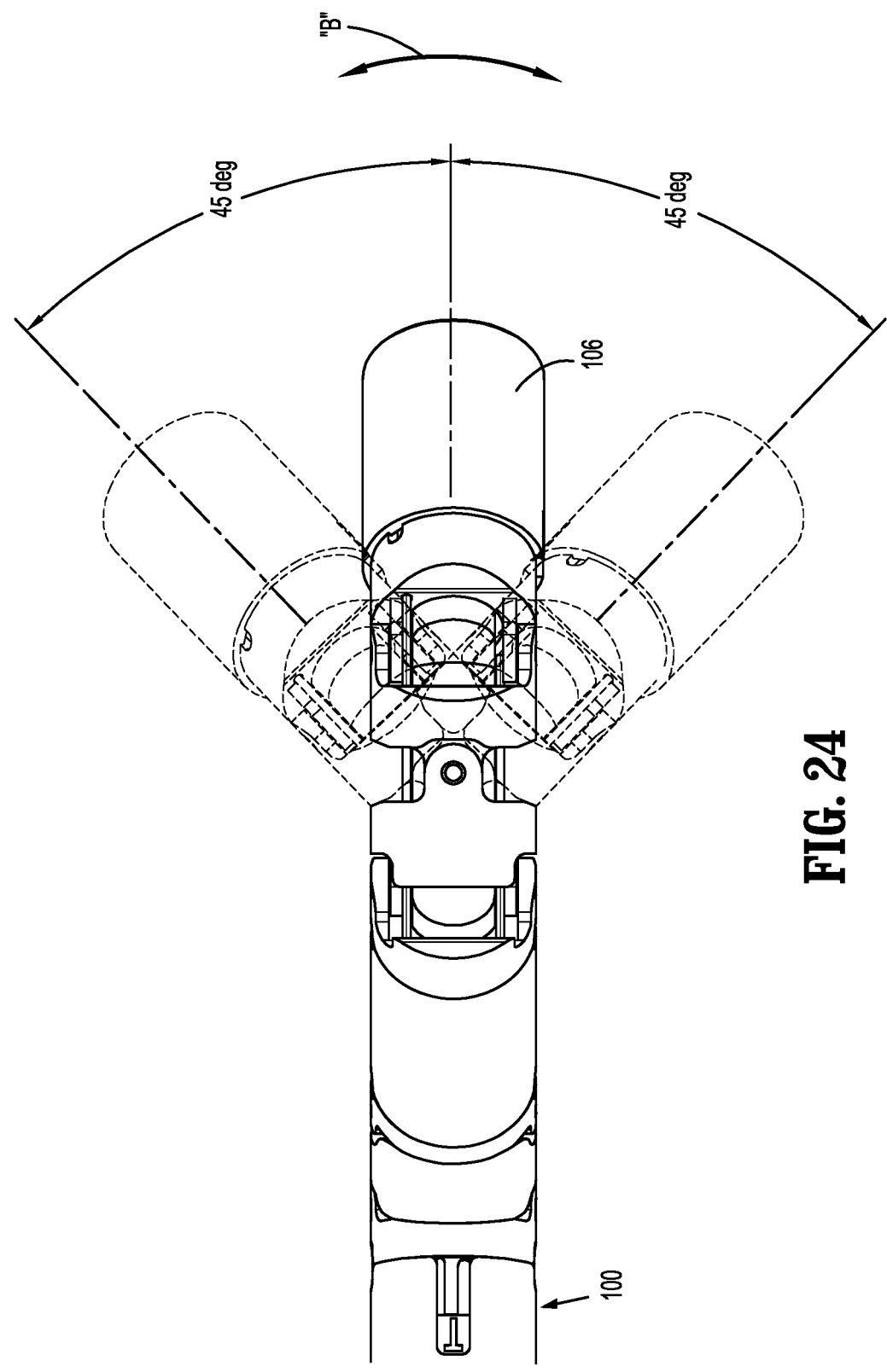
FIG. 24 is an enlarged, top view of the distal portion of the dexterous endoscope of FIG. 8 illustrating various pan positions of the distal portion.

Turning now to FIGS. 8 and 9, endoscope 100 defines a central longitudinal axis "L" and includes an elongated shaft assembly having an outer sleeve 102 and an inner shaft assembly 104 that extends distally from outer sleeve 102 to a camera assembly 106. Inner shaft assembly 104 is axially movable along longitudinal axis "L" (e.g., relative to outer sleeve 102), as indicated by arrow "A" to adjust a length of endoscope 100. In addition, inner shaft assembly 104 is also configured to enable camera assembly 106 articulate relative to the longitudinal axis "L." For example, the inner shaft assembly 104 can enable camera assembly 106 to pan relative to longitudinal axis "L" and/or outer sleeve 102 (e.g., lateral pivoting movement about first pivot axis "P1" as seen in FIG. 23 and as indicated by arrows "B" in FIGS. 23 and 24), tilt relative to longitudinal axis "L" and/or outer sleeve 102 (e.g., vertical pivoting movement about second pivot axis "P2" and third pivot axis "P3" as seen in FIG. 22 and as indicated by arrows "C" in FIGS. 22 and 25), and/or elevate/descend relative to longitudinal axis "L" and/or outer sleeve 102 (e.g., vertical movement relative to the longitudinal axis "L" as indicated by arrows "D" in FIG. 9).

Figure 11:
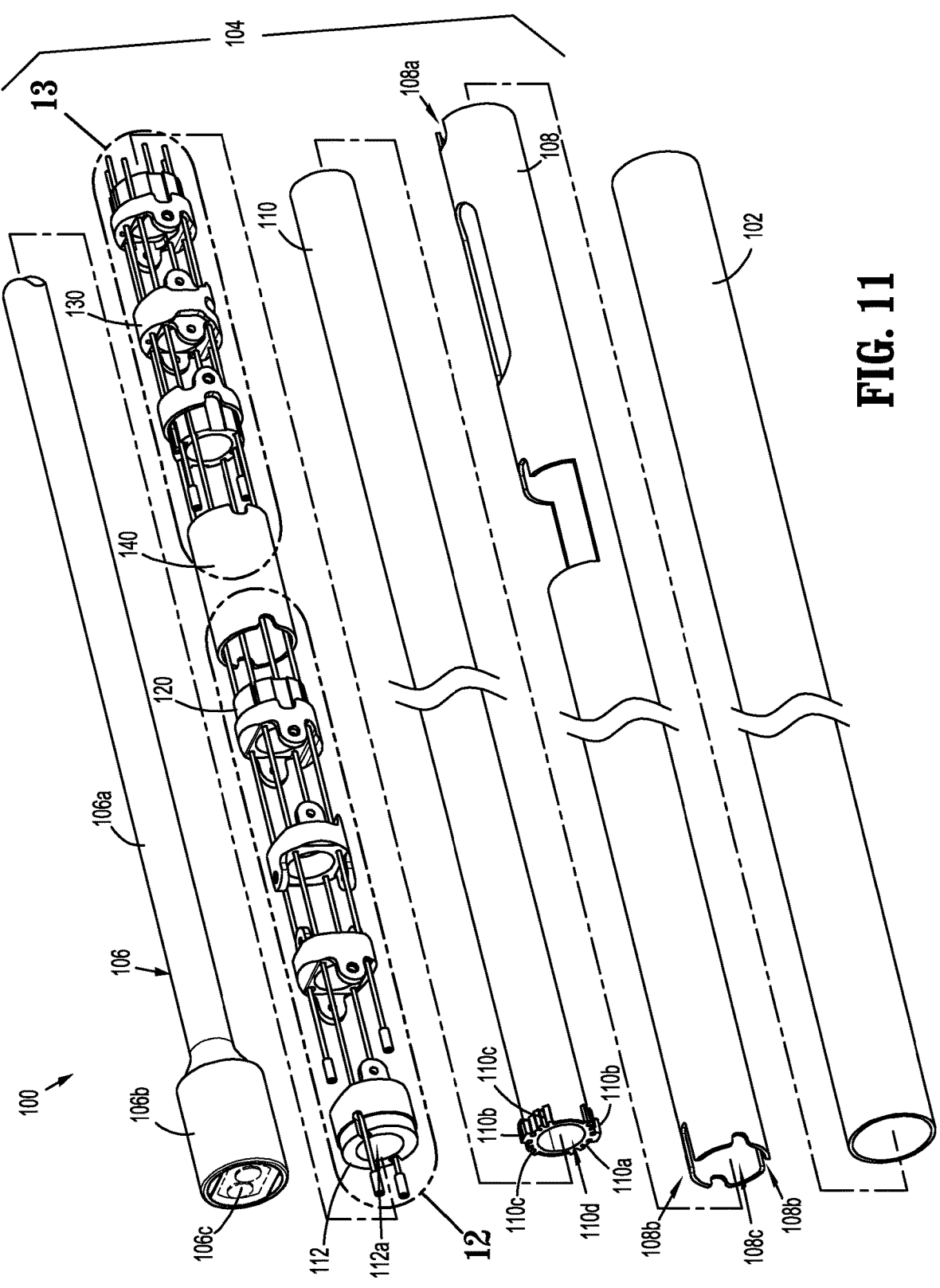
FIG. 11 is a perspective view, with parts separated, of the distal portion of FIG. 8.

With reference to FIG. 11, inner shaft assembly 104 of endoscope 100 includes an outer shaft 108 and an inner shaft 110 received within a central lumen 108c outer shaft 108. Inner shaft assembly 104 further includes an articulation assembly 112 coupled to a distal end portion of inner shaft 110, and the camera assembly 106. Camera assembly 106 has a flexible sleeve 106a received within a central lumen 112a of articulation assembly 112 and received within a central lumen 110d defined through inner shaft 110d. Camera module assembly 106 further includes a compact camera 106b on a distal end portion of flexible sleeve 106a and which is positioned to extend distally from a distal end portion of articulation assembly 112. Outer shaft 108 defines proximal notches 108a in a proximal end portion thereof and distal notches 108b in a distal end portion thereof. Inner shaft 110 extends distally to a distal guide ring 110a having alignment teeth 110b on diametrically opposed ends thereof. Distal guide ring 110a further defines a plurality of articulation cable channels 110c along an outer radial surface of guide ring 110a. Alignment teeth 110b are positioned to be received within distal notches 108b of outer shaft 108 to prevent inner shaft 110 from rotating relative to outer shaft 108.

Compact camera 106b of camera assembly 106 further includes one or more cameras 106c positioned at a distal end portion of compact camera 106b. Cameras 106c are operatively coupled to one or more data cables (not shown), such as fiber optic bundles, that extend through camera assembly 106 and can be used to transmit control signals and data, such as analog or digital image data provided by the one or more cameras 106c to the workstation 12 and/or instrument cart 14. In some cases, transmission can be wireless.

Figure 10:
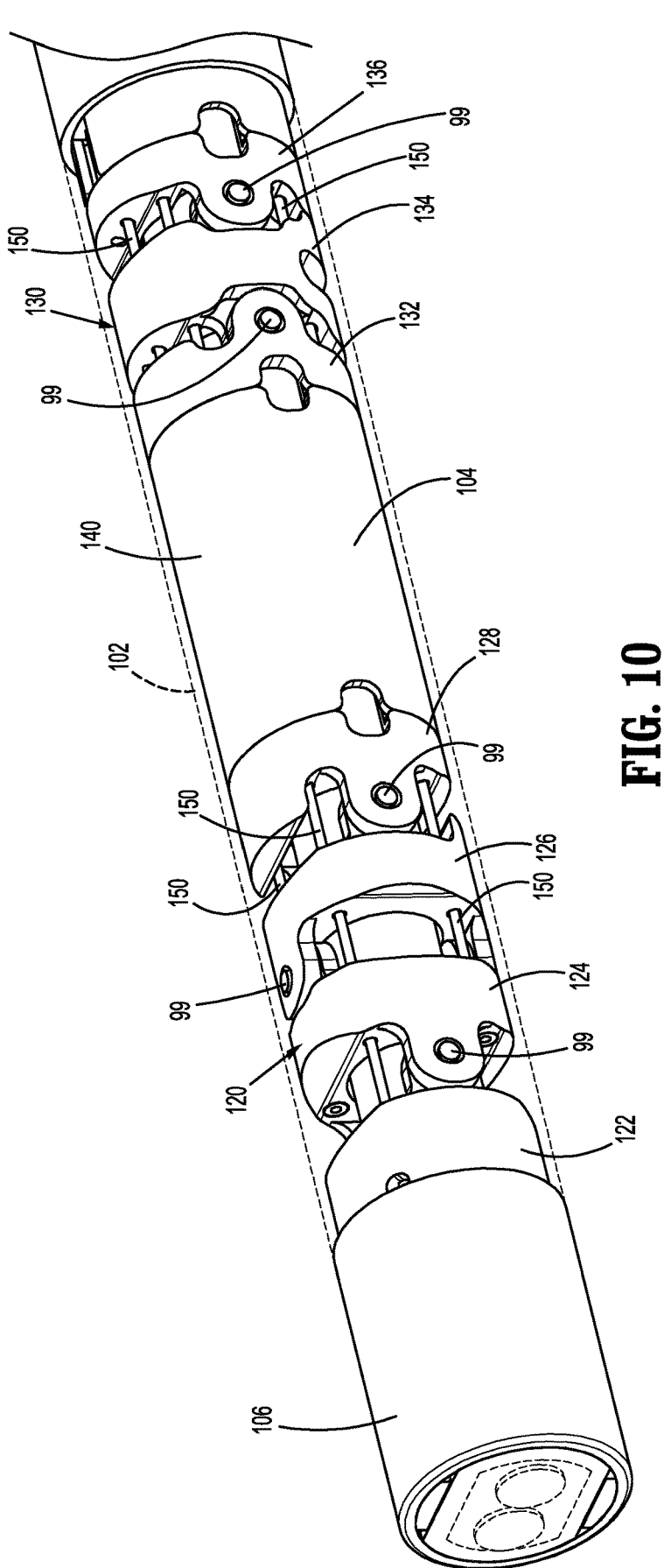
FIG. 10 is an enlarged, perspective view of FIG. 8 with an outer sleeve of the distal portion shown in phantom for clarity.
Figures 12, 13:
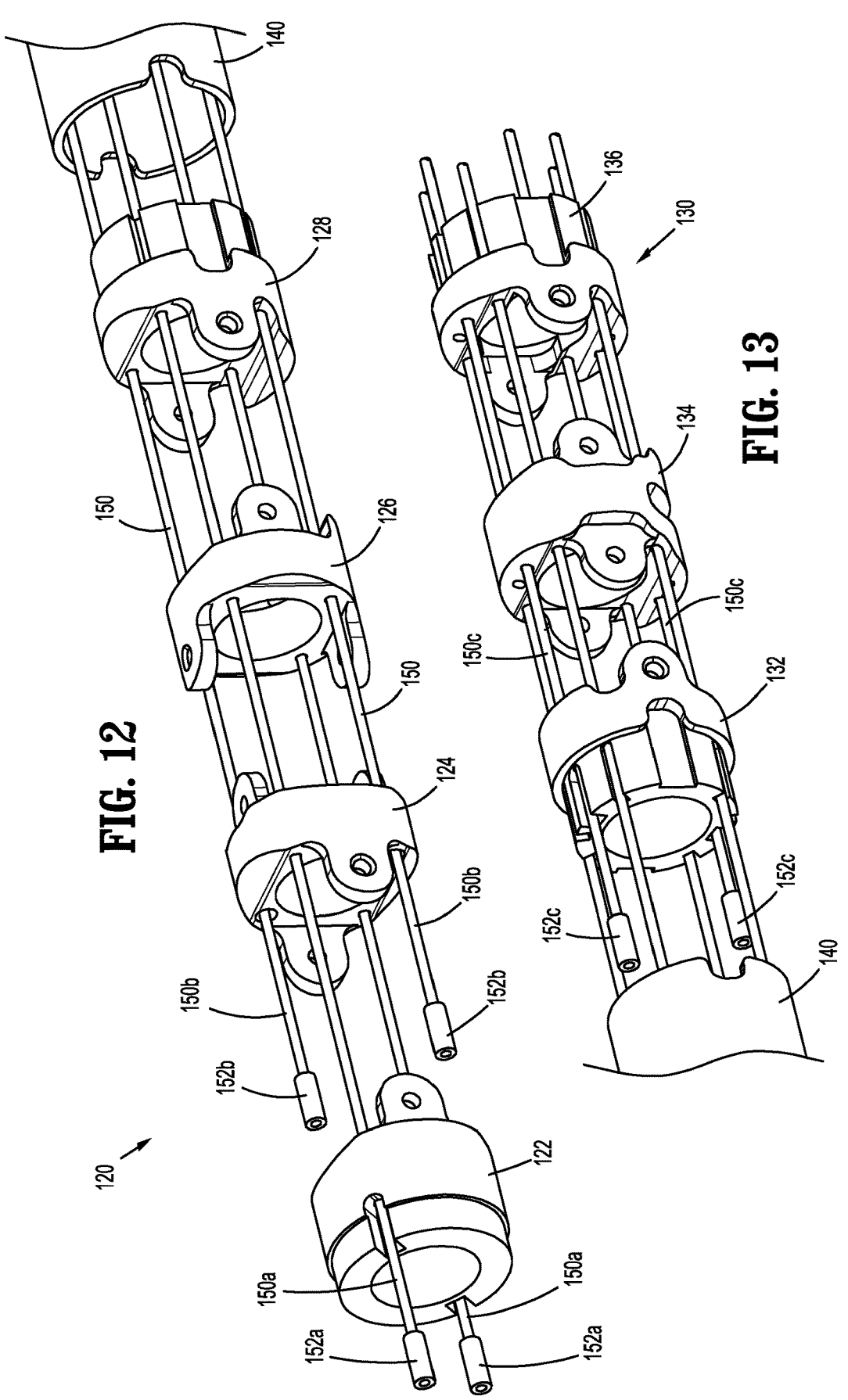
FIGS. 12 and 13 are enlarged, perspective views of the indicated areas of detail shown in FIG. 11.

With reference to FIGS. 10-12, articulation assembly 112 of inner sleeve assembly 104 further includes a distal wrist assembly 120, a proximal wrist assembly 130, and a connector tube 140 that connects the distal and proximal wrist assemblies 120, 130 together. Articulation assembly 112 further includes a plurality of articulation cables 150 supporting ferrules 152 on distal ends thereof that facilitate articulating movement of articulation assembly 112 relative to longitudinal axis "L" and/or outer sleeve 102 for articulating camera assembly 106 within the patient "P" to change the field of view within the body cavity "BC" in the patient "P" (see FIGS. 2-7). Distal and proximal wrist assemblies 120, 130 are also pinned together by a plurality of pins 99 disposed in transverse (e.g., orthogonal) and/or parallel relation to one another to enable adjacent components (e.g., links, distal head, connector tube, etc.) of articulation assembly 112 to pivot relative to, and/or with, one another to enable camera assembly 106 to pan, tilt, and/or elevate/descend relative to a central axis "L" defined by endoscope 100 (see FIGS. 8 and 9) in response to coordinated axial movement (e.g., proximal/tightening and/or distal/loosening movement) of one or more of the articulation cables of the plurality of articulation cables 150 relative to, and/or with, one another. Such movement is effectuated by actuation of one or more drive mechanisms such as instrument drive assembly or endoscope drive assembly 20 of robotic surgical system 10.

Distal wrist assembly 120 of articulation assembly 112 includes a distal head link 122 on a distal end portion thereof, a distal link 124 disposed proximal to the distal head link 122, an intermediate link 126 disposed proximal to distal link 124, and a proximal link 128 disposed proximal to intermediate link 126 and distal to connector tube 140. A distal portion of distal head link 122 is engaged with compact camera 106b of camera assembly 106 and a proximal portion of distal head link 122 is pinned to a distal portion of distal link 124. A proximal portion of distal link 124 is pinned to a distal portion of intermediate link 126 and a proximal portion of intermediate link 126 is pinned to a distal portion of proximal link 128. A proximal portion of proximal link 128 is received within a distal portion of connector tube 140 (e.g., frictionally-fit).

Proximal wrist assembly 120 of articulation assembly 112 includes a distal link 132 disposed proximal to connector tube 140, an intermediate link 134 disposed proximal to the distal link 132, and a proximal link 136 disposed proximal to intermediate link 134. A distal portion of distal link 132 is received within a proximal portion of connector tube 140

(e.g., frictionally-fit) and a proximal portion of distal link 132 is pinned to a distal portion of intermediate link 134. A proximal portion of intermediate link 134 is pinned to a distal portion of proximal link 136. A proximal portion of proximal link 136 is positioned to be received within a distal end portion of central lumen 108c of outer shaft 108 of inner sleeve assembly 104 (e.g., frictionally-fit). Proximal link 126 is disposed distally adjacent to distal guide ring 110a of inner shaft 110 of inner sleeve assembly 104.

With reference to FIGS. 14A and 14B, distal head link 122 of distal wrist assembly 120 defines ferrule pockets 122a in an outer surface of a distal portion thereof for receiving ferrules 152a of a first pair of articulating cables 150a of the plurality of articulating cables 150 and inner proximal pivot tabs 122b that extend from a proximal portion thereof. Ferrules 152a secure distal portions of articulating cables 150a to distal head link 122. Inner proximal pivot tabs 122b define pin holes 122c therethrough for receiving a pin 99 (see FIG. 10) therein to pivotably couple distal head link 122 to distal link 124. Distal head link 122 further defines a central lumen 122d therethrough for receiving flexible sleeve 106a of camera assembly 106 and cable passages 122e therethrough for slidably receiving articulation cables 150. Cable passages 122e are disposed in registration with ferrule pockets 122a.

Figure 25:
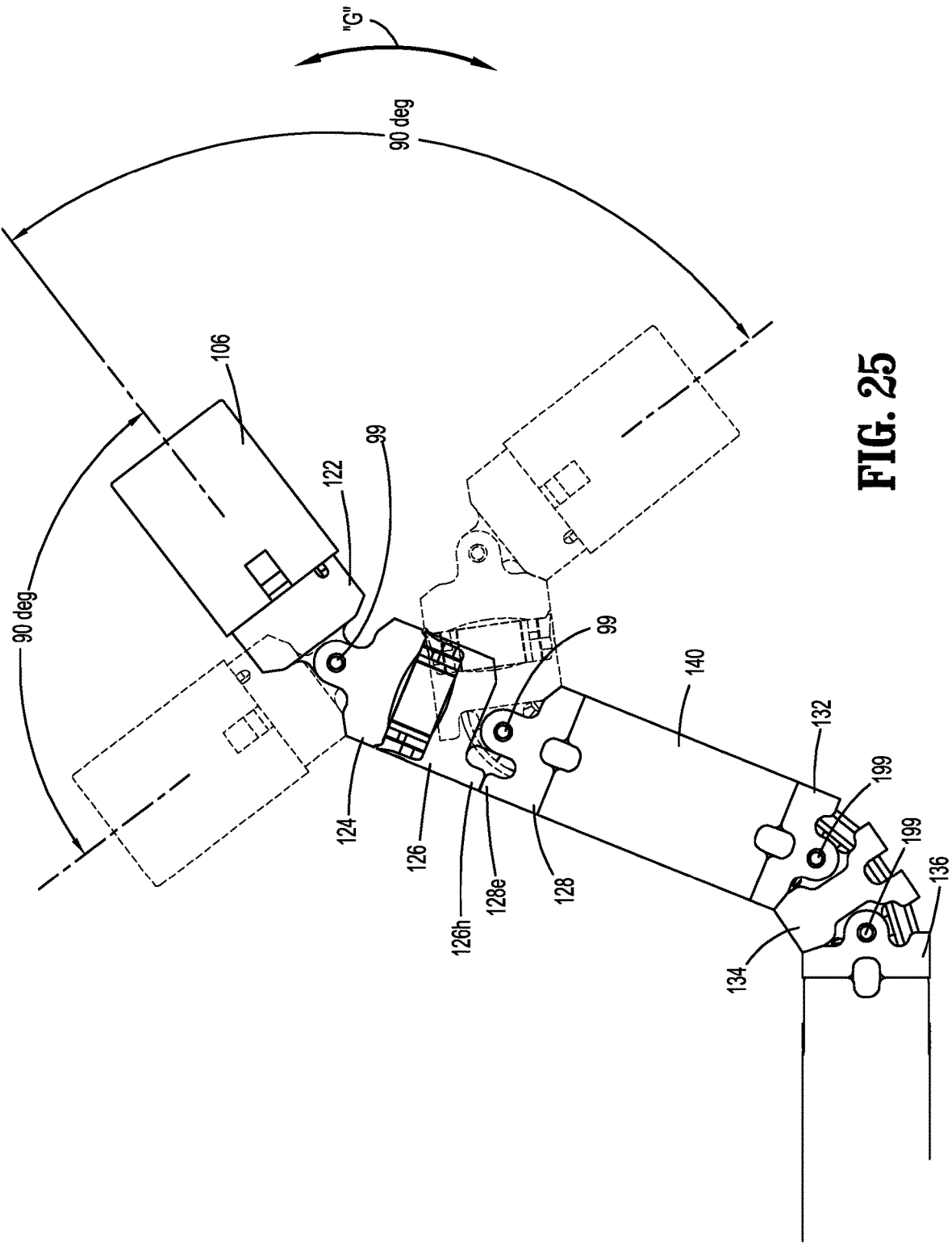
FIG. 25 is an enlarged, side view of the distal portion of the dexterous endoscope of FIG. 8 illustrating various tilt and elevate positions of the distal portion.

As seen in FIGS. 15A and 15B, distal link 124 of distal wrist assembly 120 includes outer distal pivot tabs 124a defining pin holes 124b therethrough for receiving the pin 99 (see FIG. 10) that pivotably couples distal link 124 to distal head link 122 when outer distal pivot tabs 124a are aligned with (e.g., disposed adjacent to) inner proximal pivot tabs 122b of distal head 122. Distal link 124 further defines a central lumen 124c therethrough for receiving flexible sleeve 106a of camera assembly 106. A distal portion of distal link 124 also defines ferrule pockets 124d for receiving ferrules 152b of a second pair of articulating cables 150b of the plurality of articulating cables 150 so that the second pair of articulating cables 150b and ferrules 152b thereof are longitudinally offset from (e.g., proximal to) the first pair of articulating cables 150a and ferrules 152a. This offset arrangement enables distal head link 122 to move (e.g., pivot/tilt) relative to distal link 124 as seen in FIG. 25 as one or both of first pair of articulating cables 150a are axially moved (e.g., distally/loosening and/or proximally/tightening) relative to distal link 124. Ferrules 152b secure distal portions of the second pair of articulating cables 150b to distal link 124. Distal link 124 further defines cable passages 124e therethrough for slidably receiving the first pair of articulating cables 150a (from distal head link 122) therethrough. Distal link 124 also defines cable passages 124f in a proximal portion thereof that are disposed in registration with ferrule pockets 124d to slidably receive the second pair of articulation cables 150b therethrough. Distal link 124 also includes inner proximal pivot tabs 124g defining pin holes 124h therethrough for receiving a pin 99 (see FIG. 10) that pivotably couples distal link 124 to intermediate link 126 of distal wrist assembly 120. Proximal pivot tabs 124g are transverse to outer distal pivot tabs 124a.

Figure 16A:
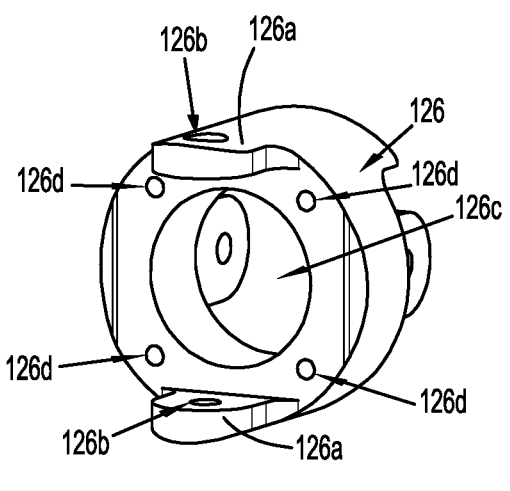
Figure 16B:
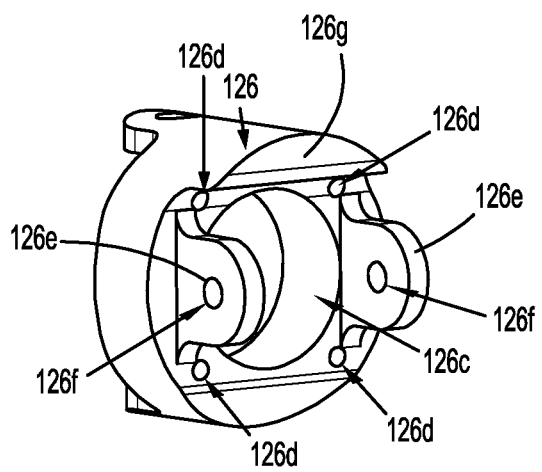

With reference to FIGS. 16A and 16B, intermediate link 126 of distal wrist assembly 120 includes outer distal pivot tabs 126a defining pin holes 126b therethrough for receiving the pin 99 (see FIG. 10) that pivotably couples intermediate link 126 to distal link 124 when outer distal pivot tabs 126a are aligned with (e.g., disposed adjacent to) inner proximal pivot tabs 124g of distal link 124. Intermediate link 126 further defines a central lumen 126c for receiving flexible sleeve 106a of camera assembly 106 and a plurality of cable passages 126d therethrough for slidably receiving articulation cables 150. Intermediate link 126 includes proximal pivot tabs 126e defining pin holes 126f therethrough for receiving a pin 99 (see FIG. 10) that pivotably couples intermediate link 126 to proximal link 128. Inner proximal pivot tabs 126e are disposed transverse to outer distal pivot tabs 126a. Intermediate link 126 further includes a proximal abutment shoulder 126h extending from one side of a proximal end portion thereof to limit proximal tilting movement of intermediate link 126 relative to proximal link 128 as seen in FIG. 25.

Figure 17A:
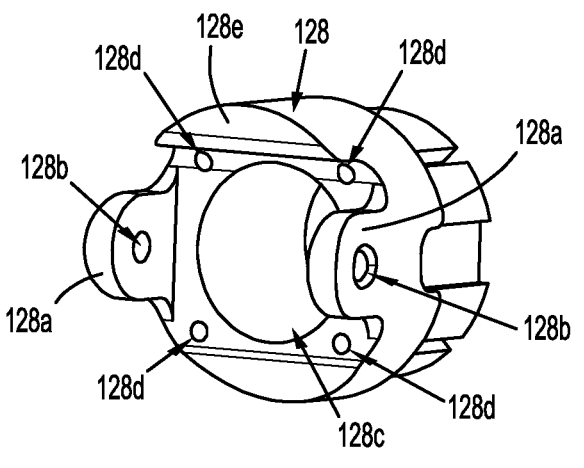
Figure 17B:
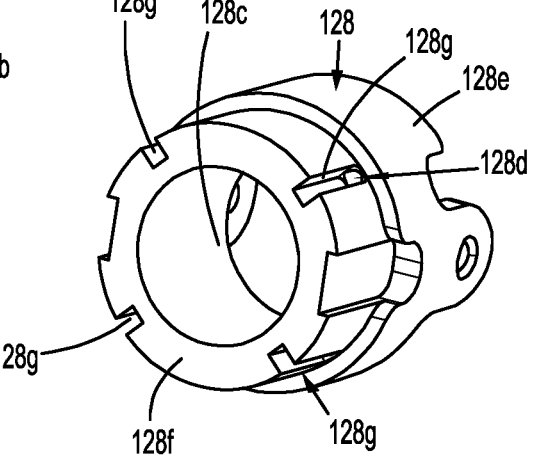

Turning now to FIGS. 17A, 17B and 18, proximal link 128 of distal wrist assembly 120 includes outer distal pivot tabs 128a defining pin holes 128b therethrough for receiving the pin 99 (see FIG. 10) that pivotably couples intermediate link 126 to proximal link 128 when outer distal pivot tabs 128a are aligned with (e.g., disposed adjacent to) inner proximal pivot tabs 126e of intermediate link 126. Proximal link 128 further defines a central lumen 128c for receiving flexible sleeve 106a of camera assembly 106 and a plurality of cable passages 128d therethrough for slidably receiving articulation cables 150. Proximal link 128 also includes a distal abutment shoulder 128e extending from one side of a distal end portion thereof and positioned to engage proximal abutment shoulder 126h of intermediate link 126 for limiting tilting movement of intermediate link 126 relative to proximal link 128. Proximal link 128 further includes a proximal connector protrusion 128f extending proximally therefrom for coupling proximal link 128 to a distal portion of connector tube 140. Proximal connector protrusion 128f of proximal link 128 is received within a distal portion of a central lumen 140a of connector tube 140 (e.g., frictionally-fit) and defines a plurality of cable channels 128g in registration with cable passages 128d for slidably receiving articulation cables 150. Central lumen 140a of connector tube 140 is configured to receive articulation cables 150 and flexible sleeve 106a of camera assembly 106 therethrough.

With reference to FIGS. 13, 18, 19A, and 19B, distal link 132 of proximal wrist assembly 130 includes a distal connector protrusion 132a that is received with a proximal portion of the central lumen 140a of connector tube 140 (e.g., frictionally-fit). Distal connector protrusion 132a defines a plurality of cable channels 132b for receiving articulation cables 150 therein. Distal link 132 further includes a plurality of cable passages 132c in registration with cable channels 132b. Distal link 132 also includes a pair of ferrule pockets 132d defined in distal connector protrusion 132a for receiving ferrules 152c of a third pair of articulation cables 150c of the plurality of articulation cables 150 to secure distal portions of the third pair of articulation cables 150c to distal link 132 of proximal wrist assembly 130. Ferrule pockets 132d are disposed in registration with cable passages 132e defined through a proximal end portion of distal link 132 that slidably receive the third pair of articulation cables 150c therethrough. The third pair of articulation cables 150c is proximally offset from the first and second pairs of articulation cables 150a, 150b of the plurality of articulation cables 150 and positioned to enable distal link 132 to move relative to intermediate and proximal links 134, 136 of proximal wrist assembly 130. Distal link 132 also includes outer proximal pivot tabs 132f that define pin holes 132g therethrough for receiving a pin 99 (see FIG. 10) therein that pivotably couples distal link 132 to intermediate link 134 of proximal wrist assembly 130. Distal link 132 further defines a central lumen 132h therethrough for receiving flexible sleeve 106a of camera assembly 106 therethrough.

Figures 20A, 20B, 21A, 21B:
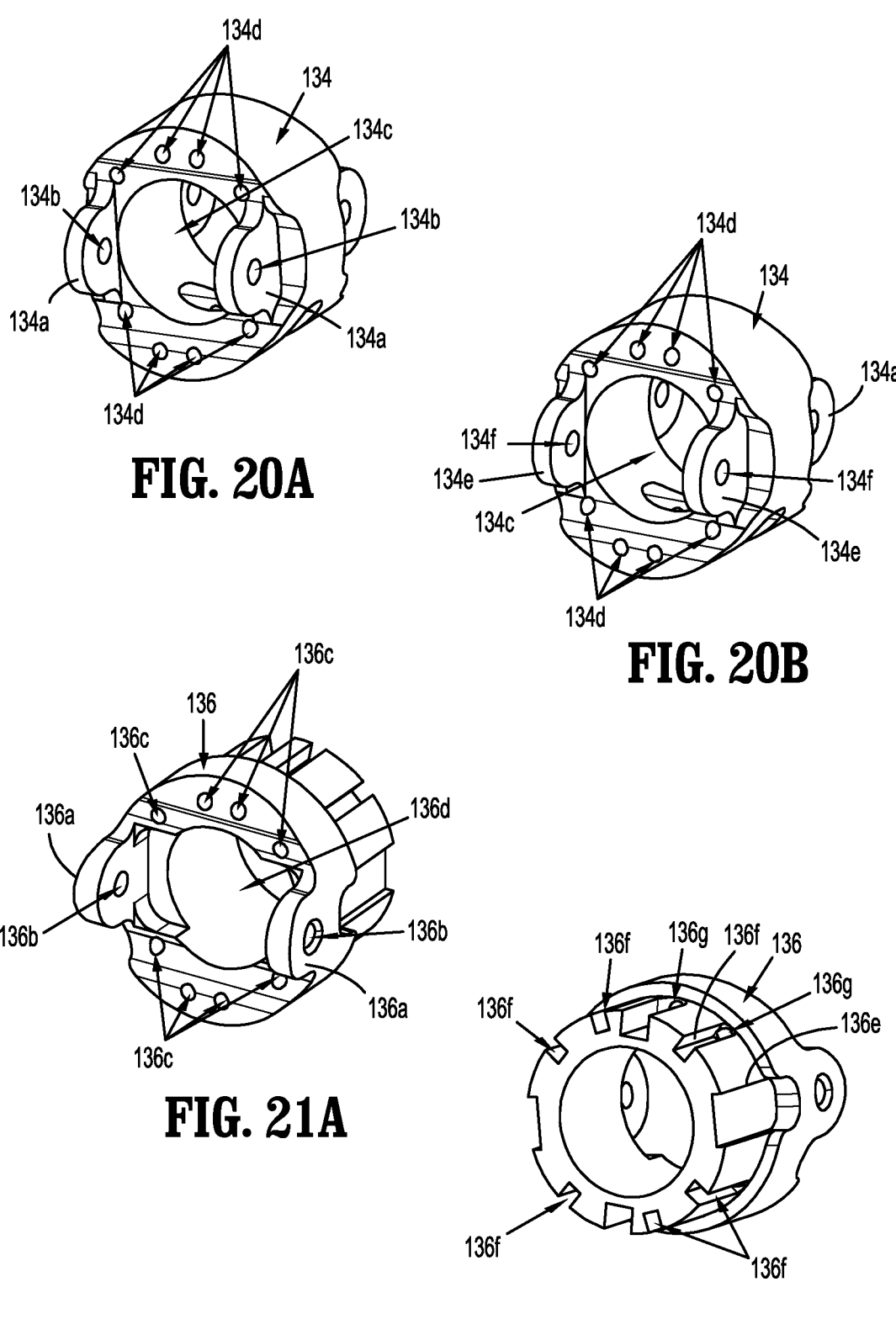

Referring now to FIGS. 20A and 20B, intermediate link 134 of proximal wrist assembly 130 includes inner distal pivot tabs 134a that define pin holes 134b therethrough for receiving the pin 99 (see FIG. 10) that pivotably couples the distal link 132 to the intermediate link 134 when inner distal pivot tabs 134a are aligned with (e.g., disposed adjacent to) outer proximal pivot tabs 132f of distal link 132. Intermediate link 134 defines a central lumen 134c therethrough for receiving flexible sleeve 106a of camera assembly 106 therethrough and a plurality of cable passages 134d therethrough for slidably receiving the articulation cables 150 therethrough. Intermediate link 134 further includes inner proximal pivot tabs 134e that define pin holes 134f therethrough for receiving a pin 99 (see FIG. 10) that pivotably couples intermediate link 134 to proximal link 136 of proximal wrist assembly 130.

With reference to FIGS. 21A and 21B, proximal link 136 of proximal wrist assembly 130 includes outer distal pivot tabs 136a that define pin holes 136b therethrough for receiving the pin 99 (see FIG. 10) that pivotably couples intermediate link 134 to proximal link 136 when outer distal pivot tabs 136a are aligned with (e.g., disposed adjacent to) inner proximal pivot tabs 134e of intermediate link 134. Proximal link 136 further includes a plurality of cable passages 136c for slidably receiving articulation cables 150 therethrough and a central lumen 136d for receiving flexible sleeve 106a of camera assembly 106 therethrough. Proximal link 136 also includes a proximal connector protrusion 136e extending proximally therefrom for coupling proximal link 136 to a distal portion of outer shaft 108 of inner shaft assembly 104 (see FIG. 11). Proximal connector protrusion 136e of proximal link 136 is received within a distal portion of central lumen 108c of outer shaft 108 (e.g., frictionally-fit) and defines a plurality of cable channels 136f in registration with cable passages 136g for receiving articulation cables 150. Articulation cables 150 extend proximally through endoscope 100 to any suitable drive mechanism (not explicitly shown) that may include, for example, motors, pulleys, gears, etc. to move cables 150 relative to the various disclosed links, for instance, to manipulate the endoscope 100 as desired.

Turning now to FIGS. 26-37, another dexterous endoscope is referred to generally as 200. Dexterous endoscope 200 defines a central longitudinal axis "L2." Dexterous endoscope 200 can be supported within outer sleeve 102 and can extend from a shaft assembly such as outer and inner shafts 108, 110 detailed above. Dexterous endoscope 200 includes an articulation assembly 204 that supports a camera assembly 206 and is positioned to articulate relative to central longitudinal axis "L2." For example, dexterous endoscope 200 is configured to pan (as illustrated by arrows "E" in FIG. 37), tilt (as illustrated by arrows "F" in FIG. 36), and/or elevate/descend (as illustrated by arrows "G" in FIG. 36) relative to central longitudinal axis "L2." Camera assembly 206 defines a plurality of ferrule pockets 206a therein (see FIG. 28).

Articulation assembly 204 of dexterous endoscope 200 includes a distal wrist assembly 220, a proximal wrist assembly 230, and a connector tube 240 that connects distal and proximal wrist assemblies 220, 230 together. Articulation assembly 204 further includes a plurality of articulation cables 250 that extend through articulation assembly 204 and enable movement of articulation assembly 204 in response to coordinated axial movement thereof (e.g., proximal/tightening and/or distal/loosening) by actuation of the one or more drive mechanisms, such as instrument drive assembly or endoscope drive assembly 20 of robotic surgical system 10. Articulation cables 250 support ferrules 252 on distal ends thereof that mount within ferrule pockets 206*a* of camera assembly 206 to facilitate articulating movement of articulation assembly 204 and camera assembly 206.

Distal wrist assembly 220 of articulation assembly 204 includes a ball joint assembly 220*a* and a first pin joint assembly 220*b* that is proximal to ball joint assembly 220*a*. Ball joint assembly 220*a* includes a distal head link 222, a distal ball joint link 224, an intermediate ball joint link 226, and proximal ball joint link 228. First pin joint assembly 220*b* includes a distal pin joint 221, an intermediate pin joint 223, and a proximal pin joint 225. Proximal wrist assembly 230 of articulation assembly 204 is in the form of a second pin joint assembly and includes a distal pin joint 232, an intermediate pin joint 234, and a proximal pin joint 236.

With reference to FIGS. 29A and 29B, distal head link 222 of ball joint assembly 220*a* has a ring shape and defines a plurality of cable passages 222*a* in an outer surface thereof positioned to slidably receive articulation cables 250 therein. Distal head link 222 further defines a central lumen 222*b* therethrough.

As seen in FIGS. 30A, 30B, and 35, distal ball joint link 224 includes a distal ball 224*a* and a proximal ball 224*b* that are coupled by a center ring 224*e*. Proximal ball 224*b* has a larger diameter than distal ball 224*a*. Proximal ball 224 defines a plurality of cable passages 224*c* in an outer surface thereof for slidably receiving articulation cables 250 therein. Distal ball joint link 224 further defines a central lumen 224*d* therethrough. Distal ball joint link 224 is disposed proximal to distal head link 222 with distal ball 224*a* of distal ball joint link 224 movably supported within a proximal end portion of distal head link 22 to form a ball joint therebetween. Intermediate ball joint link 226 is identical to distal ball joint link 224 with intermediate ball joint 226 positioned proximal to, and received within, proximal ball 224*b* of distal ball joint link 224 to form a ball joint therebetween.

With reference to FIGS. 31A-31C and 35, proximal ball joint link 228 includes a body 228*a* (e.g., a cylindrical body) that extends to a distal ball 228*b* that is movably received within proximal ball 224*b* of intermediate ball joint link 226 to form a ball joint therebetween. Body 228*a* tapers outwardly to a proximal ring 228*c* supported on a proximal end portion of body 228. Proximal ring 228*c* has a larger diameter than body 228*a* and extends to a proximal end face 228*d* of proximal ball joint link 228. Body 228*a* extends distally to a distal end face 228*e* and proximally to a proximal end face 228*f* recessed within a bore 228*k* of proximal ring 228*c*. Body 228*a* defines a plurality of cable passages 228*g* that extends through body 228*a* from proximal end face 228*f* to distal end face 228*e* for receiving articulation cables 250 therethrough. As seen in FIG. 31C, cable passages 228*g* can have a sinuous configurations that spiral around body 228*a*. Proximal ball joint link 228 further defines a central lumen 228*h* that extends through body 228*a*, distal ball 228*b*, and proximal ring 228*c*.

As seen in FIGS. 28, 32A, 32B, and 35, distal pin joint 221 of first pin joint assembly 220*b* extends between a first end face 221*a* on a first end of distal pin joint 221 and a second end face 221*b* on a second end of distal pin joint 221. First end face 221*a* includes a first surface 221*c* and a second surface 221*d* that are separated by an edge 221*e*. Second surface 221*d* is disposed at an angle relative to first surface 221*c* (e.g., slanted). Distal pin joint 221 further includes pivot pins 221*f* that extend from first surface 221*c* of first end face 221*a*. Pivot pins 221*f* define pin holes 221*g* therethrough for receiving a pivot pin 299 that pivotably couples a proximal portion of distal pin joint 221 to a distal portion of intermediate pin joint 223 of first pin joint assembly 220*b*. A distal portion of distal pin joint 221 is received (e.g., frictionally-fit) within bore 228*k* of proximal ball joint link 228. Distal pin joint 221 further defines a central lumen 221*h* therethrough and a plurality of cable passages 221*k* therethrough for slidably receiving articulation cables 250.

Proximal pin joint 225 of first pin joint assembly 220*b* is identical to distal pin joint 221 but is positioned in the opposite direction such that pivot pins 221*f* of proximal pin joint 225 extend distally, not proximally like distal pin joint 221. In particular, proximal pin joint 225 and distal pin joint 221 are mirrored about a plane transverse (e.g., orthogonal) to the longitudinal axis "L2" of dexterous endoscope 200. Further, proximal pin joint 225 includes a distal portion that is pivotably coupled to a proximal end portion of intermediate pin joint 223 by a pivot pin 299. A proximal portion of proximal pin joint 225 is received within (e.g., frictionally-fit) a distal portion of connector tube 240.

Distal pin joint 232 of second pin joint assembly 230 is identical to distal pin joint 221 of first pin joint assembly 220*b* but is oriented differently. More particularly, distal pin joint 232 is positioned in the same direction as distal pin joint 221 (e.g., with pivot pins 221*f* extending proximally), but is disposed in an inverted orientation (e.g., mirrored about a plane aligned with the longitudinal axis "L2" of dexterous endoscope 200 and extending therealong) relative to distal pin joint 221.

Proximal pin joint 236 of second pin joint assembly 230 is identical to distal pin joint 232 of second pin joint assembly 230, but is positioned in the opposite direction such that pivot pins 221*f* of proximal pin joint 236 extend distally, not proximally like distal pin joint 232. In particular, proximal pin joint 2236 and distal pin joint 232 of second pin joint assembly 230 are mirrored about a plane orthogonal to the longitudinal axis "L2" of dexterous endoscope 200. Further, proximal pin joint 236 includes a distal portion that is pivotably coupled to a proximal end portion of intermediate pin joint 234 by a pivot pin 299. A proximal portion of proximal pin joint 236 is also coupled to (e.g., received within) a proximal portion of dexterous endoscope 200, such as, for instance, outer and inner shafts 108, 110 thereof.

With reference to FIGS. 28, 33A, and 33B, intermediate pin joint 223 of first pin joint assembly 220*b* extends from a first end portion 223*a* to a second end portion 223*b* that is on an opposite end of intermediate pin joint 223. First and second end portions 223*a*, 223*b* are identical and disposed in mirrored relation to one another. First end portion 223*a* includes a first plurality of pivot pins 223*c* and second end portion 223*b* includes a second plurality of pivot pins 223*d*. Each of pivot pins 223*c*, 223*d* defines a pin hole 223*p* therethrough for receiving a pin 299 therein. Each of the first and second pluralities of pivot pins 223*c*, 223*d* includes a central pivot pin 223*e* and a pair of side pivot pins 223*f* disposed on opposite sides of central pivot pin 223*e*. Each side pivot pin 223*f* is disposed at an angle and faces inwardly toward central pivot pin 223*e*. Further, each of first and second end portions 223*a*, 223*b* includes first and second surfaces 223*g*, 223*h* that are separated by an edge 223*k*. First surface 223*g* is disposed at an angle relative to second surface 223*h* (e.g., slanted). Intermediate pin joint 223 further defines a central lumen 223*m* therethrough. Intermediate pin joint 223 also defines a plurality of cable passages 223*n* that slidably receives articulating cables 250 therethrough. A distal portion of intermediate pin joint 223 is pivotably coupled to a proximal portion of distal pin joint 221 of first pin joint assembly 220b and a proximal portion of intermediate pin joint 223 is pivotably coupled to a distal portion of proximal pin joint 225 of first pin joint assembly 220b.

Intermediate pin joint 234 of second pin joint assembly 230 is identical to intermediate pin joint 223 of first pin joint assembly 220b but is disposed in an inverted orientation relative thereto (e.g., disposed in mirrored relation therewith about a plane aligned with and extending along longitudinal axis "L2" of endoscope 200). A distal portion of intermediate pin joint 234 is pivotably coupled to a proximal portion of distal pin joint 232 of second pin joint assembly 230 and a proximal portion of intermediate pin joint 234 is pivotably coupled to a distal portion of proximal pin joint 236 of second pin joint assembly 230.

As seen in FIG. 34, connector tube 240 of articulation assembly 204 defines a central lumen 240a therethrough. Connector tube 240 further defines a plurality of apertures 240b therethrough.

Turning now to FIGS. 38-47, yet another dexterous endoscope is referred to generally as 300. Dexterous endoscope 300 defines a central longitudinal axis "L3." Dexterous endoscope 300 can be supported within outer sleeve 102 and can extend from a shaft assembly such as outer and inner shafts 108, 110 detailed above. Dexterous endoscope 300 includes an articulation assembly 304 that supports a camera assembly 306 and is positioned to articulate relative to central longitudinal axis "L3." For example, dexterous endoscope 300 is configured to pan (as illustrated by arrows "H" in FIG. 47), tilt (as illustrated by arrows "I" in FIG. 46), and/or elevate/descend (as illustrated by arrows "J" in FIG. 46) relative to central longitudinal axis "L3." Camera assembly 306 defines a plurality of ferrule pockets 306a therein (see FIG. 40).

Articulation assembly 304 of dexterous endoscope 300 includes a distal wrist assembly 320, a proximal wrist assembly 330, and a connector tube 240 that connects distal and proximal wrist assemblies 320, 330 together. Articulation assembly 304 further includes a plurality of articulation cables 350 that extends through articulation assembly 304 and enable movement of articulation assembly 304 in response to coordinated axial movement thereof (e.g., proximal/tightening and/or distal/loosening) by actuation of the one or more drive mechanisms, such as instrument drive assembly or endoscope drive assembly 20 of robotic surgical system 10. Articulation cables 350 support ferrules 352 (see FIG. 40) on distal ends thereof that mount within ferrule pockets 306a of camera assembly 306 to facilitate the articulating movement of articulation assembly 304 and camera assembly 306.

Distal wrist assembly 320 of articulation assembly 304 includes a distal head link 322, a distal vertebral link 324 proximal to distal head link 322, an intermediate vertebral link 325 proximal to distal vertebral link 324, a proximal vertebral link 326 proximal to intermediate vertebral link 325, and proximal tail link 328 proximal to proximal vertebral link 326. Proximal wrist assembly 330 of articulation assembly 304 includes a distal head link 332, an intermediate vertebral link 334, and a proximal tail link 336.

With reference to FIGS. 40, 41A, and 41B, distal head link 322 of articulation assembly 304 includes a coupling portion 322a on a first end thereof and a pivoting portion 322b on a second end thereof and which is wider than coupling portion 322a. Coupling portion 322a is received within (e.g., frictionally-fit) a recess 306b (see FIG. 40) defined within a proximal end portion of camera assembly 306. Distal head link 322 defines a central lumen 322c therethrough. Distal head link 322 further defines a plurality of cable passages 322d therethrough that slidably receive articulation cables 350 therethrough. Pivoting portion 322b of distal head link 322 includes a groove segment 322e on a first side thereof and a tooth segment 322f on a second side thereof so groove segment 322e and tooth segment 322f are diametrically opposed to one another and are configured to pivotably complement one another. Groove segment 322e defines a groove 322g therein and tooth segment 322f defines a tooth 322h extending therefrom. Pivoting portion 322b further includes a first slanted surface 322k and a second slanted surface 322j which are disposed on opposite sides of groove and tooth segments 322e, 322f. The plurality of cable passages 322d extends through the first and second slanted surfaces 322j, 322k. Pivoting portion 322b is positioned to pivotably engage a distal portion of distal vertebral link 324.

Proximal tail link 328 of distal wrist assembly 320, distal head link 332 of proximal wrist assembly 330, and proximal tail link 336 of proximal wrist assembly 330 all have the same structure as distal head link 322 of distal wrist assembly 320, but are coupled to different structures of articulation assembly 304 and may be oriented differently. For example, proximal tail link 328 is oriented in the opposite direction as distal head link 322 (e.g., in mirrored relation thereto). Moreover, proximal tail link 328 has a distal portion (e.g., pivoting portion 322b thereof) pivotally engaged with proximal vertebral link 326 and a proximal portion coupled to (e.g., frictionally-fit with) a distal portion of connector tube 240.

Similarly, while distal head link 332 of proximal wrist assembly 330 is oriented in the same direction as distal head link 322 of distal wrist assembly 320, distal head link 332 has distal portion (e.g., coupling portion 322a thereof) that is coupled to a proximal end portion of connector tube 240. Distal head link 322 also has a proximal portion (e.g., pivoting portion 322b thereof) that is pivotally coupled to intermediate vertebral link 334 of proximal wrist assembly 330.

Likewise, while proximal tail link 336 of proximal wrist assembly 330 is oriented in the opposite direction of distal head link 322 of distal wrist assembly 320, proximal tail link 336 has a distal portion (e.g., pivoting portion 322b thereof) that is pivotally coupled to a proximal portion of intermediate vertebral link 334 of proximal wrist assembly 330. Proximal tail link 336 has a proximal portion (e.g., coupling portion 322a thereof) that is coupled to a distal end portion of inner and outer shafts 110, 108 of endoscope 300.

With reference to FIGS. 42A and 42B, intermediate vertebral link 334 of proximal wrist assembly 330 has a first pivoting portion 334a on a first end thereof and a second pivoting portion 334b on a second end thereof. First pivoting portion 334a includes a first groove segment 334c on a first side of intermediate vertebral link 334 and a first tooth segment 334d on a second side of intermediate vertebral link 334. Similarly, second pivoting portion 334b has a second groove segment 334e on the second side of the intermediate vertebral link 334 and a second tooth portion 334f on the first side of intermediate vertebral link 334. In this regard, first pivoting portion 334a and second pivoting portion 334b have diagonal symmetry. Intermediate vertebral link 334 further defines a central lumen 334g therethrough. Intermediate vertebral link 334 also defines a plurality of cable passages 334h therethrough that slidably receive articulation cables 350 therethrough. First pivoting portion 334a of intermediate vertebral link 334 is pivotally coupled to pivoting portion 322b of proximal tail link 336 of proximal wrist assembly 330 such that first tooth segment 334d of intermediate vertebral link 334 engages groove segment 322e of proximal tail link 336 and first groove segment 334c of intermediate vertebral link 334 engages tooth segment 322f of proximal tail link 336. Similarly, second pivoting portion 334b of intermediate vertebral link 334 is pivotally coupled to pivoting portion 322b of distal head link 332 of proximal wrist assembly 330 such that the respective groove and tooth segments pivotably engage one another in corresponding fashion.

As seen in FIGS. 44A and 44B, distal vertebral link 324, intermediate vertebral link 325, and proximal vertebral link 326 of distal wrist assembly 320 have the same structure but different rotational orientations relative to one another (e.g., rotationally offset from one another). In particular, intermediate vertebral link 325 is rotated 90 degrees (about longitudinal axis "L3") relative to distal and proximal vertebral links 324, 326, and distal and proximal vertebral links 324, 326 are rotated 180 degrees (about longitudinal axis "L3") relative to one another. Each of distal vertebral link 324, intermediate vertebral link 325, and proximal vertebral link 326 includes a first pivoting portion 324a on a first end thereof and a second pivoting portion 324b on a second end thereof. First pivoting portion 324a includes a first groove segment 324c and a first tooth segment 324d. Second pivoting portion 324b includes a second groove segment 324e and a second tooth segment 324f that are transverse (e.g., orthogonal) to first groove and first tooth segments 324c, 324d of first pivoting portion 324a. Moreover, first and second pivoting portions 324a, 324b include slanted surfaces 324g, 324h that are also transverse (e.g., orthogonal) to one another. Further, each of distal vertebral link 324, intermediate vertebral link 325, and proximal vertebral link 326 defines a central lumen 324j and a plurality of cable passages 324k therethrough. The plurality of cable passages 324k are positioned to slidably receive articulation cables 350 therethrough.

Turning now to FIGS. 48-78, still another dexterous endoscope is referred to generally as 400. Dexterous endoscope 400 defines a longitudinal axis "L-L" therethrough and includes a housing assembly 402 supported on proximal end portion 400a thereof and an end effector 403 supported on a distal end portion 400b thereof. Housing 402 is coupled to end effector 403 via an elongated shaft assembly 405. Housing assembly 402 supports an electronics assembly 404 and a drive mechanism 406 that extend through elongated shaft assembly 405 and cooperate to operate the end effector 403.

With reference to FIGS. 48-51C, housing assembly 402 of dexterous endoscope 400 includes a proximal housing assembly 408 from which elongated shaft assembly 405 extends. Proximal housing assembly 408 includes a backplate 408a, brightness buttons 408b coupled to backplate 408a for changing light brightness of lights (e.g., light emitting diodes) of a camera head assembly 430 at distal end of dexterous endoscope 400 and a release assembly 408c for selectively enabling dexterous endoscope 400 to attach to movable drive unit 18 of robotic surgical system 10. Proximal housing assembly 408 further includes housing sidewalls 408d, a chassis 408e, and a housing grip 408f that cooperate with backplate 408a to support various components of dexterous endoscope 400. Release assembly 408c includes release buttons 408g and a spring 408f that urges release buttons 408g away from one another to enable dexterous endoscope 400 to be selectively attached to moveable drive unit 18. Release buttons 408g include release latches 408h supported by backplate 408a and which extend therefrom for selective engagement with movable drive unit 18.

As seen in FIGS. 52A and 52B, electronics assembly 404 of dexterous endoscope 400 is configured to provide surgical illumination, monitor LED temperatures, and communicate with, for example, instrument drive assembly or endoscope drive assembly 20 for authentication and control. Electronics assembly 404 includes an electrical connector assembly 412, a mainboard assembly 414, coaxial cables 416, fiber bundles 418, a cable sheath 420, a heatsink bracket 422, LED boards 424, thermal interface tape 426, a heatsink 428, and a camera assembly 430.

Camera assembly 430 of electronics assembly 404 includes a camera tube 432, a service cable tube 434, a camera board assembly 436 (e.g., serialiser PCB, CMOS PCB), a camera base 438, lens tubes 440, a camera top 442, and sapphire plates 444 that cooperate for lighting and/or imaging a surgical site.

With reference to FIGS. 52C and 52D, robotic surgical system 10 includes an electrical passthrough assembly 98 including a pair of electrical connector assemblies 412 and an interposer plate 413 that enable data and/or power to be passed between movable drive unit 18 and dexterous endoscope 400. A first one of the pair of electrical connector assemblies 412 couples to movable drive unit 18 and a second one of the pair of electrical connector assemblies 412 is part of electronics assembly 404 of dexterous endoscope 400. Each electrical connector assembly 412 includes a connector board 412a and pin platform 412b extending from connector board 412a. Pin platform 412b supports a plurality of contact pins 412c with exposed faces 412d. Exposed faces 412d may be flat or substantially flat and may be flush or substantially flush with an end face of pin platform 412b. Interposer plate 413 functions as an interface between the pair of electrical connector assemblies 412 and supports a plurality of spring-biased pins 413a (e.g., pogo pins) that are positioned to move between extended and retracted positions relative to interposer plate 413, as indicated by arrows "ER", shown in FIG. 52D.

Turning now to FIGS. 53 and 54, drive mechanism 406 of dexterous endoscope 400 is configured to convert a motor angle of instrument drive assembly or endoscope drive assembly 20 into cable length ratios, as will be described in detail below. Drive mechanism 406 includes a cable assembly 450 and a drive train assembly 452 that are coupled together to impart drive force from the proximal end portion 400a of the dexterous endoscope 400 to the distal end portion 400b of the dexterous endoscope 400 for operating and/or moving end effector 403 relative to housing assembly 402. Cable assembly 450 includes pan cables 450a for effecting panning movement of end effector 403 relative to longitudinal axis "L-L" of dexterous endoscope 400, tilt cables 450b for effectuating tilting movement of end effector 403 relative to longitudinal axis "L-L", and elevate cables 450c for effectuating elevational movement of end effector 403 relative to longitudinal axis "L-L". Drive train assembly 452 includes a pan drive train 452a, a tilt drive train 452b, and an elevate drive train 452c that are coupled to a proximal bearing plate 454 and a distal bearing plate 456 via bearings 457. Pan, tilt, and elevate cables 450a, 450b, 450c are configured to cam along and/or wind around pan, tilt, and elevate drive trains 452a, 452b, 452c, for instance, to accommodate changes in cable tension, cable length, and/or changes in cable positioning for moving end effector 403 between various articulated and/or unarticulated positions (e.g., pan, tilt, or evaluate). In aspects, the cables may include Tungsten. The cables may be protected with coil pipes to provide low friction, high wear bearing surfaces for flexible routing.

Pan drive train 452a includes a drive shaft assembly 458 and a drive dog assembly 460 coupled thereto. Drive shaft assembly 458 includes a drive shaft 458a that supports spools 458b and a circular hub 458c (e.g., a toothed clutch) between circular spools 458b. Drive shaft 458a defines annular channels 458d that are longitudinally spaced apart and positioned to receive drive clips 458e (e.g., an e-clip) therein. Drive shaft 458a further includes a proximal rib 458f that engages with pan drive dog assembly 460. Drive dog assembly 460 includes a drive dog 462, a lockout plate 464, and springs 466. Drive dog 462 is configured to remain in position axially and lockout plate 464 is configured to axially slide against biasing force from springs 466 for selectively unlocking drive dog 462.

With reference to FIGS. 54-56, tilt drive train 452b and elevate drive train 452c are substantially similar to pan drive train 452a, but tilt and elevate drive trains 452b, 452c include elongated lengthener hubs with central barrel portions thereof having non-circular cross-sections across the longitudinal axis thereof (e.g., nautilus-shaped, tear-drop shaped, and/or logarithmic-spiral-shaped cross-sections). By comparison, circular hub 458c of pan drive train 452a has a circular cross-section across the longitudinal axis thereof. In particular, elevate drive train assembly 452c includes an elongated lengthener hub 470 (in the form of a nautilus cam) that is secured to an intermediate portion of a drive shaft assembly 458 thereof via a set screw 472. Elongated lengthener hub 470 of elevate drive train 452c includes circular toothed spools 470a, 470b on opposite ends of a non-circular central barrel portion of elongated lengthener hub 470. Circular toothed spools 470a, 470b engage with circular spools 458b of elevate drive train 452c. Drive clips 458e secure circular spools 458b and elongated lengthener hub 470 on drive shaft assembly 458 of elevate drive train 452c. Tilt drive train 452b is substantially similar to elevate drive train 452c, but tilt drive train 452b has an elongated lengthener hub 474 (in the form of a nautilus cam) that is shorter in length than elongated lengthener hub 470 of elevate drive train 452c, but otherwise has a substantially similar cross-section as elongated lengthener hub 470. Elongated lengthener hub 474 also is radially closer to a central longitudinal axis of drive shaft assembly 458 of tilt drive train 452b than elongated lengthener hub 470 of elevate drive train 452c. Indeed, an apex 470a of elongated lengthener hub 470 of elevate drive train 452c extends radially farther than circular spools 458b of elevate drive train 452c relative to the central longitudinal axis of drive shaft assembly 458 of elevate drive train 452c. By comparison, circular spools 458b of tilt drive train 452b extend radially farther than an apex 474a of elongated lengthener hub 470 of tilt drive train 452b relative to the central longitudinal axis of drive shaft assembly 458 of tilt drive train 452b.

Elongated lengthener hubs 470, 474 of tilt and elevate drive trains 452b, 452c function to maintain cable tension accounting for joint angle changes in wrist assemblies of elongated shaft assembly 405 that would otherwise cause slack in one or more of the cables of cable assembly 450.

Turning now to FIGS. 57-65, pan cables 450a, tilt cables 450b, and elevate cables 450c of cable assembly 450 have ends 450x thereof fixed to cable channels 458x defined in the various circular spools 458b via ferrules 450z. Regarding elevate cables 450c, a first elevate cable 1450c of elevate cables 450c winds around and couples to first circular spool 1458b of elevate drive train 452c, as seen in FIG. 58, and a second elevate cable 2450c of elevate cables 450c winds around and couples to a second circular spool 2458b of elevate drive train 452c, as seen in FIG. 65, on an opposite end portion of elevate drive train 452c. Regarding tilt cables 450b, a first tilt cable 1450b of tilt cables 450b winds around elongated lengthener hub 470 and a first circular spool 1458b of tilt drive train 452b so that the end of first tilt cable 1450b couples to first circular spool 1458b of tilt drive train 452b, as seen in FIG. 61. As seen in FIG. 64, a second tilt cable 2450b of tilt cables 450b winds around elongated lengthener hub 470 of elevate drive train 452c and a second circular spool 2458b of tilt drive train 452b so that the end of second tilt cable 2450b couples to second circular spool 2458b of tilt drive train 452b. Regarding pan cables 450a, a first pan cable 1450a of pan cables 450a winds around elongated lengthener hub 470 of elevate drive train 452c and elongated lengthener hub 474 of tilt drive train 452b and couples to a first circular spool 1458b of pan drive train 452a, as seen in FIG. 62. With reference to FIG. 63, a second pan cable 2450a of pan cables 450a winds around elongated lengthener hub 470 of elevate drive train 452c, elongated lengthener hub 474 of tilt drive train 452b, and a second circular spool 2458b of pan drive train 452a so that an end of second pan cable 2450a couples to second circular spool 2458b of pan drive train 452a.

Turning now to FIGS. 66-78, the elongated shaft assembly 405 of dexterous endoscope 400 is similar to the elongated shaft assembly of dexterous endoscope 100. Indeed, elongated shaft assembly 405 includes an outer shaft 460 and an inner shaft assembly 462. Inner shaft assembly 462 includes a proximal shaft 464 that extends distally from housing assembly 402 and an inner sleeve assembly 466 that couples to and extends distally from proximal shaft 464. Proximal shaft 464 includes an angled proximal segment 464a coupled to housing assembly 402 and a straight segment 464b that extends distally from angled proximal segment 464a to a distal portion 464c having a plurality of vent holes 464d defined in annular arrays about distal portion 464c, as seen in FIG. 51C, for improving drainage in cleaning, inspection, and assembly. Angled proximal segment 464a is positioned to influence orientation and position of end effector 403.

Similar to inner sleeve assembly 104, inner sleeve assembly 466 includes an articulation assembly 466a having a proximal wrist assembly 468, a distal wrist assembly 470, and a connector tube 472 that is supported between proximal and distal wrist assemblies 468, 470. Connector tube 472 defines a plurality of vent apertures 472a therethrough. Also similar to inner sleeve assembly 104, inner sleeve assembly 466 includes a plurality of links 468a, 468b, 470a, 470b, 470c that coupled together via cable assembly 450 and which are movable to convert cable length ratios of cable assembly 450 into different positions of camera assembly 430. Ends of cable assembly 450 are coupled to these plurality of links via ferrules 467. The plurality of links are pivotally coupled together to adjacent links of these plurality of links via pivot pins 469 such that axially movement of one or more cables of cable assembly 450 causes articulating movement such as panning, tilting, and/or elevating/descending movement of end effector 403 (e.g., camera assembly 430) relative to longitudinal axis "L-L." The plurality of links define gaps 465a and include abutments 465b and beveled surfaces 465c that cooperate to enable up to 45 degrees of panning movement, up to 68 degrees of tilting movement, and up to 68 degrees of elevating movement while limiting maximum joint angle to prevent overdriving.

As seen in FIG. 79, endoscopes of this disclosure can be made of variety of different materials such as plastic, metal, rubber, silicone, etc. to seal, protect, and/or insulate various components thereof.

As can be appreciated any of the central lumens of the various components of the disclosed endoscopes are configured to receive electrical wiring/cables, fiberoptic bundles, etc. therethrough. Such wiring/cables, fiberoptic bundles enable the disclosed camera assemblies to communicate with, for example, workstation 12 and/or instrument cart 14.

Securement of any of the components of the disclosed devices may be effectuated using known securement techniques such welding, crimping, gluing, fastening, etc.

Also disclosed is a robotic surgical system, comprising: a drive assembly; and a dexterous endoscope operatively coupled to the drive assembly and defining a longitudinal axis, the dexterous endoscope including: a camera module assembly; and an articulation assembly supporting the camera module assembly on a distal end portion thereof and being actuatable by the drive assembly, the articulation assembly including a ball joint assembly, a first pin joint assembly, and a second pin joint assembly that are movable relative to one another to articulate the camera module assembly relative to the longitudinal axis of the dexterous endoscope.

The robotic surgical system of the preceding robotic surgical system clause wherein the first pin joint assembly is disposed proximal to the ball joint assembly and distal to the second pin joint assembly.

The robotic surgical system of any one of the preceding robotic surgical system clauses, further comprising a connector tube that separates the first pin joint assembly and the second pin joint assembly.

The robotic surgical system of any one of the preceding robotic surgical system clauses, wherein the ball joint assembly includes a first plurality of links.

The robotic surgical system of any one of the preceding robotic surgical system clauses, wherein the first plurality of links includes a distal ball joint link, an intermediate ball joint link disposed proximal to distal ball joint link, and a proximal ball joint link that is disposed proximal to intermediate ball joint link.

The robotic surgical system of any one of the preceding robotic surgical system clauses, further comprising a distal head link coupled to a distal end portion of distal ball joint link, the distal head link positioned to support the camera module assembly.

The robotic surgical system of any one of the preceding robotic surgical system clauses, wherein the first pin joint assembly includes a second plurality of links.

The robotic surgical system of any one of the preceding robotic surgical system clauses, wherein the second plurality of links includes a first distal pin joint, a first intermediate pin joint disposed proximal to the first distal pin joint, and a first proximal pin joint, the first proximal pin joint disposed proximal to the first intermediate pin joint.

The robotic surgical system of any one of the preceding robotic surgical system clauses, wherein the second pin joint assembly includes a third plurality links.

The robotic surgical system of paragraph any one of the preceding robotic surgical system clauses, wherein the third plurality of links includes a second distal pin joint, a second intermediate pin joint disposed proximal to the second distal pin joint, and a second proximal pin joint, the second proximal pin joint disposed proximal to the second intermediate pin joint.

A surgical system, comprising: an insertion tube defining a plurality of conduits therethrough; a first surgical instrument insertable through a first one of the plurality of conduits; and a dexterous endoscope defining a longitudinal axis and insertable through a second one of the plurality of conduits and including: a camera module assembly; and an articulation assembly supporting the camera module assembly and being actuatable to pan, tilt, and/or elevate the camera module assembly relative to the longitudinal axis, the articulation assembly including a ball joint assembly, a first pin joint assembly, and a second pin joint assembly that are movable relative to one another.

The surgical system of the preceding surgical system clause, wherein the first pin joint assembly is disposed proximal to the ball joint assembly and distal to the second pin joint assembly.

The surgical system of any one of the preceding surgical system clauses, further comprising a connector tube that separates the first pin joint assembly and the second pin joint assembly.

The surgical system of any one of the preceding surgical system clauses, wherein the ball joint assembly includes a first plurality of links.

The surgical system of any one of the preceding surgical system clauses, wherein the first plurality of links includes a distal ball joint link, an intermediate ball joint link disposed proximal to the distal ball joint link, and a proximal ball joint link that is disposed proximal to the intermediate ball joint link.

The surgical system of any one of the preceding surgical system clauses, further comprising a distal head link coupled to a distal end portion of the distal ball joint link, the distal head link positioned to support the camera module assembly.

The surgical system of any one of the preceding surgical system clauses, wherein the first pin joint assembly includes a second plurality of links.

The surgical system of any one of the preceding surgical system clauses, wherein the second plurality of links includes a first distal pin joint, a first intermediate pin joint disposed proximal to the first distal pin joint, and a first proximal pin joint, the first proximal pin joint disposed proximal to the first intermediate pin joint.

The surgical system of any one of the preceding surgical system clauses wherein the second pin joint assembly includes a third plurality links.

A surgical system, comprising: a drive assembly; and dexterous endoscope defining a longitudinal axis and actuatable by the drive assembly, the dexterous endoscope including: a camera module assembly; and an articulation assembly supporting the camera module assembly and being actuatable to pan, tilt, and/or elevate the camera module assembly relative to the longitudinal axis, the articulation assembly including a distal wrist assembly and a proximal wrist assembly that are coupled together by a plurality of articulation cables, the distal wrist assembly including a ball joint assembly and a first pin joint assembly that are movable relative to one another, the proximal wrist assembly including a plurality of joints pinned together.

A robotic surgical system, comprising: a drive assembly; and a dexterous endoscope operatively coupled to the drive assembly and defining a longitudinal axis, the dexterous endoscope including: a camera module assembly; and an articulation assembly supporting the camera module assembly on a distal end portion thereof and being actuatable by the drive assembly, the articulation assembly including a first wrist assembly having a plurality of vertebral links that are pivotable relative to one another to articulate the camera module assembly relative to the longitudinal axis of the dexterous endoscope.

The robotic surgical system of the preceding robotic surgical system clause, further comprising a second wrist assembly having a plurality of links, the links of the plurality of links of the second wrist assembly are pivotable relative to one another.

The robotic surgical system of any one of the preceding robotic surgical system clauses, wherein each vertebral link of the plurality of vertebral links includes a tooth segment and a groove segment.

The robotic surgical system of any one of the preceding robotic surgical system clauses, wherein the tooth segment and the groove segment are disposed on diametrically opposed sides of each respective vertebral link.

The robotic surgical system of any one of the preceding robotic surgical system clauses, further comprising a plurality of articulation cables coupled to the plurality of vertebral links, the plurality of articulation cables being actuatable to move the vertebral links of the plurality of vertebral links relative to one another.

The robotic surgical system of any one of the preceding robotic surgical system clauses, wherein at least some of the plurality of vertebral links define cable passages therethrough that slidably receive the plurality of articulation cables.

The robotic surgical system of any one of the preceding robotic surgical system clauses, wherein the plurality of articulation cables supports ferrules that secure the plurality of articulation cables to at least one vertebral link of the plurality of vertebral links.

The robotic surgical system of any one of the preceding robotic surgical system clauses, wherein the plurality of vertebral links includes a first distal vertebral link, a first intermediate vertebral link rotationally offset from the first distal vertebral link, and a first proximal vertebral link rotationally offset from the first intermediate vertebral link.

The robotic surgical system of any one of the preceding robotic surgical system clauses, further comprising a first distal head link pivotably coupled to the first distal vertebral link and a first proximal tail link pivotably coupled to the first proximal vertebral link, the first distal head link supporting the camera module assembly.

The robotic surgical system of any one of the preceding robotic surgical system clauses, wherein the second wrist assembly is proximal to the first wrist assembly, and wherein the plurality of links of the second wrist assembly includes a second distal head link, a second intermediate vertebral link pivotably coupled to the second distal head link, and a second proximal tail link pivotably coupled to the second intermediate vertebral link.

A surgical system, comprising: an insertion tube defining a plurality of conduits therethrough; a first surgical instrument insertable through a first one of the plurality of conduits; and a dexterous endoscope defining a longitudinal axis and insertable through a second one of the plurality of conduits and including: a camera module assembly; and an articulation assembly supporting the camera module assembly and being actuatable to pan, tilt, and/or elevate the camera module assembly relative to the longitudinal axis, the articulation assembly including a first wrist assembly, a second wrist assembly, and a connector tube that couples the first and second wrist assemblies together, the first wrist assembly including a plurality of vertebral links, wherein the vertebral links of the plurality of vertebral links are pivotably coupled to one another.

The surgical system of the preceding surgical system clause, wherein each vertebral link of the plurality of vertebral links includes a tooth segment and a groove segment.

The surgical system of any one of the preceding surgical system clauses, wherein the tooth segment and the groove segment are disposed on diametrically opposed sides of each respective vertebral link.

The surgical system of any one of the preceding surgical system clauses, further comprising a plurality of articulation cables coupled to the plurality of vertebral links, the plurality of articulation cables actuatable to move the vertebral links of the plurality of vertebral links relative to one another.

The surgical system of any one of the preceding surgical system clauses, wherein at least some of the vertebral links of the plurality of vertebral links define cable passages therethrough that slidably receive the plurality of articulation cables.

The surgical system of any one of the preceding surgical system clauses, wherein the plurality of articulation cables supports ferrules that secure the plurality of articulation cables to at least one vertebral link of the plurality of vertebral links.

The surgical system of any one of the preceding surgical system clauses wherein the plurality of vertebral links includes a first distal vertebral link, a first intermediate vertebral link rotationally offset from the first distal vertebral link, and a first proximal vertebral link rotationally offset from the first intermediate vertebral link.

The surgical system of any one of the preceding surgical system clauses, further comprising a first distal head link pivotably coupled to the first distal vertebral link and a first proximal tail link pivotably coupled to the first proximal vertebral link, the first distal head link supporting the camera module assembly.

The robotic surgical system of any one of the preceding surgical system clauses, wherein the second wrist assembly is proximal to the first wrist assembly, the second wrist assembly including a second distal head link, a second intermediate vertebral link pivotably coupled to the second distal head link, and a second proximal tail link pivotably coupled to the second intermediate vertebral link.

A surgical system, comprising: a drive assembly; and a dexterous endoscope defining a longitudinal axis and actuatable by the drive assembly, the dexterous endoscope including: a camera module assembly; and an articulation assembly supporting the camera module assembly and being actuatable to pan, tilt, and/or elevate the camera module assembly relative to the longitudinal axis, the articulation assembly including a distal wrist assembly and a proximal wrist assembly that are coupled together by a plurality of articulation cables and a connector tube, the distal wrist assembly including at least one vertebral link and the proximal wrist assembly including at least one vertebral link.

A surgical system, comprising: a drive assembly; and a dexterous endoscope defining a longitudinal axis, the dexterous endoscope actuatable by the drive assembly and including a camera assembly and a drive mechanism, the drive mechanism operatively coupled to the drive assembly, the drive mechanism including a cable assembly and a drive train assembly that is operatively coupled to the cable assembly, the drive train assembly actuatable to manipulate the cable assembly, wherein manipulation of the cable assembly causes the camera assembly to pan up to 45 degrees relative to the longitudinal axis, tilt up to 68 degrees relative to the longitudinal axis, or elevate up to 68 degrees relative to the longitudinal axis.

The surgical system of the preceding surgical system clause, wherein the drive mechanism includes a pan drive train that is rotatable to cause panning movement of the camera assembly.

The surgical system of any one of the preceding surgical system clauses, wherein the drive mechanism includes a tilt drive train that is rotatable to cause tilting movement of the camera assembly.

The surgical system of any one of the preceding surgical system clauses, wherein the drive mechanism includes an elevate drive train that is rotatable to cause the camera assembly to elevate or descend relative to the longitudinal axis.

The surgical system of any one of the preceding surgical system clauses, wherein at least one of the elevate drive train or the tilt drive train includes an elongated lengthener hub having a non-circular cross section.

The surgical system of any one of the preceding surgical system clauses, wherein the elevate drive train includes a first elongated lengthener hub that extends to a first apex and the tilt drive train includes a second lengthener hub that extends to a second apex.

The surgical system of any one of the preceding surgical system clauses, wherein the first apex extends to a first radial distance from a first longitudinal axis of the elevate drive train.

The surgical system of any one of the preceding surgical system clauses, wherein the second apex extends to a second radial distance from a second longitudinal axis of the tilt drive train.

The surgical system of any one of the preceding surgical system clauses, wherein the second radial distance is different from the first radial distance.

The surgical system of any one of the preceding surgical system clauses, wherein the pan drive train includes a hub having a circular cross section.

A surgical system, comprising: an insertion tube defining a plurality of conduits therethrough; a first surgical instrument insertable through a first one of the plurality of conduits; and a dexterous endoscope defining a longitudinal axis and insertable through a second one of the plurality of conduits, the dexterous endoscope movable between articulated and unarticulated positions relative to the longitudinal axis and including a camera assembly and a drive mechanism, the drive mechanism including a cable assembly and a drive train assembly that is operatively coupled to the cable assembly, the drive train assembly actuatable to manipulate the cable assembly, wherein the drive train assembly includes at least one elongated lengthener hub having a non-circular cross-section around which the cable assembly winds, the at least one elongated lengthener hub is configured to maintain constant cable tension in the cable assembly as the dexterous endoscope moves between the articulated and unarticulated positions relative to the longitudinal axis.

The surgical system of the preceding surgical system clause, wherein the drive mechanism includes a pan drive train that is rotatable to cause panning movement of the camera assembly.

The surgical system of of any one of the preceding surgical system clauses, wherein the drive mechanism includes a tilt drive train that is rotatable to cause tilting movement of the camera assembly.

The surgical system of of any one of the preceding surgical system clauses, wherein the drive mechanism includes an elevate drive train that is rotatable to cause the camera assembly to elevate or descend relative to the longitudinal axis.

The surgical system of of any one of the preceding surgical system clauses, wherein the elevate drive train includes a first elongated lengthener hub and the tilt drive train has a second elongated lengthener hub.

The surgical system of of any one of the preceding surgical system clauses, wherein the first elongated lengthener hub extends to a first apex and the second lengthener hub extends to a second apex.

The surgical system of of any one of the preceding surgical system clauses, wherein the first apex extends to a first radial distance from a first longitudinal axis of the elevate drive train, and wherein the second apex extends to a second radial distance from a second longitudinal axis of the tilt drive train.

The surgical system of of any one of the preceding surgical system clauses, wherein the second radial distance is different from the first radial distance.

The surgical system of of any one of the preceding surgical system clauses, wherein the pan drive train includes a hub having a circular cross section.

A robotic surgical system, comprising: a drive assembly; and a dexterous endoscope operatively coupled to the drive assembly, the dexterous endoscope defining a longitudinal axis and including a camera assembly and a robotically controlled drive mechanism, the drive mechanism including a cable assembly and a drive train assembly that is operatively coupled to the cable assembly, the drive train assembly actuatable to manipulate the cable assembly, wherein manipulation of the cable assembly causes the camera assembly to pan up to 45 degrees relative to the longitudinal axis, tilt up to 68 degrees relative to the longitudinal axis, or elevate up to 68 degrees relative to the longitudinal axis.

Persons skilled in the art will understand that the structures and methods specifically described herein and shown in the accompanying figures are non-limiting exemplary aspects, and that the description, disclosure, and figures should be construed merely as exemplary of aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. A robotic surgical system, comprising:
a drive assembly;
an insertion tube; and
a dexterous endoscope defining a longitudinal axis and insertable through the insertion tube, the dexterous endoscope operatively coupled to the drive assembly, the drive assembly being actuatable to manipulate the dexterous endoscope, the dexterous endoscope including:
a camera module assembly having a compact camera module and a sleeve extending proximally from the compact camera module; and
an articulation assembly supporting the compact camera module on a distal end portion of the articulation assembly, the articulation assembly being actuatable
to move the compact camera module relative to the
longitudinal axis of the dexterous endoscope, the
articulation assembly including a distal wrist assem-
bly and a proximal wrist assembly that receive the
sleeve of the camera module assembly the distal
wrist assembly and the proximal wrist assembly,
the distal wrist assembly including a first plurality of
links, the links of the first plurality of links being
movable relative to one another to enable the com-
pact camera module to pivot in a first direction about
a first pivot axis extending orthogonal to the longi-
tudinal axis, and to enable the compact camera
module to pivot in a second direction about a second
pivot axis extending orthogonal to the longitudinal
axis and extending orthogonal to the first pivot axis,
the proximal wrist assembly including a second plu-
rality of links, the links of the second plurality of
links being movable relative to one another to enable
the compact camera module and the distal wrist
assembly to pivot in a third direction about a third
pivot axis extending orthogonal to the longitudinal
axis and extending parallel to the first pivot axis.
2. The robotic surgical system of claim 1, wherein the first
plurality of links is pinned together.
3. The robotic surgical system of claim 2, wherein the
second plurality of links is pinned together.
4. The robotic surgical system of claim 3, wherein the
articulation assembly includes a plurality of articulation
cables that extends through at least some links of the first
plurality of links.
5. The robotic surgical system of claim 4, wherein the
plurality of articulation cables extends through at least some
links of the second plurality of links.
6. The robotic surgical system of claim 5, wherein at least
some cables of the plurality of articulation cables are
coupled to at least one link of the second plurality of links
by ferrules.
7. The robotic surgical system of claim 6, wherein at least
some articulation cables of the plurality of articulation
cables are coupled to at least one link of the first plurality of
links by ferrules.
8. The robotic surgical system of claim 1, wherein at least
some of the links of the first and second plurality of links
define cable passages therethrough for supporting the plu-
rality of articulation cables.
9. The robotic surgical system of claim 1, wherein the first
plurality of links includes:
a distal head link engaged with the compact camera
module,
a distal link that is pivotably coupled to the distal head
link, wherein the distal head link and the distal link are
pivotable about the first pivot axis,
an intermediate link that is pivotably coupled to the distal
link, wherein the distal link and the intermediate link
are pivotable about the second pivot axis, and
a proximal link that is pivotably coupled to the interme-
diate link and frictionally engaged with a distal end
portion of a connector tube.
10. The robotic surgical system of claim 9, wherein the
second plurality of links includes:
a distal link frictionally engaged with a proximal end
portion of the connector tube,
an intermediate link pivotably coupled to the distal link of
the second plurality of links, wherein the distal link and
the intermediate link are pivotable about the third pivot
axis, and a proximal link pivotably coupled to the intermediate link
of the second plurality of links, wherein the interme-
diate link and the proximal link are pivotable about a
fourth pivot axis extending parallel to the third pivot
axis.
11. A surgical system, comprising:
an insertion tube defining a plurality of conduits there-
through;
a first surgical instrument insertable through a first one of
the plurality of conduits; and
a dexterous endoscope defining a longitudinal axis and
insertable through a second one of the plurality of
conduits and including:
a camera module assembly; and
an articulation assembly supporting the camera module
assembly and being actuatable to pan, tilt, and/or
elevate the camera module assembly relative to the
longitudinal axis, the articulation assembly including
a distal wrist assembly and a proximal wrist assem-
bly that are longitudinally spaced apart by a connec-
tor tube, the distal and proximal wrist assemblies
movable relative to one another and the connector
tube, wherein:
the distal wrist assembly enabling the camera module
assembly to pivot in a first direction about a first
pivot axis extending orthogonal to the longitudinal
axis, and enabling the camera module assembly to
pivot in a second direction about a second pivot axis
extending orthogonal to the longitudinal axis and
extending orthogonal to the first pivot axis; and
the proximal wrist assembly enabling the camera mod-
ule assembly and the distal wrist assembly to pivot in
a third direction about a third pivot axis extending
orthogonal to the longitudinal axis and extending
parallel to the first pivot axis.
12. The surgical system of claim 11, wherein surgical
system includes a second surgical instrument that is insert-
able through a third one of the plurality of conduits and a
third surgical instrument that is insertable through a fourth
one of the plurality of conduits, wherein the dexterous
endoscope, the first instrument, the second instrument, and
the third instrument are simultaneously positionable within
the four separate conduits.
13. The surgical system of claim 11, wherein the distal
wrist assembly includes a first plurality of links, the links of
the first plurality of links being movable relative to one
another to enable panning and tilting of the camera module
assembly, the proximal wrist assembly including a second
plurality of links, the links of the second plurality of links
being movable relative to one another to enable elevating of
the cameral module assembly.
14. The surgical system of claim 13, wherein the first
plurality of links is pinned together.
15. The surgical system of claim 14, wherein the second
plurality of links is pinned together.
16. The surgical system of claim 13, wherein the articu-
lation assembly includes a plurality of articulation cables
that extends through at least some links of the first plurality
of links.
17. The surgical system of claim 16, wherein the plurality
of articulation cables extends through at least some links of
the second plurality of links.
18. The surgical system of claim 17, wherein at least some
articulation cables of the plurality of articulation cables are
coupled to at least one link of the second plurality of links
by ferrules.

19. The surgical system of claim 18, wherein at least some articulation cables of the plurality of articulation cables are coupled to at least one link of the first plurality of links by ferrules.

20. A surgical system, comprising:

a drive assembly; and a dexterous endoscope defining a longitudinal axis and actuatable by the drive assembly, the dexterous endoscope including:

a camera module assembly; and an articulation assembly supporting the camera module assembly and being actuatable to pan, tilt, and/or elevate the camera module assembly relative to the longitudinal axis, the articulation assembly including a distal wrist assembly and a proximal wrist assembly that are coupled together by a plurality of articulation cables, the distal wrist assembly including a first plurality of links, the links of the first plurality of links are movable relative to one another to enable the camera module assembly to pivot in a first direction about a first pivot axis extending orthogonal to the longitudinal axis, and to enable the camera module assembly to pivot in a second direction about a second pivot axis extending orthogonal to the longitudinal axis and extending orthogonal to the first pivot axis, the proximal wrist assembly includes a second plurality of links, the links of the second plurality of links are movable relative to one another to enable the camera module assembly and the distal wrist assembly to pivot in a third direction about a third pivot axis extending orthogonal to the longitudinal axis and extending parallel to the first pivot axis, and the first plurality of links includes at least three links pinned together, and the second plurality of links includes at least three links pinned together.

* * * * *